US012527601B2

(12) United States Patent
Chen

(10) Patent No.: US 12,527,601 B2
(45) Date of Patent: Jan. 20, 2026

(54) PEDICLE ANCHOR FOR USE IN TRANSLAMINAR PEDICLE ANCHOR SUSPENSION SYSTEM AND COMPONENT SET THEREOF

(71) Applicant: Chien-Yu Chen, Taipei (TW)

(72) Inventor: Chien-Yu Chen, Taipei (TW)

( * ) Notice: Subject to any disclaimer, the term of this patent is extended or adjusted under 35 U.S.C. 154(b) by 696 days.

(21) Appl. No.: 17/985,841

(22) Filed: Nov. 12, 2022

(65) Prior Publication Data

US 2023/0070201 A1 Mar. 9, 2023

Related U.S. Application Data

(63) Continuation-in-part of application No. 17/501,267, filed on Oct. 14, 2021, now Pat. No. 12,465,407, which is a continuation-in-part of application No. 17/193,320, filed on Mar. 5, 2021, now Pat. No. 11,172,964.

(51) Int. Cl.
*A61B 17/70* (2006.01)

(52) U.S. Cl.
CPC ...... *A61B 17/7001* (2013.01); *A61B 17/7082* (2013.01); *A61B 17/7091* (2013.01)

(58) Field of Classification Search
CPC ............ A61B 17/7022; A61B 17/7026; A61B 17/7031; A61B 17/7053; A61B 17/7062–7071; A61B 17/82; A61B 17/84; A61B 17/842; A61B 17/8645; A61B 2017/0414; A61B 17/0401
See application file for complete search history.

(56) References Cited

U.S. PATENT DOCUMENTS 8,372,124 B2 * 2/2013 Paulk ................. A61B 17/0401 606/300
2009/0105761 A1 * 4/2009 Robie .................... A61B 90/06 606/86 A
2010/0185239 A1 * 7/2010 Patel .................. A61B 17/7071 606/264

* cited by examiner

*Primary Examiner* — Eduardo C Robert
*Assistant Examiner* — Michelle C Green

(57) ABSTRACT

A two-piece suspension pedicle anchor and its system and component-set is disclosed. The two-piece suspension pedicle anchor comprises a proximal piece and a distal piece that can rotate relatively. An external thread is arranged on the outer surface of the proximal piece, and a transverse through hole for an artificial ligament to pass through is arranged at the distal piece. As the two-piece suspension pedicle anchor is rotated and gradually locked into the bone, only the proximal piece is rotated, and the distal piece with the artificial ligament is pushed down but not rotated; in addition, the artificial ligament will be brought into the bone along with the distal piece and sandwiched between the outer surface of the proximal piece and the bone, that is, the artificial ligament will be sandwiched and fixed between the anchor-bone interface without wrapping around the outer surface of the proximal piece.

17 Claims, 44 Drawing Sheets

A-A section

B-B section

PEDICLE ANCHOR FOR USE IN TRANSLAMINAR PEDICLE ANCHOR SUSPENSION SYSTEM AND COMPONENT SET THEREOF

RELATED CASE

This is a continuation-in-part of co-pending Ser. No. 17/501,267 filed on Oct. 14, 2021, which is a continuation-in-part of Ser. No. 17/193,320 filed on Mar. 5, 2021 (now U.S. Pat. No. 11,172,964), whose disclosures are incorporated by this reference as though fully set forth herein.

BACKGROUND OF INVENTION

1. Field of the Invention

The invention refers to a translaminar pedicle anchor suspension system (referred as T-PAS system hereinafter), especially refers to a system and a pedicle anchor thereof that can be used to suspend a vertebral segment above from an adjacent segment below by means of a "pedicle anchor and artificial ligament" construct.

2. Description of the Prior Art

The human spine is composed of twenty-four vertebrae (including seven cervical vertebrae, twelve thoracic vertebrae and five lumbar vertebrae), one sacrum and one coccyx connected by ligaments, joints and intervertebral discs. When one of the vertebrae is displaced, slipped, deformed, degenerated or damaged due to diseases or trauma, it may cause pain or neurological symptoms as a result of advanced degeneration, instability or nerve compression.

Surgery is usually indicated whenever conservative treatment fails to relieve the symptoms of pain or neurologic deficit. Common surgical procedures may include: decompressive laminectomy, discectomy, fusion with or without instrumentation.

Current practice in spine surgery often requires the use of rigid spinal instrumentation to achieve immediate stability and to facilitate fusion. A typical conventional spinal fixator well-known in the art comprises the use of at least four pedicle screws and two connecting rods to stabilize the two adjacent vertebral segments, but the disadvantages of spinal instrumentation may include: 1. Nerve injury; 2. Increased bleeding; 3. Prolonged operative time; 4. Pedicle screw loosening; 5. Subsequent development of adjacent segment stenosis; 6. Loss of natural flexibility of spine; 7. Chronic back pain; 8. Bulky and protruding implant screw heads or rods may cause pain due to soft tissue impingement and bursitis.

Therefore, the present invention discloses the T-PAS system, which aims to reconstruct facet capsular ligaments with the use of a "pedicle anchor and suspension ligament" construct to dynamically stabilize the facet joints and to minimize the unwanted complications from the conventional instrumented fusion procedures.

SUMMARY OF THE INVENTION

The primary objective of the invention is to provide a two-piece suspension pedicle anchor for use in a translaminar pedicle anchor suspension system (T-PAS system) and a component-set thereof. The two-piece suspension pedicle anchor comprises a proximal piece and a distal piece that can rotate relatively. An external thread is arranged on the outer surface of the proximal piece, and a transverse through hole for an artificial ligament to pass through is arranged at the distal piece. As the two-piece suspension pedicle anchor is rotated and gradually locked into the bone, only the proximal piece is rotated, and the distal piece with the artificial ligament is pushed down but not rotated; in addition, the artificial ligament will be brought into the bone along with the distal piece and sandwiched between the outer surface of the proximal piece and the bone, that is, the artificial ligament will be sandwiched and fixed between the anchor-bone interface without wrapping around the outer surface of the proximal piece.

The procedure is easy and the suspension pedicle anchors are smaller and shorter compared with conventional instrumentation using "Pedicle screw and Rod" systems. The low profile of the T-PAS system and the ease of its application can obviously prevent complications of conventional pedicle screws which include excessive bleeding, nerve injury, screw loosening, and accelerated degeneration of adjacent segments.

In order to achieve the aforementioned objectives, the invention provides a two-piece suspension pedicle anchor, which comprises: an elongated columnar body extending along a central axis, an external thread arranged on an outer surface of the columnar body, a fitting structure arranged at a top end of the columnar body, and a through hole laterally penetrating through the columnar body. Wherein, the columnar body includes a proximal piece and a distal piece to present a two-piece columnar structure. The distal piece is assembled at a bottom end of the proximal piece, and the proximal piece is rotatable relative to the distal piece according to the central axis. The fitting structure is disposed on a top end of the proximal piece at a position away from of the distal piece. The external thread of the columnar body is disposed at least on an outer surface of the proximal piece. The through hole is disposed on the distal piece, and an extending direction of the through hole is not parallel to the central axis.

In a preferred embodiment, the bottom end of the proximal piece is provided with a central rod hole extending along the central axis toward the top end of the proximal piece. A top end of the distal piece is provided with a central rod protruding along the direction of the central axis. The size and position of the central rod correspond to the central rod hole, and the central rod is inserted into the central rod hole. The distal piece and the proximal piece can be assembled into the columnar body by inserting the central rod into the central rod hole. In addition, the proximal piece can rotate relative to the distal piece according to the central axis.

In a preferred embodiment, a rod top external thread is provided on a top of the central rod of the distal piece; in the central rod hole of the proximal piece, a rod hole internal thread that can engage with the rod top external thread is provided at a position relative to the rod top external thread. Wherein, the thread direction of the rod top external thread and the thread direction of the external thread of the columnar body are opposite.

In a preferred embodiment, a top end of the central rod of the distal piece can be pushed by a front end of a retractable thin push rod provided by a screwdriver. By extending the thin push rod of the screwdriver forward, the central rod and the distal piece can be pushed forward away from the proximal piece.

In a preferred embodiment, the extending direction of the through hole of the distal piece is perpendicular to the central axis. In addition, a U-shaped rod-holding rack is provided at the top end of the proximal piece of the columnar body.

In a preferred embodiment, the through hole allows an artificial ligament to pass through, so that the two-piece suspension pedicle anchor can be hung on the artificial ligament. The fitting structure can be connected with a screwdriver, such that, by operating the screwdriver, the two-piece suspension pedicle anchor is driven to rotate about the central axis, and the two-piece suspension pedicle anchor is adapted to be screwed and fixed to a bone, such that a portion of the artificial ligament is clamped and fixed between the outer surface of the proximal piece and the bone. In addition, when the screwdriver is operated to drive the two-piece suspension pedicle anchor to rotate about the central axis and gradually lock into the bone, only the proximal piece is driven and rotated by the screwdriver, and the distal piece is not be rotated by the screwdriver. Therefore, the artificial ligament passing through the through hole of the distal piece does not rotate nor wrap around the outer surface of the proximal piece.

In a preferred embodiment, the two-piece suspension pedicle anchor is for use in the T-PAS system. The T-PAS system is capable of being adapted to be installed in a spine having at least an upper vertebral segment and a lower vertebral segment. The T-PAS system comprising:

at least one said two-piece suspension pedicle anchor, capable of being adapted to be fixed to one of two pedicles of the lower vertebral segment; and at least one said artificial ligament, one end of the artificial ligament being fixed to the two-piece suspension pedicle anchor and thus adapted to be fixed to the pedicle of the lower vertebral segment, the other end of the artificial ligament being adapted to be connected to a contralateral side-surface of a lamina of the upper vertebral segment by a connecting structure; the artificial ligament configured to be tightened to a predetermined tension, such that the upper vertebral segment is able to be suspended by combination of the two-piece suspension pedicle anchor and the artificial ligament from the lower vertebral segment below.

In a preferred embodiment, wherein each of the upper vertebral segment and the lower vertebral segment respectively includes: said lamina and two said pedicles respectively located on left and right sides of the lamina. The lamina of the upper vertebral segment is adapted to be provided with a tunnel penetrating left and right side-surfaces of the lamina. Wherein the T-PAS system further comprises at least one washer which is adapted to be located near the tunnel of the lamina of the upper vertebral segment. A length of the washer is greater than a diameter of the tunnel. The connecting structure is configured to pass said the other end of the artificial ligament through the tunnel of the lamina of the upper vertebral segment and connect to the washer. The other end of the artificial ligament is connected to the washer and thus configured to be fixed at a location near the tunnel of the lamina of the upper vertebral segment when the predetermined tension is applied to the artificial ligament.

In a preferred embodiment, wherein the T-PAS system comprises two said two-piece suspension pedicle anchors configured to be received in the left and right pedicles of the lower vertebral segment. The T-PAS system comprises two said washers adapted to be respectively located at left and right ends of the tunnel of the lamina of the upper vertebral segment. The T-PAS system comprises first and second said artificial ligaments. Wherein one end of the first said artificial ligament is fixed to the two-piece suspension pedicle anchor configured to be located in the left pedicle, the other end of the first said artificial ligament is adapted to be passed through the tunnel from the left side-surface to the right side-surface of the lamina of the upper vertebral segment and connected to the washer configured to be located at the right side-surface of the laminar. Wherein one end of the second said artificial ligament is fixed to the two-piece suspension pedicle anchor configured to be located in the right pedicle, the other end of the second said artificial ligament is adapted to be passed through the tunnel from the right side-surface to the left side-surface of the lamina of the upper vertebral segment and connected to the washer configured to be located at the left side-surface of the laminar.

In a preferred embodiment, wherein the artificial ligament has two open ends and a middle section located between said two open ends. The middle section of the artificial ligament is configured to pass through the tunnel of the lamina of the upper vertebral segment to form a closed end at the middle section of the artificial ligament. The closed end of the artificial ligament is placed on a bar portion of the washer. Wherein, when a pulling force is applied from the open ends of the artificial ligament, the washer is adapted to press against the side-surface near the tunnel of the lamina of the upper vertebral segment, such that the closed end of the artificial ligament is fixed to the side-surface of the lamina of the upper vertebral segment by means of the washer.

In order to achieve the aforementioned objectives, the invention provides a component set for use in the T-PAS system. The T-PAS system is capable of being adapted to be installed in a spine having at least an upper vertebral segment and a lower vertebral segment. The component set comprising:

at least one said two-piece suspension pedicle anchor, capable of being adapted to be fixed to one of two pedicles of the lower vertebral segment;

at least one washer, which is adapted to be positioned at a lamina of the upper vertebral segment; and at least one artificial ligament, for connecting the two-piece suspension pedicle anchor and the washer; one end of the artificial ligament being fixed to the two-piece suspension pedicle anchor and thus adapted to be fixed to the pedicle of the lower vertebral segment, the other end of the artificial ligament being adapted to be connected to a contralateral side-surface of a lamina of the upper vertebral segment by means of the washer; wherein the artificial ligament is pre-assembled on the two-piece suspension pedicle anchor;

wherein the two-piece suspension pedicle anchor comprises:

an elongated columnar body extending along a central axis;

an external thread arranged on an outer surface of the columnar body;

a fitting structure arranged at a top end of the columnar body;

and a through hole laterally penetrating through the columnar body;

wherein:

the columnar body includes a proximal piece and a distal piece to present a two-piece columnar structure; the distal piece is assembled at a bottom end of the proximal piece, and the proximal piece is rotatable relative to the distal piece according to the central axis; the fitting structure is disposed on a top end of the proximal piece at a position away from of the distal piece; the external thread of the columnar body is disposed at least on an outer surface of the proximal piece;

the through hole is disposed on the distal piece, and an extending direction of the through hole is not parallel to the central axis;

the through hole allows the artificial ligament to pass through, so that the two-piece suspension pedicle anchor can be hung on the artificial ligament; the fitting structure can be connected with a screwdriver, such that, by operating the screwdriver, the two-piece suspension pedicle anchor is driven to rotate about the central axis, and the two-piece suspension pedicle anchor is adapted to be screwed and fixed to the pedicle, such that a portion of the artificial ligament is adapted to be clamped and fixed between the outer surface of the proximal piece and the pedicle; in addition, when the screwdriver is operated to drive the two-piece suspension pedicle anchor to rotate about the central axis, only the proximal piece is driven and rotated by the screwdriver, and the distal piece is not be rotated by the screwdriver; therefore, the artificial ligament passing through the through hole of the distal piece does not rotate nor wrap around the outer surface of the proximal piece.

In a preferred embodiment, the component set further comprises a screwdriver. Wherein the screwdriver comprises:

a handle;

a long-rod portion, extending a predetermined length from one end of the handle along an axis;

a driver head, located at an end of the long-rod portion away from the handle; a structure of the driver head being corresponding to and connectable with the fitting structure of the two-piece suspension pedicle anchor, such that, when the handle rotates, the driver head drives the proximal piece of the two-piece suspension pedicle anchor to rotate; and two hangers, assembled on the handle or the long-rod portion in a detachable manner; the two hangers can be respectively wound around a closed end and an open end of the artificial ligament extending from the through hole of the two-piece suspension pedicle anchor; by detaching the two hangers from the handle, the closed end and the open end of the artificial ligament can be removed directly and quickly from the screwdriver.

In a preferred embodiment, wherein a hollow tube is formed in the center of the handle and the long-rod portion, and a thin push rod is arranged in the hollow tube in a retractable manner. A rear end of the thin push rod is combined with an adjustment module. The adjustment module includes a pusher and a locking teeth groove. The pusher is engaged with teeth of the locking teeth groove by an elastic member. Pushing the pusher by external force can make the pusher to move forward and backward along the locking teeth groove. When the external force disappears, the teeth of the locking teeth groove can provide a positioning effect to the pusher. The rear end of the thin push rod is combined with the pusher. When the pusher is pushed to move forward along the locking teeth groove, the thin push rod will also be driven by the pusher to extend forward and protrude out of the driver head of the screwdriver. When the pusher is pushed to move backward along the locking teeth groove, the thin push rod will be driven by the pusher to retract backward. A ruler scale is set on a side of the locking teeth groove for a user to know how far the thin push rod is pushed out. The distal piece can be pushed by a front end of the retractable thin push rod of the screwdriver. By extending the thin push rod of the screwdriver forward, the distal piece can be pushed forward away from the proximal piece.

BRIEF DESCRIPTION OF THE DRAWINGS

The present invention will now be specified with reference to its preferred embodiment illustrated in the drawings, in which.

DESCRIPTION OF THE PREFERRED EMBODIMENT

Figure 1A:
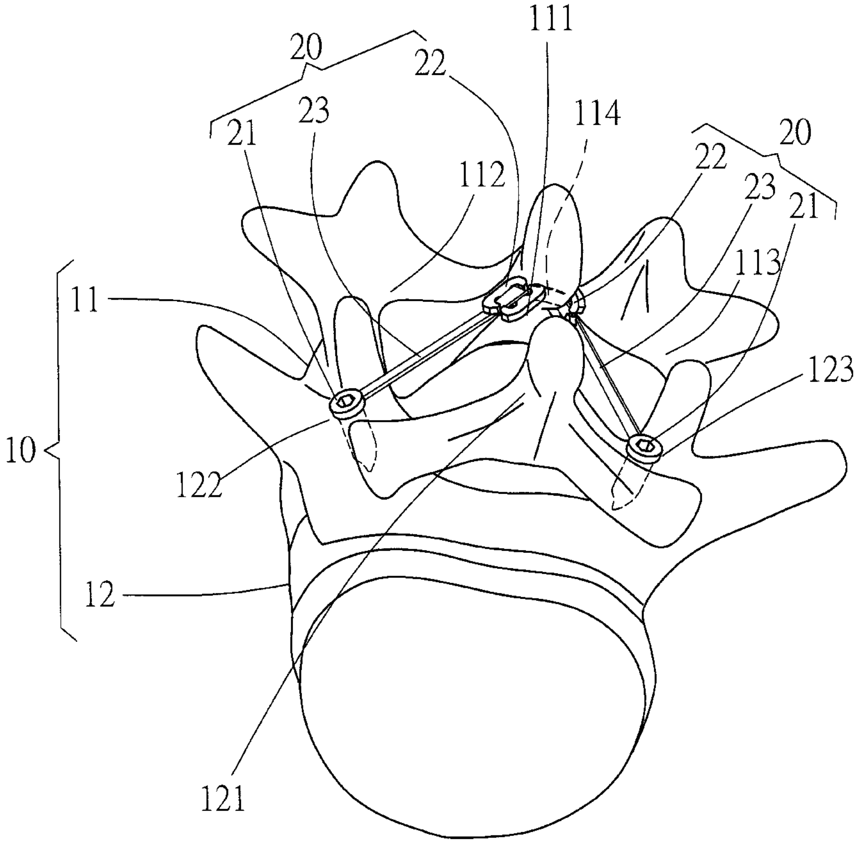
FIG. 1A and FIG. 1B respectively are the first perspective three-dimensional (3D) schematic diagram and the second perspective 3D schematic diagram of an embodiment of the T-PAS system of the present invention furnished on two adjacent vertebral segments.
Figure 1B:
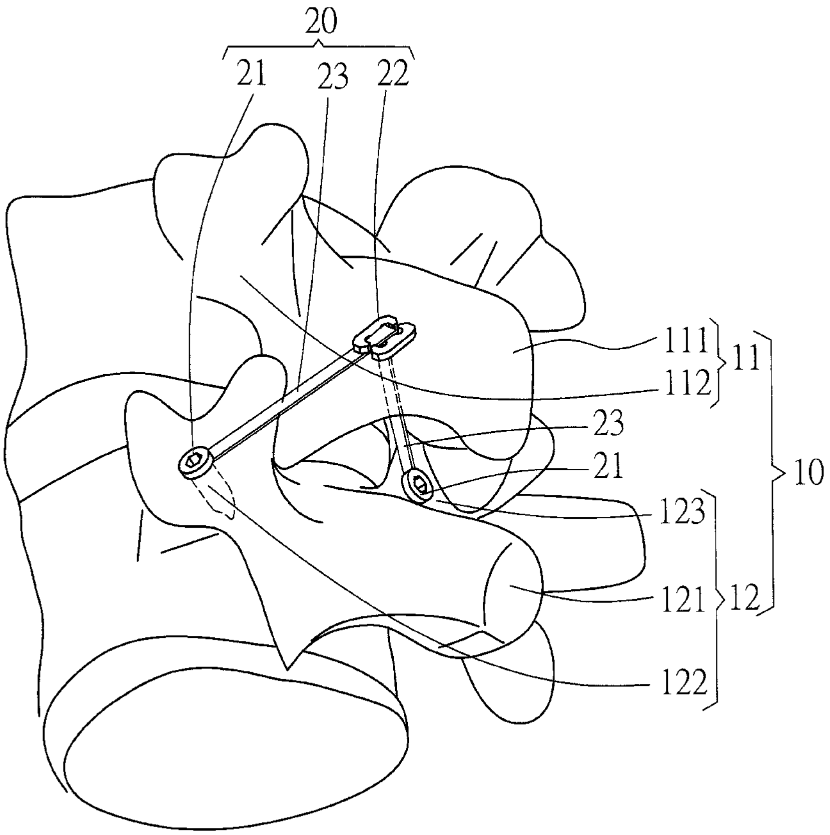
Figure 2B:
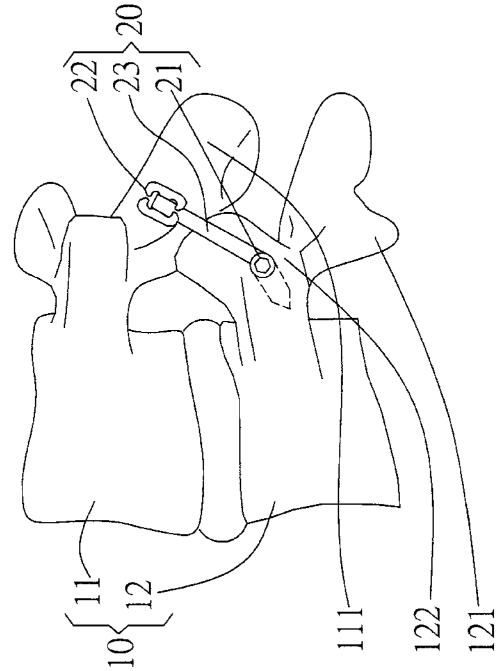
FIG. 2A and FIG. 2B respectively are the top-view schematic diagram and the left-side-view schematic diagram of an embodiment of the T-PAS system of the present invention furnished on two adjacent vertebral segments.
Figure 2A:
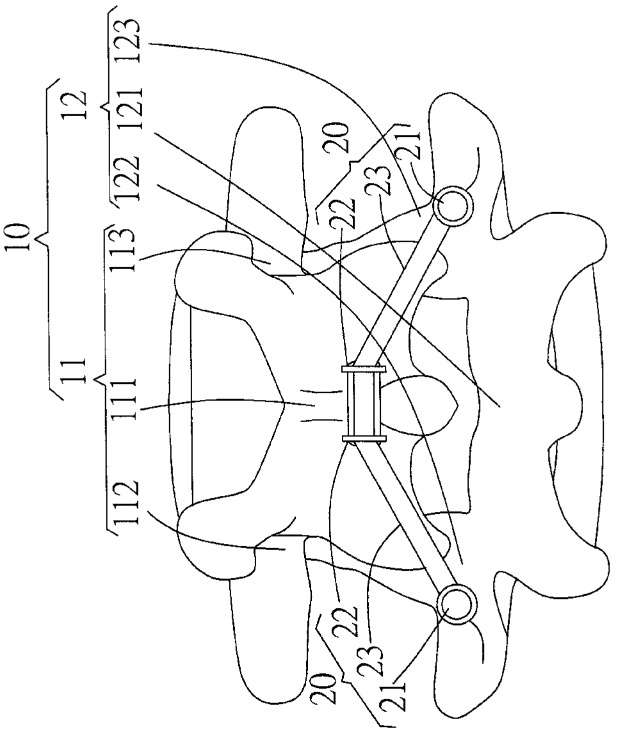

The present invention refers to a translaminar pedicle anchor suspension system (referred as T-PAS system) applicable to vertebral surgeries. The T-PAS system comprises: at least one pedicle anchor capable of being fixed to a pedicle of a lower vertebral segment, at least one suspension ligament having one end thereof fixed to the pedicle anchor, and at least one washer capable of fixing the other end of the suspension ligament to a contralateral side of a lamina of an upper vertebral segment. The suspension ligament is tightened to a predetermined tension, and the upper vertebral segments are suspended by the suspension ligament to a segment below. By using the suspension ligament to suspend the upper vertebral segment via a tunnel drilled on the lamina, not only can the spine be dynamically stabilized, but also the use of traditional pedicle screws and bone fusion can be avoided. This novel T-PAS system has the following advantages: (1) reduce operation time; (2) reduce the risk of nerve damage; (3) reduce bleeding; (4) maintain vertebral mobility; (5) patients would feel more natural without stiffness in the lower back after surgery; and (6) it can theoretically avoid the accelerated degeneration of adjacent segments caused by internal fixation and fusion, which is not an uncommon complication after conventional instrumented fusion. The indications and scopes of application of the T-PAS system of the present invention include (but are not limited to): single or multiple joint stenosis, lumbar spine stenosis, lumbar spondylolisthesis, and etc. The T-PAS system of the present invention can be applied to the patient's first primary surgery after decompressive surgery, or it can be used in the subsequent treatment of junctional stenosis without having to remove the instrumentation.

In the T-PAS system of the present invention, a loop of artificial ligament (suspension ligament) was pulled to the contralateral side of lamina through a transverse tunnel created through a rigid point of the arch of lamina, and a pig-nose washer was used to cinch the suspension ligament on the contralateral wall of lamina of the upper segment. The loop of suspension ligament was pulled to stabilize the pig-nose washer on the contralateral wall of the lamina, and the suspension ligament was subsequently tightened by a pedicle anchor, which located at the adjacent segment below, to achieve optimal tension of the ligament. Such procedure is easy and also the suspension pedicle anchors are smaller and shorter compared with conventional instrumentation using "Pedicle screw and Rod" systems. The low profile of the system and the ease of its application can obviously prevent complications of conventional pedicle screws which include excessive bleeding, nerve injury, screw loosening, and accelerated degeneration of adjacent segments.

The following descriptions provide some fundamental illustrations for the Key words, Instruments, Indications, Benefits, and Surgical Techniques regarding to the T-PAS system of the present invention. cl Key Words 1. (T-PAS) Translaminar Pedicle Anchor Suspension: A surgical procedure where dynamic stabilization is provided for two adjacent lumbar segments, and it is performed with anchors in the pedicles and a suspension ligament passed through a laminar tunnel.
2. Suspension Pedicle Anchor (SPA): Threaded Screws with offset or level eyelets containing Suspension ligaments (SL). Sizes: (4.5×25 mm) (5×30 mm)
3. Suspension Ligament (SL): 2-3 mm diameter material threaded through the eyelets of the Pedicle Anchor.
4. Laminar Pig-Nose Washer (LPNW) with Slots on both sides: (Single-central column, Double-central column)
5. Laminar Banana Washer: (Unilateral procedures and Endoscopic procedure of spine)
6. Suspension Abutment Pedicle Anchor (SAPA): A Pedicle Anchor that is placed adjacent to an existing Pedicle Screw. That is, the SAPA is shaped like a SPA with shorter length and smaller diameter for ASD in which the instrumentation from primary surgery is left unremoved.

7. Headed Suspension Pedicle Anchor (HSPA): A fixed or polyaxial headed Pedicle Anchor with eyelets to pass a (SL) through and attachment on the top for a fusion rod.

Instruments

1. Pedicle Anchor Driver: Used to insert the anchor with offset Suspension Ligament hangers.
2. Suspension Ligament Off-Set Passer: To pull the SL through the Laminar Tunnel.
(Optional: Curved needle or Wire Passer to pull the SL through the Laminar Tunnel)
3. Off-Set Burr Hole Tap: To enlarge and smooth the drill hole.
4. Laminar Drill Guide: To create the Laminar Tunnel for the Suspension Ligament.
(Optional: Use an angled burr or straight burr with 2 mm burr head)
5. Ligament tension gauge: To assess the tension of the SL.

1. Indications

A. Primary indications
B. Extended indications

A. Primary indications

1. Degenerative Lumbar Spine Stenosis: Single or multi-level, with or without disc herniation.
2. Degenerative Spondylolisthesis: Single or multiple motion segments.
3. Discectomy that Destabilizes a Facet Joint: Instability created during discectomy and decompression.
4. Discectomy with a Preexisting Instability: Known instability at the level of a disc herniation.
(i.e. Spondylolisthesis or instability detected on flexion & extension films)

B. Extended indications

1. Prevention of Junctional Stenosis: Using a "Headed Suspension Pedicle Anchor" (HSPA) as the upper screws of an instrumented fusion construct in primary surgery, to create a dynamically stabilize junctional segment above.
2. Treatment of Junctional Stenosis Above an Instrumented Fusion: Using a "Suspension Abutment Pedicle Anchor" (SAPA) technique to preserve the instrumented fusion construct in revision surgery while dynamically stabilizing the segment above the fusion.

2. Benefits of Intersegmental Suspension Technique

1. Preserves motion of the lumbar spine, theoretically reducing or preventing the accelerated junctional degeneration of adjacent segments, which is not uncommon in instrumented fusion technique.
2. Prevents the unwanted discomfort from instrumented fusion, including chronic back pain, stiffness, loosening of screws, and nerve injury.
3. Reduces incidence of nerve injury or blood transfusion because of the small sized Pedicle Anchor, and the ease of application with the T-PAS technique.
4. Less epidural manipulation and less bleeding from epidural vessels, in contrast to interbody cage placement with an instrumented fusion.

3. Surgical Techniques: A, B and Extended Indication Technique

Technique A: "Off-Set Eyelet" Pedicle Anchor

1. With the patient prone on a spine frame under general anesthesia, an incision is made to expose the L4 and L5 laminae and bilateral L4/5 facets with care to protect the midline ligamentous structures.
2. A planned and limited laminotomy is performed. This includes excision of part of the thickened laminae of the lower part of L4 and the upper part of L5, the hypertrophic ligamentum flavum, and the medial portion of the L4/5 facet (medial edge of superior facet) to decompress the L5 nerve roots bilaterally. The midline ligamentous structures are carefully preserved, including the supraspinous and interspinous ligaments.
The outer border of L4/5 facets were defined by cautery, and the orientation of the superior facet and pedicle are identified. The midline ligamentous structures are carefully preserved, including the supraspinous and interspinous ligaments.
3. A Pedicle Anchor (PA), which is 30 mm long with a diameter of 4.5 mm and pre-threaded with a 2 mm Suspension Ligament (SL), is placed into the L5 pedicle in usual manner. This anchor will be buried to the first eyelet level in the anchor (which is 10 mm below the screw top) to achieve the "FIRST INTERFACE FIXATION" of the Suspension Ligament.
4. A 2 mm diameter "Laminar Tunnel" is created through the K-point ("Kenyoh Point") with a 2 mm burr head and the tunnel is then smoothed and slightly widened with Burr hole tap to facilitate passage of the Suspension Ligament across the tunnel.
"K-Point": Located at the intersection of the spinous process in the sagittal plane, and the lamina in the coronal plane. The K-point is located at the rigid part of the base of lamina which is usually the junction of superior ¼ and middle ⅓ of the arch of the lamina.
5. A 2 mm diameter burr head is used to create the laminar tunnel hole at the "K-Point" to pass the Suspension Ligament through the bone tunnel. The tunnel is smoothed and slightly enlarged with an "Off-Set Laminar Drill-Hole Tap". (Steps 4 and 5 repeated) . . . .
6. The Suspension Ligament Passer (or use a round bodied suture needle) is now used to pull the Suspension Ligament as a loop, through the "Laminar Tunnel" to the contralateral side. The free end of Suspension Ligament remains on the Suspension Pedicle Anchor side.
7. A "Laminar Pig-Nose Washer" (LPNW) is used to secure the loop of the Suspension Ligament on the contralateral side of the lamina. The loop of the Suspension Ligament is placed into both slots of LPNW and then the free end of the Suspension Ligament is pulled tight cinching the LPNW against the opposite side lamina.
8. The returning free end of the Suspension ligament (SL) is brought under and below the first strand. Particularly, an extra length of the SL was pulled up according to the estimated length of the SL and the diameter of the screw before tightening down the SPA before the upper eyelet was buried below the bone surface. The SL is then pulled and tensioned while the pedicle anchor is then tightened down, so the second eyelet, which is 5 mm above the lower eyelet and is 5 mm below the top of anchor, is buried below the bone surface to achieve a "SECOND INTERFACE FIXATION" of the SL.

This locks both ends of the SL between the anchor and the bone.

9. The tension of the SL can now be measured with a tension gauge or evaluated with the surgeon's finger by palpation. If more tension is required, the PA can further be tightened downward after both ends of SL are cut.

10. The same procedure is repeated on the contralateral side when bilateral suspension is indicated.

11. The translaminar pedicle ligament suspension procedure of is then completed, and the wound is closed in the usual manner with or without drains.

Postoperative Care

Patients are advised to use a soft lumbar corset is for 4-6 weeks, and motion of lumbar spine is not restricted.

Technique B: "Level Eyelet" Pedicle Anchor

1. With the patient prone on a spine frame under general anesthesia, an incision is made to expose the L4 and L5 laminae and bilateral L4/5 facets with care to protect the midline ligamentous structures.

2. A planned and limited laminotomy is performed. This includes excision of part of the thickened laminae of the lower part of L4 and the upper part of L5, the hypertrophic ligamentum flavum, and the medial portion of the L4/5 facet (medial edge of superior facet) to decompress the L5 nerve roots bilaterally.

The outer border of L4/5 facets were defined by cautery, and the orientation of the superior facet and pedicle are identified. The midline ligamentous structures are carefully preserved, including the supraspinous and interspinous ligaments.

3. A Suspension Pedicle Anchor (SPA), which is 30 mm long with a diameter of 5 mm and pre-threaded with a 2 mm Suspension Ligament (SL), is placed into the L5 pedicle in usual manner. The level eyelets which are 5 mm below the top of the screw are left exposed above the bony surface of the pedicle.

4. A 2 mm diameter "Laminar Tunnel" is created through the K-point ("Kenyoh Point") with a 2 mm burr head to create a hole to pass the Suspension Ligament across.

"K-Point": Located at the arch of laminate which is "at the intersection of the spinous process in the sagittal plane, and the lamina in the coronal plane". It is usually located at the junction of superior ⅓ and middle ⅓ of the arch of the lamina in the thin section of the bone.

5. The Laminar Tunnel is smoothed and slightly enlarged with an "Off-Set Laminar Drill-Hole Tap". A 2 mm diameter burr head is used to create the laminar tunnel hole at the "K-Point" to pass the Suspension Ligament through the bone tunnel.

6. The Suspension Ligament Passer (or a round bodied suture needle) is now used to pull a loop of the Suspension Ligament through the "Laminar Tunnel" to the contralateral side. The free ends of Suspension Ligament remain on the Pedicle Anchor side.

7. A "Laminar Pig-Nose Washer" (LPNW) is used to secure the loop of the Suspension Ligament on the contralateral side of the lamina. The two strands of the loop of the Suspension Ligament are placed around each slot of LPNW. And then, the free end of the Suspension Ligament on the pedicle anchor side is brought under and below the first strand. Both strands of the SL are then pulled tightly tensioning the construct 8. With the tension maintained on both free ends of SL, the returning end is passed under the Suspension Ligament on the ipsilateral side of the anchor. The appropriate tension is applied as the pedicle anchor is then tightened down with both eyelets secured under bone creating an interface fixation. The Suspension Ligament is secured on the contralateral side of the lamina by the LPNW.

9. The Pedicle Anchor can be driven further down when additional tension is required.

10. The same procedure is repeated on the contralateral side to achieve bilateral Pedicle Anchor suspension.

11. The translaminar pedicle ligament suspension procedure is then completed, and the wound is closed in the usual manner with or without drains.

Postoperative Care

Patients are advised to use a soft lumbar corset is for 4-6 weeks, and motion of lumbar spine is not restricted.

B. Extended Indication Techniques

Dynamic Stabilization of Adjacent Segments of a Rigid Lumbar Fusion

Providing Prevention and Treatment of "Adjacent Segment Degeneration" (ASD)

1. PREVENTION OF A.S.D.: Use a Headed Suspension Pedicle Anchor (HSPA). This screw will accommodate the rod for the fusion to the lower segment and provide an eyelet with the Suspension Ligament to dynamically stabilize the segment above the fusion, using technique of A or B.

2. TREATMENT OF A.S.D.: Use a Suspension Abutment Pedicle Anchor (SAPA) placed in the same Pedicle where the upper pedicle screw is located in an instrumented fusion construct that has progressive disease in the level above the fusion. The SAPA is placed adjacent to the current pedicle screw through the technique of Cortical Bone Trajectory or from Superiorly as long as the SAPA can be securely anchored. Once an SAPA is placed securely in the pedicle with instrumented fusion, the T-PAS Procedure can then be repeated for the Adjacent Segment as described using technique A or B.

In order to more clearly illustrate the T-PAS system and its pedicle anchors and component-set proposed by the present invention, the following embodiments will be described in detail with the drawings.

Please refer to FIG. 1A, FIG. 1B, FIG. 2A and FIG. 2B, which respectively are the first perspective three-dimensional (3D) schematic diagram, the second perspective 3D schematic diagram, the top-view schematic diagram, and the left-side-view schematic diagram of an embodiment of the T-PAS system of the present invention furnished on two adjacent vertebral segments.

The translaminar pedicle anchor suspension system (referred as T-PAS system) of the present invention can be installed on a spine 10 having at least an upper vertebral segment 11 and a lower vertebral segment 12. Each of the upper vertebral segment 11 and the lower vertebral segment 12 respectively includes: a lamina 111, 121 and two pedicles 112, 113, 122, 123 which are respectively located on the left and right sides of the lamina 111, 121. In this embodiment, the T-PAS system 20 is installed on the L4 and L5 vertebrae of the lumbar spine of the spine 10 as an example for description, however, it can also be installed on vertebrae at different positions, or used to connect and suspend a larger number of vertebrae (such as three or more layers of vertebrae).

As shown in FIG. 1A, FIG. 1B, FIG. 2A and FIG. 2B, the T-PAS system 20 of the invention comprises: at least one pedicle anchor 21, at least one washer 22 and at least one suspension ligament 23. The pedicle anchor 21 is capable of being fixed to one of the pedicles 122 of the lower vertebral segment 12. The washer 22 is located near a side-surface of the lamina 111 of the upper vertebral segment 11; particularly, the washer 22 is preferably located at a location of the lamina 111 with the greatest strength or thickness. In an embodiment of the present invention, one end of the suspension ligament 23 is connected to a contralateral side-surface of the lamina 111 of the upper vertebral segment 11 by means of the washer 22. The suspension ligament 23 is connected between the pedicle anchor 21 and the washer 22, and is thus fixed to the pedicle 122 of the lower vertebral segment 12 and the lamina 111 of the upper vertebral segment 11 by means of the pedicle anchor 21 and the washer 22, respectively. In addition, the suspension ligament 23 is tightened to a predetermined tension, and the upper vertebral segment 11 is suspended by combination of the pedicle anchor 21 and the suspension ligament 23 from the lower vertebral segment 12 below.

In this embodiment, the lamina 111 of the upper vertebral segment 11 is provided with a transverse tunnel 114 penetrating the left and right side-surfaces of the lamina 111. Preferably, the tunnel 114 is formed in a relatively thicker or stronger portion of the lamina 111. The number of the pedicle anchors 21 is two, which are respectively arranged at the two pedicles 122 and 123 of the lower vertebral segment 12. The number of the washers 22 is two, which are respectively located at the left and right ends of the tunnel 114 of the lamina 111 of the upper vertebral segment 11. The number of the suspension ligaments 23 is two; in which, one end of one of the suspension ligaments 23 is fixed to the pedicle anchor 21 located in the left pedicle 122, while the other end of the same suspension ligament 23 is first passed through the tunnel 114 from the left side-surface to the right side-surface of the lamina 111 of the upper vertebral segment 11 and then connected to the washer 22 located at the right side-surface of the lamina 111; on the other side, one end of the other suspension ligament 23 is fixed to the pedicle anchor 21 located in the right pedicle 123, while the other end of this suspension ligament 23 is first passed through the tunnel 114 from the right side-surface to the left side-surface of the lamina 111 of the upper vertebral segment 11 and then connected to the washer 22 located at the left side-surface of the lamina 111.

In a preferred embodiment, the transverse tunnel 114 is created with a 2 mm burr head through a point which is usually located between the upper ¼ to ⅓ of the roof of the lamina 111. The tunnel 114 allows passage of suspension ligaments 23 from both sides to be tightened by suspension pedicle anchors 21 from a segment 12 below. An optimal tension can be achieved as the pedicle anchor 21 is placed further down, the optimal tension can be measured by a tension gauge or felt by the finger of a surgeon. The optimal tension is defined by observing the movement of facet joints of less than 1 mm when the base of lamina 111 of the upper segment 11 was pulled and tested with a towel clip.

In an embodiment, the T-PAS system 20 of the present invention further includes a hollow sleeve 24 plugged in the tunnel 114, and both the suspension ligaments 23 pass through the sleeve 24. Or alternatively, the sleeve 24 may not be provided, but a conventional file or a hand-held file 96 (i.e., Off-Set Burr Hole Tap; see FIG. 15) of the present invention may be used to smooth the inner surface and the edges of both ends of the tunnel 114 on the lamina 111, in order to avoid the sharp edges or rough inner surface of the tunnel 114 of the lamina 111 from cutting the suspension ligament 23, or avoid the edges of the tunnel 114 from being broken due to the high tension and friction of the suspension ligament 23.

In this embodiment, the suspension ligament 23 is artificial ligament; the pedicle anchor 21 is a pedicle screw having external threads; and the washer 22 has a length greater than the diameter (or width) of the tunnel 114, such that the washer 22 can press against the outer side-surface of the tunnel 114 of the lamina 111 and will not fall into the tunnel 114 due to the tension of the suspension ligament 23. The materials of the pedicle anchor 21 and the washer 22 can be made of titanium alloy, or ceramic, or other materials that will not cause allergies or rejection to human body.

Please refer to FIGS. 3A to 3E, which are schematic diagrams respectively showing the steps for installing the T-PAS system of the present invention onto two adjacent vertebral segments.

Figures 3A, 3B, 3C, 3D, 3E:
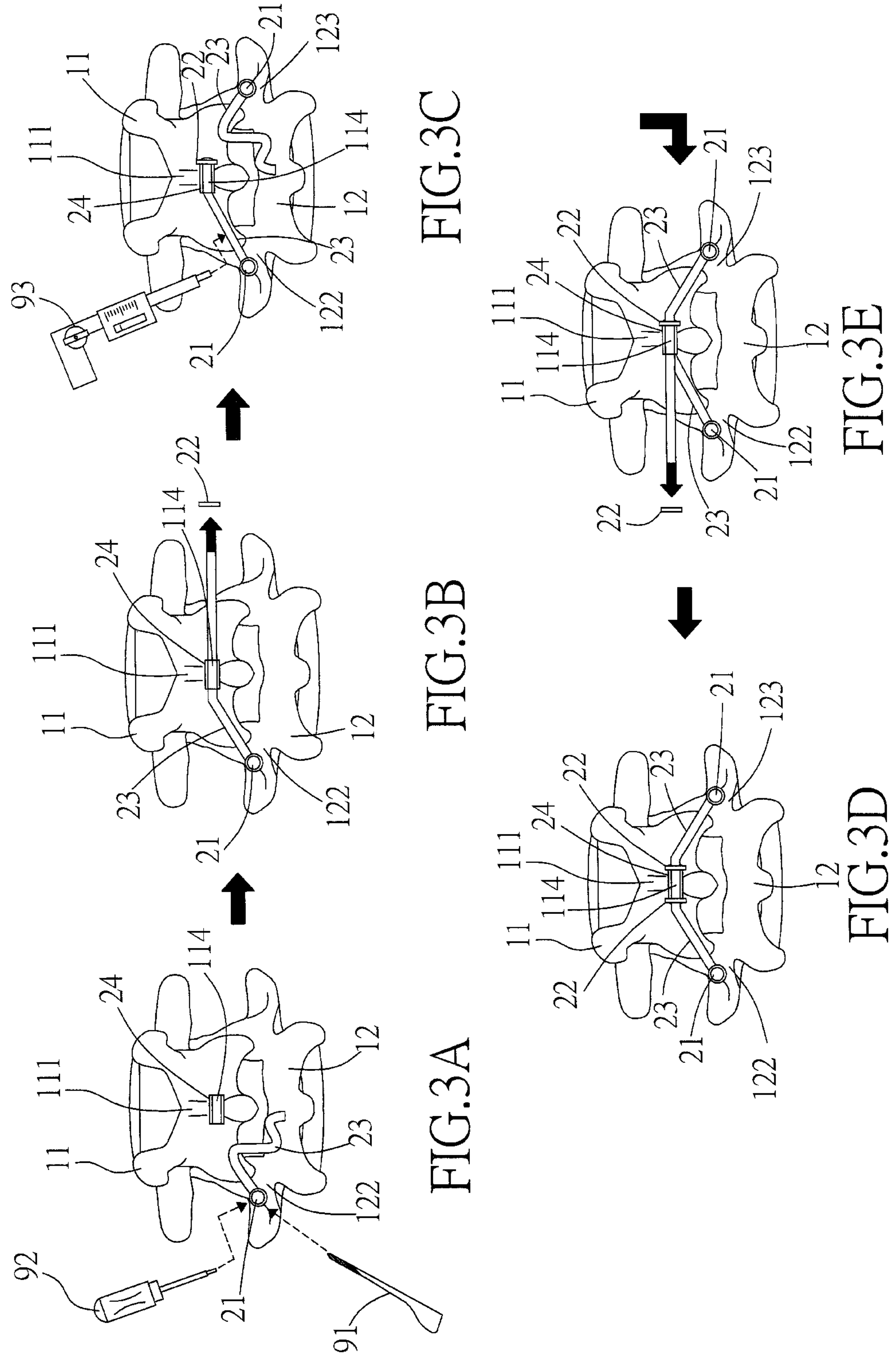
FIGS. 3A to 3E are schematic diagrams respectively showing the steps for installing the T-PAS system of the present invention onto two adjacent vertebral segments.

As shown in FIG. 3A, when the T-PAS system 20 of the present invention is to be installed on two adjacent vertebral segments 11 and 12, a drilling tool 91 is first used to drill a small hole of a predetermined depth in the left pedicle 122 of the lower vertebral segment 12. Then, use a screwdriver 92 (i.e., Pedicle Anchor Driver) to screw and fix the pedicle anchor 21 into the small hole at the pedicle 122, wherein the pedicle anchor 21 is pre-assembled with the suspension ligament 23. At this moment, the suspension ligament 23 connected to the pedicle anchor 21 has no tension and is in a loosened state. And then, as shown in FIG. 3B, the end of the suspension ligament 23 away from the pedicle anchor 21 is moved to pass through the tunnel 114 (or sleeve 24) from the left side-surface to the right side-surface of the lamina 111 of the upper vertebral segment 11, and then is assembled and connected to the washer 22 located at the right side-surface of the lamina 111. At this time, the washer 22 has not yet abutted against the right side-surface of the lamina 111, and the suspension ligament 23 connected between the pedicle anchor 21 and the washer 22 is still in a loosened state. Next, as shown in FIG. 3C, by pulling the suspension ligament 23 from the left side of the lamina 111 toward the left, the washer 22 abuts against the right side-surface of the lamina 111 of the upper vertebral segment 11, and the, after measuring the tension of the suspension ligament 23 with a tension gauge 93 to reach a predetermined tension value, the end of the suspension ligament 23 is fixed and the excess suspension ligament 23 is removed (e.g., cut with scissors). And then, the same steps illustrated in FIG. 3A to FIG. 3C are repeated for installing another set of pedicle anchor, washer and suspension ligament; as shown in FIG. 3C, FIG. 3D and FIG. 3E, the right pedicle 123 of the lower vertebral segment 12 is also screwed with a pedicle anchor 21 which is pre-assembled with a suspension ligament 23 (as shown in FIG. 3C). Then, an end of the suspension ligament 23 is also first passing through the tunnel 114 (or sleeve 24) from the right side-surface to the left side-surface of the lamina 111 of the upper vertebral segment 11 and then connected to the washer 22 located at the left side-surface of the lamina 111 (see FIG. 3D). And then, after the suspension ligament 23 is pulled to reach the predetermined tension value, the end of the suspension ligament 23 is fixed and the excess suspension ligament 23 is removed (as shown in FIG. 3E). With these steps of installing procedure, the installation of the T-PAS system 20 of the present invention can be completed for suspending the upper vertebral segment 11 from the lower vertebral segment 12 below via the combination of the pedicle anchor 21 and the suspension ligament 23. The T-PAS system 20 of the present invention can suspend the upper vertebral segment from the lower vertebral segment through suspension ligaments; it not only can stabilize the structural strength of the spine, but also can reduce the number of pedicle anchors (pedicle screws) required for surgery, shorten the operation time, reduce the risk of nerve injury, reduce bleeding, maintain postoperative vertebral mobility, avoid accelerated degeneration of adjacent segments caused by internal fixation and fusion, reduce post-operative discomfort, ache and stiffness of patient's back, and accelerate the patient's recovery time after the vertebral surgery.

In the aforementioned embodiment, the installation of the pedicle anchor 21 and the suspension ligament 23 on one side (left side) is completed first, and then the steps for installing the other pedicle anchor 21 and the other suspension ligament 23 on the other side (right side) are started. However, in another embodiment of the present invention, the pedicle anchors 21 and suspension ligaments 23 on both sides can also be installed simultaneously. Specifically speaking, the two pedicle anchors 21 located on the left and right pedicles 122 and 123 of the lower vertebral segment 12 can be screwed and fixed to the left and right pedicles 122 and 123 respectively in the same step shown in FIG. 3A; then, the two suspension ligaments 23 connected to the two pedicle anchors 21 are respectively and sequentially having one end thereof passing through the tunnel 114 (or sleeve 24) and extending out of the other side of the lamina 111 of the upper vertebral segment 11 in the step illustrated in FIG. 3B, and then the ends of the two suspension ligaments 23 are respectively assembled with a corresponding washer 22. And then, by pulling the two suspension ligaments 23 separately and sequentially, the two washers 22 are respectively pressed against the two opposite side-surfaces of the lamina 111 of the upper vertebral segment 11; and then, after measuring the tensions of these two suspension ligaments 23 with a tension gauge 93 to reach a predetermined tension value, the ends of these two suspension ligaments 23 are fixed and the excess suspension ligaments 23 are removed as shown in FIG. 3E; such procedure can also complete the installation of the T-PAS system 20 of the present invention in order to suspend the upper vertebral segment 11 from the lower vertebral segment 12 below by using the suspension ligaments 23, washers 22 and pedicle anchors 21.

Figure 4A:
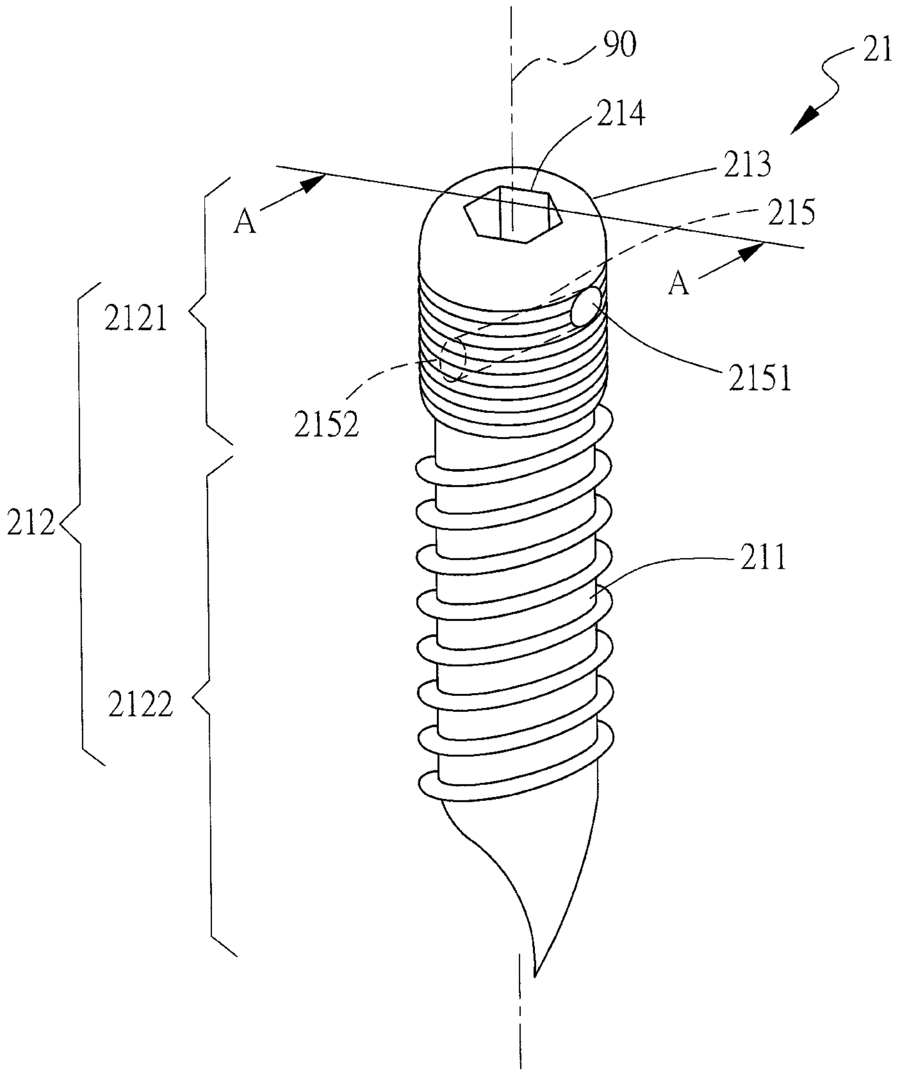
FIG. 4A and FIG. 4B respectively are a three-dimensional (3D) schematic diagram and an A-A cross-sectional schematic view of an embodiment of the pedicle anchor in the T-PAS system of the present invention.
Figure 4B:
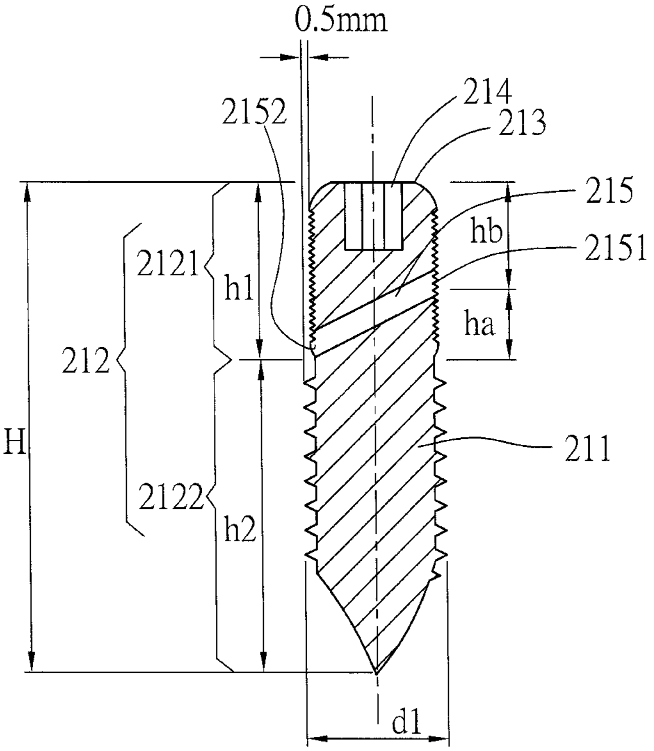

Please refer to FIG. 4A and FIG. 4B, which are respectively a three-dimensional (3D) schematic diagram and an A-A cross-sectional schematic view of an embodiment of the pedicle anchor in the T-PAS system of the present invention. In this embodiment, the pedicle anchor 21 has an elongated and narrow columnar body 211 extending along a central axis 90, an external thread 212 arranged on the outer surface of the columnar body 211, a fitting structure 214 arranged at a top end 213 of the columnar body 211, and an oblique through hole 215 penetrating through the columnar body 211. Wherein, the oblique through hole 215 is not parallel to the central axis; the oblique through hole 215 passes through the central axis 90; the openings at two ends of the through hole 215 are respectively called the upper opening 2151 and the lower opening 2152. The distance "hb" between the upper opening 2151 and the top end 213 of the columnar body 211 is smaller than the distance "ha+hb" between the lower opening 2152 and the top end 213 of the columnar body 211. In other words, the distance between the upper and lower openings 2151 and 2152 along the direction of the central axis 90 is "ha". The oblique through hole 215 allows the suspension ligament 23 to pass through, so that the pedicle anchor 21 is hung on the suspension ligament 23. The fitting structure 214 can be connected with the front end of the screwdriver 92, such that, by operating the screwdriver 92, the pedicle anchor 21 is driven to rotate about the central axis 90, and the pedicle anchor 21 can be screwed and fixed to the pedicle 122. In this embodiment, the fitting structure 214 is a hexagonal recess, whose contour and size are corresponding to the hexagonal post on the front end of the screwdriver 92. The external thread 212 provided on the outer surface of the columnar body 211 of the pedicle anchor 21 includes a smaller-pitched threaded portion 2121 and a larger-pitched threaded portion 2122. The smaller-pitched threaded portion 2121 is disposed closer to the top end 213 of the columnar body 211, and has a relatively lower thread height and smaller thread pitch. The larger-pitched threaded portion 2122 is disposed away from the top end 213 of the columnar body 211, and has a relatively higher thread height and larger thread pitch. In addition, the upper opening 2151 and the lower opening 2152 are both located closer to the top end 213 of the columnar body 211, so the two openings 2151 and 2152 are both located at the smaller-pitched thread portion 2121. In the present invention, several pedicle anchors 21 of different sizes and specifications can be produced in advance in order to adapt to different vertebrae sizes or structures of different patients. Generally speaking, for the pedicle anchors 21 used in the T-PAS system 20 of the present invention, as shown in FIG. 4B, the outer diameter "dl" of the columnar body 211 is between 3.5 mm-7.5 mm, and the total length "H" is between 20 mm-35 mm. In this embodiment, the distance "hb" between the upper opening 2151 and the top end 213 of the columnar body 211 is between 3 mm-7 mm, the distance "ha" between the two openings 2151 and 2152 in the direction of the central axis 90 is between 2 mm-4 mm, the height "h1" of the smaller-pitched thread portion 2121 can be between 5 mm-11 mm, and the height "h2" of the larger-pitched thread portion 2122 can be between 14 mm-30 mm.

In the embodiment shown in FIG. 4A and FIG. 4B, there are two reasons for the external thread 212 of the pedicle anchor 21 to be designed to include a smaller-pitched thread portion 2121 adjacent to the top end 213 of the columnar body 211 and a larger-pitched thread portion 2122 far from the top end 213: (1) the hardness and density of the bone at the pedicle 122 is relatively high near the surface, while the hardness and density of the bone deep inside is relatively low; (2) when the pedicle anchor 21 is screwed into the pedicle 122, the area above the lower opening 2152 of the pedicle anchor 21 (that is, the area between the lower opening 2152 and the top end 213) will be wound by the suspension ligament 23 on the outer surface of the pedicle anchor 21. Therefore, by using a smaller-pitched thread portion 2121 with a smaller thread height and smoother thread tip near the top end 213 of the columnar body 211 of the pedicle anchor 21, not only the probability that the bone surface of the pedicle 122 being damaged by the pedicle anchor 21 can be reduced, the tightness of screw screwing can be improved, and the risk of the suspension ligament 23 being scratched or damaged by the thread of the pedicle anchor 21 can be significantly reduced. However, in another embodiment, the external thread 212 of the pedicle anchor 21 can also be designed such that the thread height and spacing remain the same no matter it is adjacent to or away from the top end 213, only that, the thread tip of the smaller-pitched thread portion 2121 is relative smoother. In a further embodiment, the external thread 212 of the pedicle anchor 21 can also be such designed that: the outer surface of the portion near to the top end 213 of the pedicle anchor 21 (that is, so-called smaller-pitched thread portion 2121) is formed with a rough surface without any thread, while the other portion away from the top end 213 of the pedicle anchor 21 (that is, so-called larger-pitched thread portion 2122) is formed with ordinary larger-pitched and sharp-tipped thread. And in yet a further embodiment, the external thread 212 of the pedicle anchor 21 can also be designed as that: the height of the thread near the top end 213 is relatively low, and the tip of the thread near the top end 213 is relatively smoother, but the pitch thereof remains the same; in contrast, the height and sharpness of the screw thread far from the top end 213 is relatively high, but the pitch remains the same. All such novel designs of the thread of pedicle anchor 21 can achieve the same advantages that: the probability that the bone surface of the pedicle 122 being damaged by the pedicle anchor 21 is reduced, the tightness of screw fixing is improved, and the risk of the suspension ligament 23 being scratched or damaged by the thread of the pedicle anchor 21 is significantly reduced. In a preferred embodiment, the outer diameter of the larger-pitched thread portion 2122 of the columnar body 211 is slightly larger than the outer diameter of the smaller-pitched thread portion 2121 of the columnar body 211 of the pedicle screw 21; such that, a small gap of around 0.5 mm or less is formed due to the difference between the outer diameters of the larger-pitched thread portion 2122 and the smaller-pitched thread portion 2121. Such novel design can minimize the risk to scratch or damage the suspension ligament 23 when the suspension ligament 23 is wound around the outer periphery of the smaller-pitched thread portion 2121 of pedicle anchor 21 which is installed in the pedicle 122.

Figure 5:
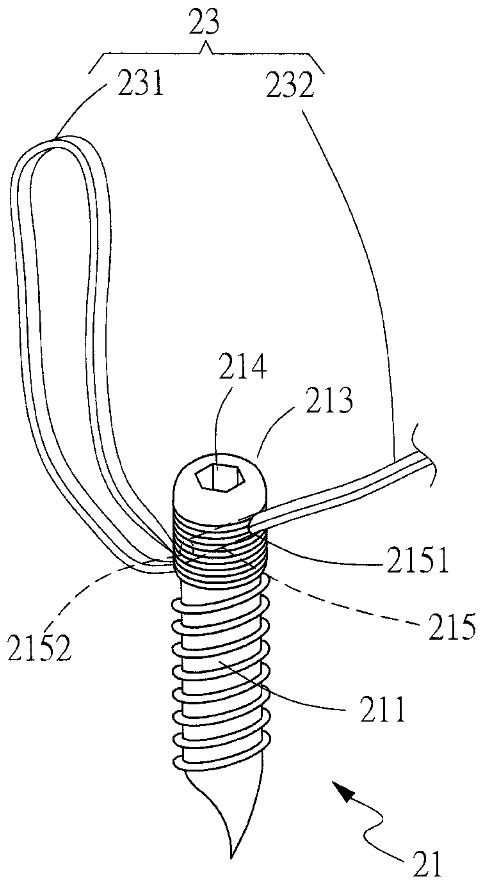
FIG. 5 is a schematic diagram showing an embodiment of the method for assembling the suspension ligament to the pedicle anchor of the T-PAS system of the present invention.

Please refer to FIG. 5, which is a schematic diagram showing an embodiment of the method for assembling the suspension ligament to the pedicle anchor of the T-PAS system of the present invention. In one of the embodiments of the present invention, a middle section of the suspension ligament 23 is folded into a double-line side-by-side structure and has a closed end 231 at the folded section and an open end 232 away from the folded section. The way to pass the suspension ligament 23 through the oblique through hole 215 is to pass the closed end 231 of the folded suspension ligament 23 into the oblique through hole 215 through the upper opening 2151, and then the closed end 231 of the folded suspension ligament 23 is pulled out from the lower opening 2152 of the oblique through hole 215; in the meantime, the open end 232 of the folded suspension ligament 23 remains exposed to the outside of the upper opening 2151

Figure 6A:
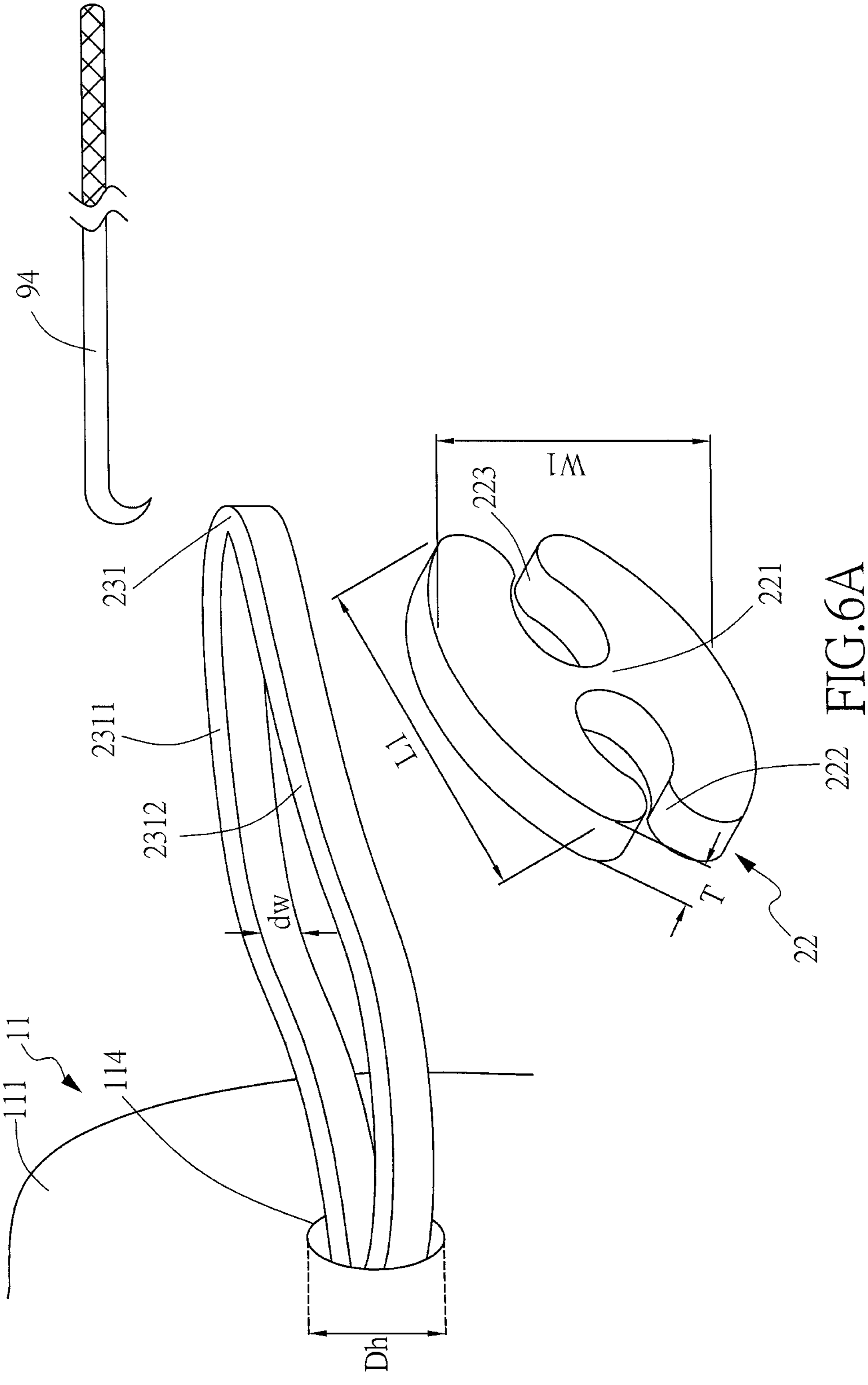
FIG. 6A and FIG. 6B are schematic diagrams showing an embodiment of the two steps for assembling the suspension ligament to the washer of the T-PAS system of the present invention.
Figure 6B:
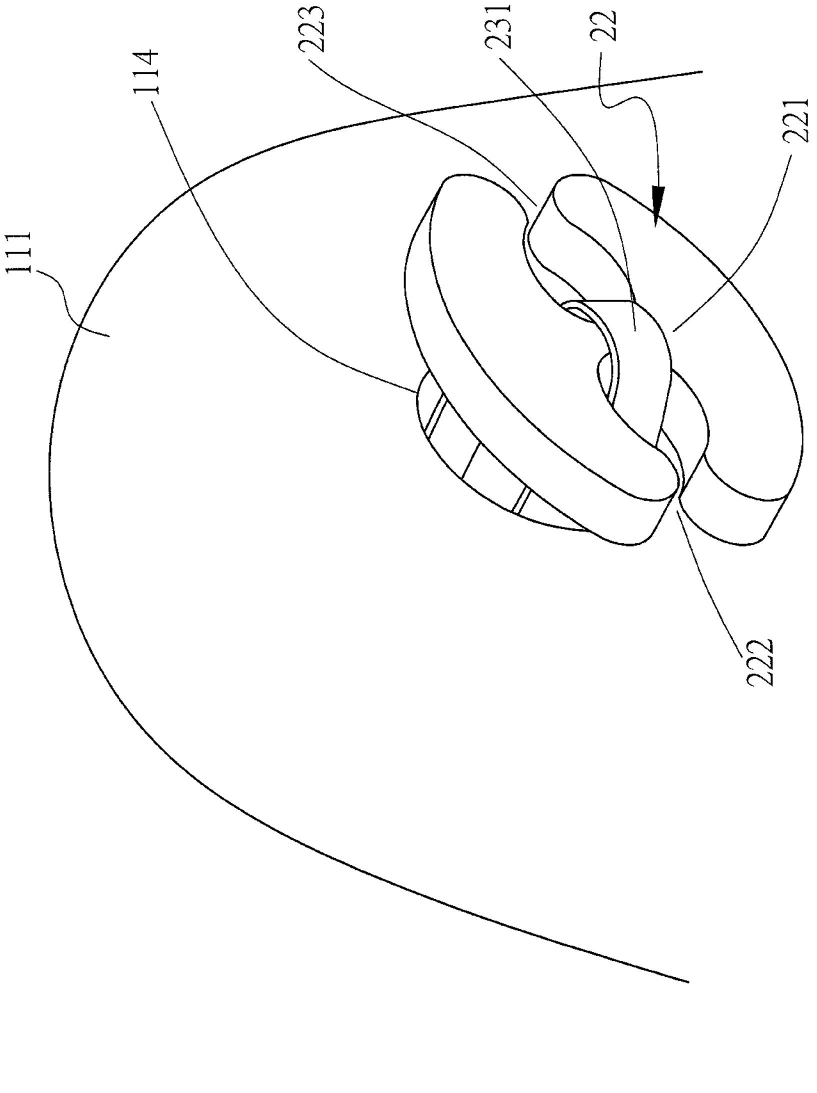

Please refer to FIG. 6A and FIG. 6B, which are schematic diagrams showing an embodiment of the steps for assembling the suspension ligament to the washer of the T-PAS system of the present invention. The washer 22 shown in FIG. 6A and FIG. 6B is an example of the Laminar Pig-Nose Washer. In one of the embodiments of the present invention, the method for assembling the suspension ligament 23 to the washer 22 is to first pull the closed end 231 of the folded middle section of the suspension ligament 23 out of the oblique through hole from the lower opening 2152 of the pedicle anchor 21; and secondly, use a slender elongated hook 94 (i.e., Suspension Ligament Off-Set Passer) to pass through the tunnel 114 of the lamina 111 of the upper vertebral segment from right to left, and use the hook 94 to hook the closed end 231 of the folded suspension ligament 23 on the left side of the lamina 111, and then pull the hook 94 together with the closed end 231 of the folded suspension ligament 23 toward right out of the tunnel 114 of the lamina 111; such that, the closed end 231 of the folded suspension ligament 23 is pulled through the tunnel 114 of the lamina 111 of the upper vertebral segment 11 (as shown in FIG. 6A). And thirdly, the closed end 231 of the folded suspension ligament 23 is placed on a bar portion 221 of the washer 22. The way to place the suspension ligament 23 onto the washer 22 is that, the left and right line segments 2311, 2312 of the closed end 231 of the suspension ligament 23 are inserted into the washer 22 through the openings 222, 223 on the left and right sides of the washer 22, respectively; so that the closed end 231 of the folded suspension ligament 23 can hook the rod 221 in the middle of the washer 22. After that, a pulling force is applied from the open end (not shown in this figure) of the suspension ligament 23 on the left side of the lamina 111, forcing the washer 22 to press the outer side-surface of the right end of the tunnel 214 of the lamina 111 of the upper vertebral segment 11, so as to achieve the effect of combining and fixing the closed end 231 of the suspension ligament 23 to the lamina 111 of the upper vertebral segment 11 by means of the washer 22 (as shown in FIG. 6B). In this embodiment, the shape of the washer 22 is similar to an "H" structure, and its length "L1" and width "W1" are larger than the diameter "Dh" of the tunnel 214 of the lamina 111, so it can be stuck outside the tunnel 214 and will not fall into the tunnel 214, and thus the closed end of the suspension ligament 23 can be fixed to the lamina 111 as long as the suspension ligament 23 is tightened by a predetermined tension. Preferably, the diameter "Dh" of the tunnel 214 of the lamina 111 can be between 1.5 mm-5 mm, the length "L1" of the washer 22 can be between 6 mm-10 mm, the width "W1" of the washer 22 can be between 6 mm-8 mm, and the thickness "T" of the washer 22 can be between 0.5 mm-2 mm. Preferably, the suspension ligament 23 is a flat strip-shaped artificial ligament, and its width "dw" can be between 1.5 mm-4 mm.

Figure 7A:
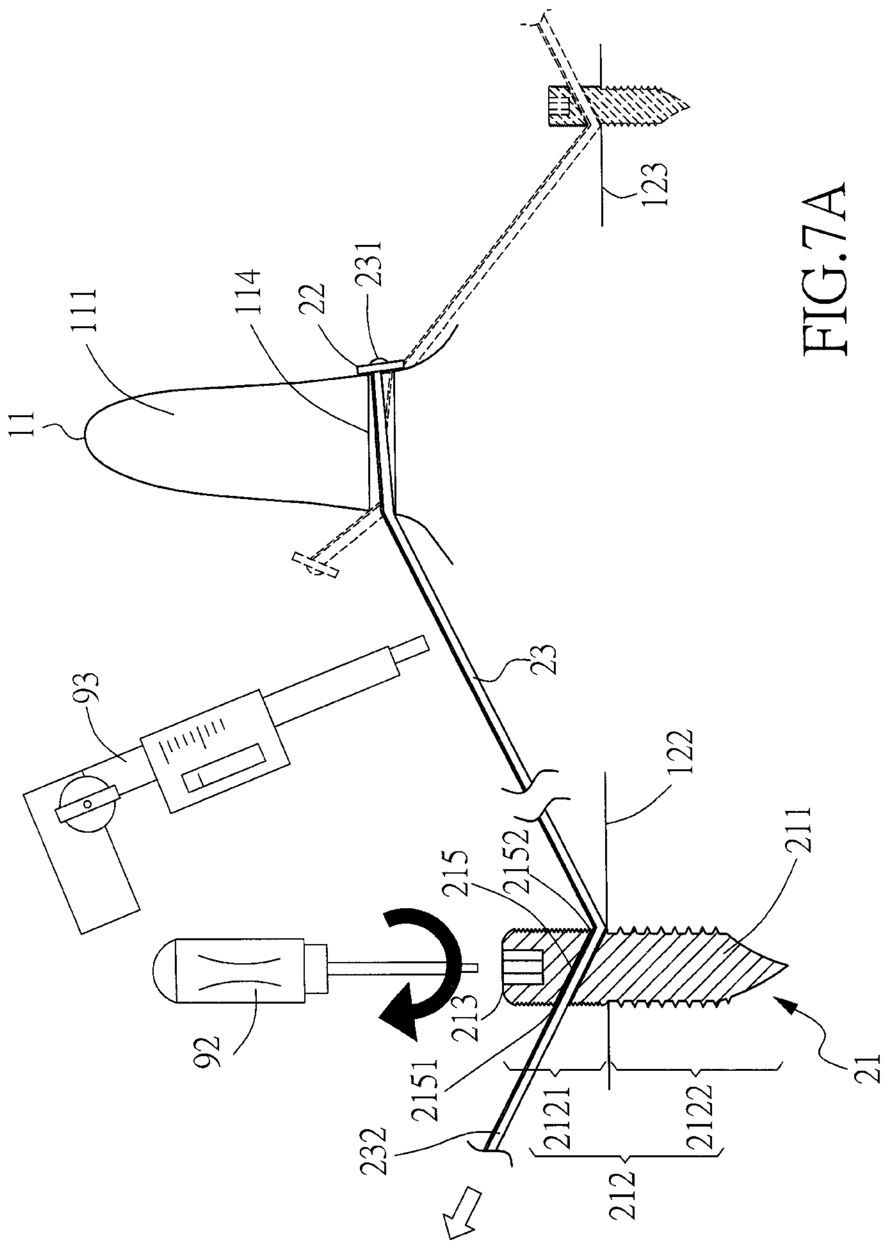
FIG. 7A and FIG. 7B respectively are schematic diagrams showing an embodiment of the steps for fixing the pedicle anchor to the pedicle of the lower vertebral segment in the T-PAS system of the present invention.
Figure 7B:
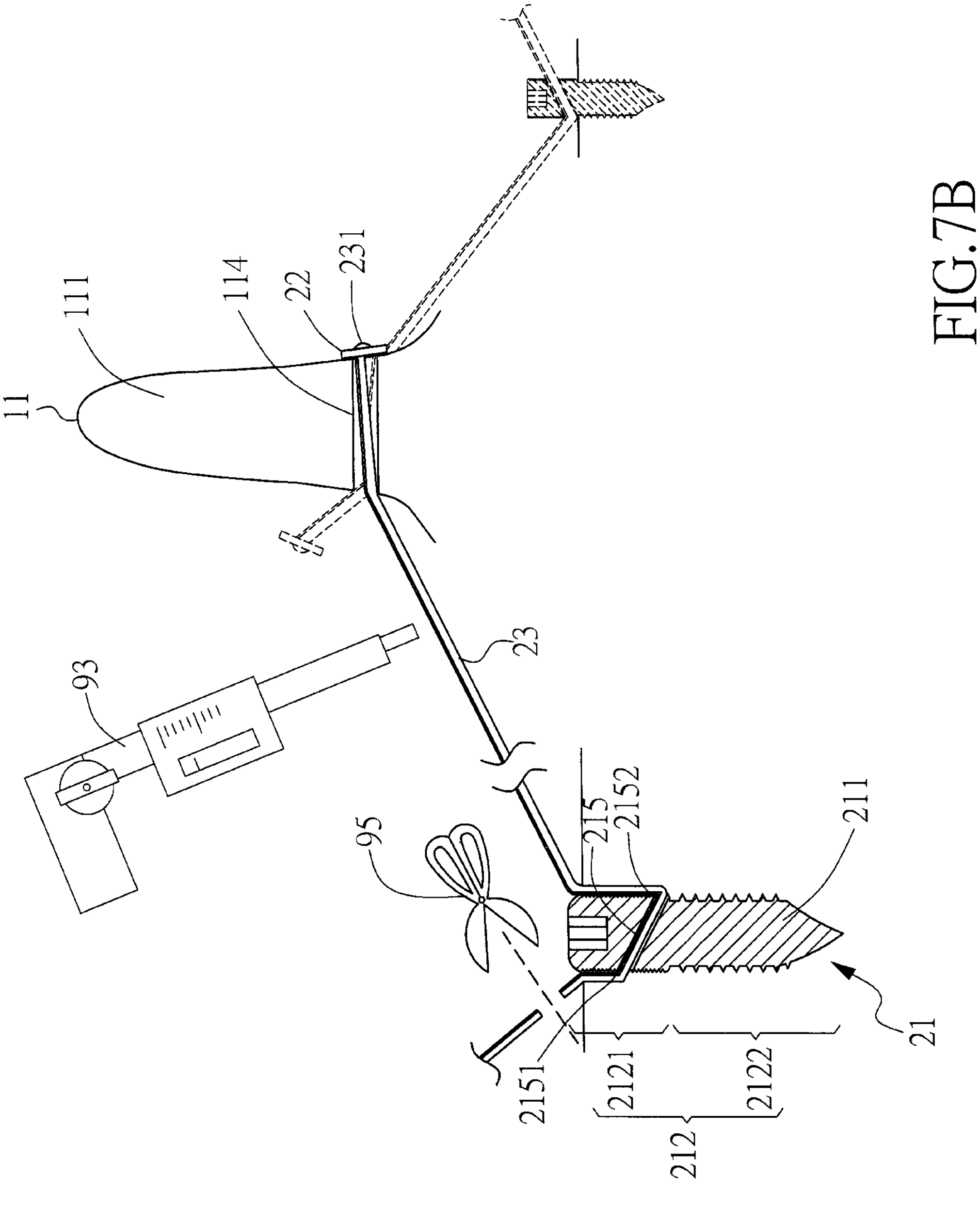

Please refer to FIG. 7A and FIG. 7B, which are respectively a schematic diagram showing an embodiment of the steps for fixing the pedicle anchor to the pedicle of the lower vertebral segment in the T-PAS system of the present invention. In one of the embodiments of the present invention, the method of fixing the pedicle anchor 21 to the pedicle 122 of the lower vertebral segment 12 is to first pull the closed end 231 of the middle section of the folded suspension ligament 23 out of the lower opening 2152 of the oblique through hole 215 of the pedicle anchor 21; then, screw a lower part of the columnar body 211 of the pedicle anchor 21 (for example, the larger-pitched thread portion) into the pedicle 122 of the lower vertebral segment 12, in order to make the lower opening 2152 of the pedicle anchor 21 close to but still exposed on the outer surface of the pedicle 122 of the lower vertebral segment 12 (as shown in FIG. 7A). Then, gently apply a slight pulling force from the open end 232 of the folded suspension ligament 23 so that the suspension ligament 23 temporarily has a relatively small first tension. This first tension must be less than the predetermined tension required by the suspension ligament 23 when the T-PAS system of the present invention is completely installed. The tension value of the suspension ligament 23 can be measured by operating the tension gauge 93 during the process of screwing the anchor 21. And then, when the screwdriver 92 is operated to screw the pedicle anchor 21, the pedicle anchor 21 is gradually screwed into the pedicle 122 of the lower vertebral segment 12, such that the lower opening 2152 of the pedicle anchor 21 is gradually embedded (sunk) into the pedicle 122 of the lower vertebral segment 12, and in the meantime, the suspension ligament 23 is gradually wound around the outer surface of the smaller-pitched thread portion 2121 of the pedicle anchor 21 and thus clamped between the outer surface of the pedicle anchor 21 and the inside of the pedicle 122 of the lower vertebral segment 12 (as shown in FIG. 7B). So that, one end of the suspension ligament 23 is clamped and fixed between the pedicle anchor 21 and the pedicle 122; in the meantime, the other end of the suspension ligament 23 is fixed to the contralateral side-surface of the lamina 111 of the upper vertebral segment 11 by using the washer 22. Thereby, in addition to connecting and fixing one end of the suspension ligament 23 to the pedicle 122 of the lower vertebral segment 12, the suspension ligament 23 can be further pulled by a larger force in order to tighten up the suspension ligament 23 to reach and maintain a relatively larger second tension. The second tension is much greater than the first tension and is the predetermined tension when the T-PAS system is completely installed. When the tension of the suspension ligament 23 measured by the tension gauge 93 has reached the predetermined tension, scissors 95 or surgical knives can be used to cut off the excess suspension ligament 23 (from the open end 232 of the tail of the suspension ligament 23) that is still exposed outside the pedicle 122. Similarly, the other pedicle anchor located on the other side is also screwed into the pedicle 123 in the same way and steps, furthermore, the predetermined tension is also provided to the suspension ligament fixed to the other pedicle anchor. When the operation of screwing the pedicle anchor 21 into the pedicle 123 is completed, the top end 213 of the anchor 21 will only slightly protrude or even be flush with the surface of the pedicle 123. After the T-PAS system 20 of the present invention is installed, only two pedicle anchors 21 need to be screwed into the pedicles 122, 123 of the lower vertebral segment 12, and the top end 213 of each pedicle anchor 21 is either flush with the surface of the pedicle 122 or only slightly protruding beyond the surface of the pedicle 122; generally speaking, the height of the top end 213 of the pedicle anchor 21 protruding beyond the surface of the pedicle 122 will not be higher than 5 mm. In addition, the washer 22 is also a thin-plate structure and is attaching on the side-surface of the lamina, such that the patient won't feel uncomfortable or foreign body sensation. Moreover, the suspension ligament 23 composed of artificial ligaments will not cause discomfort or pain to the patient, which does improve all the shortcomings of conventional technologies.

The aforementioned embodiment is merely one of preferred embodiments of the T-PAS system of the present invention, and not the only applicable embodiment. In the present invention, the structures of the pedicle anchor and the washer are not limited to the structures disclosed above, but there are other implementable structures.

Figure 8:
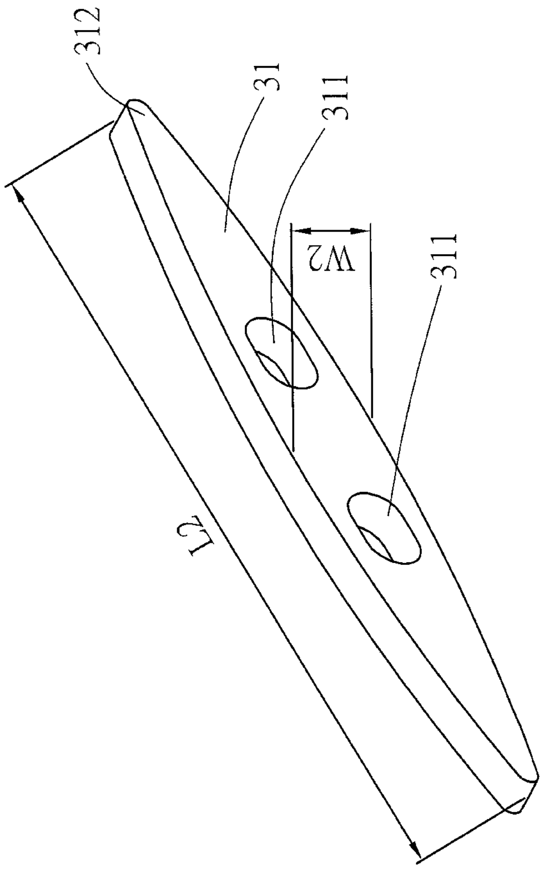
FIG. 8 is a perspective diagram of another embodiment of the washer in the T-PAS system of the present invention.
Figure 9B:
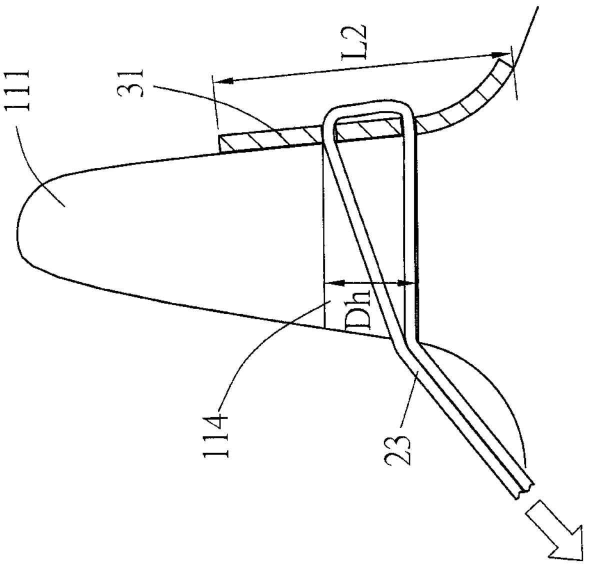
FIG. 9A and FIG. 9B are schematic diagrams of the two steps of the method for connecting the suspension ligament to the washer as shown in FIG. 8 respectively.
Figure 9A:
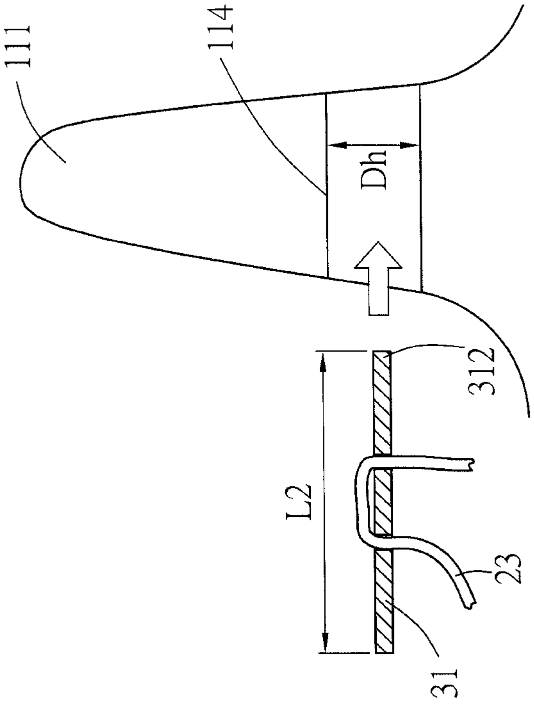

For example, please refer to FIG. 8, FIG. 9A and FIG. 9B; wherein, FIG. 8 is a perspective diagram of another embodiment of the washer in the T-PAS system of the present invention; FIG. 9A and FIG. 9B are schematic diagrams of the two steps of the method for connecting the suspension ligament to the washer as shown in FIG. 8 respectively. The washer 31 shown in FIG. 8 is an example of Laminar Banana Washer. In this embodiment, the washer 31 may be a thin and elongated plate-like structure with a relatively small width "W2" and a relatively long length "L2". The width "W2" of the washer 31 is smaller than the diameter "Dh" of the tunnel 114 of the lamina 111 (W2<Dh), the thickness of the washer 31 is also smaller than the diameter "Dh" of the tunnel 114, and the length "L2" is greater than the diameter "Dh" of the tunnel 114 of the lamina 111 (L2>Dh). Two or more through holes 311 are provided on the washer 31, such that the suspension ligament 23 can be sequentially passed through these through holes 311 to achieve the purpose of binding/assembling the suspension ligament 23 to the washer 31. Next, as shown in FIG. 9A, align the end 312 of the washer 31 connected with the suspension ligament 23 to the tunnel 114 of the lamina 111 in the elongated direction. Utilizing the characteristic that the width "W2" and thickness of the washer 31 are both smaller than the diameter "Dh" of the tunnel 114, the washer 31 together with the suspension ligament 23 can be inserted and then passed through the tunnel 114 of the lamina 111 to the other side of the lamina 111. After that, as shown in FIG. 9B, turn the washer 31 to an angle and pull the suspension ligament 23 from the left side of the lamina 111, then the slender side of the washer 31 with a length of "L2" can press against the right side-surface of the lamina 111, so as to achieve the purpose of fixing one end of the suspension ligament 23 on the right side of the tunnel 114 of the lamina 111 by means of the washer 31.

Figure 10A:
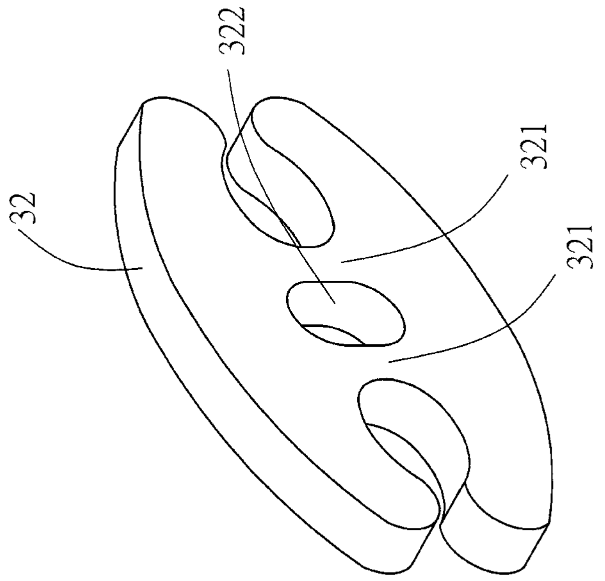
FIG. 10A is a perspective view of yet another embodiment of the washer of the T-PAS system of the present invention.

Please refer to FIG. 10A, which is a perspective view of yet another embodiment of the washer of the T-PAS system of the present invention. The structure of the washer shown in this embodiment is almost the same as the washer shown in FIG. 6A, and the way to use is also similar. The only difference between these two washers is that, the washer 32 shown in FIG. 10A is provided with two bar portions 321, and an additional opening 322 is formed between the two bar portions 321. Such structure allows the suspension ligament to pass through the opening 322 and be wound around the two bar portions 321 of the washer 32, in order to provide a more stable and non-slip binding effect.

Figure 10B:
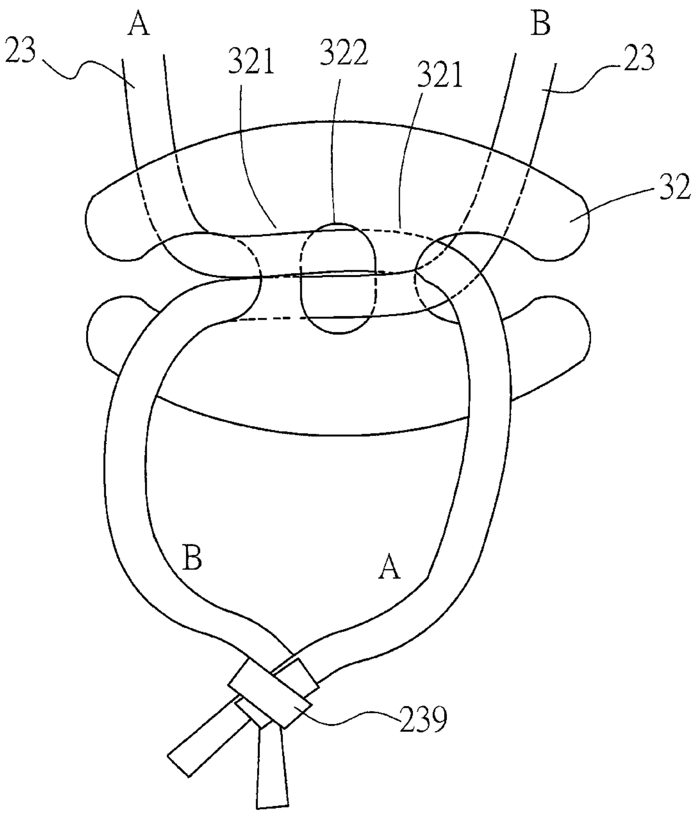
FIG. 10B is a schematic diagram showing an embodiment of a method to tie the suspension ligament on the washer shown in FIG. 10A of the T-PAS system of the present invention.

Please refer to FIG. 10B, which is a schematic diagram showing an embodiment of a method to tie the suspension ligament on the washer shown in FIG. 10A of the T-PAS system of the present invention. In this embodiment, the suspension ligament 23 first passes through the through hole of the pedicle screw (not shown in this figure) such that the pedicle screw is substantially hung on a middle portion of the suspension ligament 23. Then, the free ends of the two strips "A" and "B" of the suspension ligament 23 pass through the tunnel of the lamina (not shown in this figure). After that, the free ends of the two strips "A" and "B" of the suspension ligament 23 pass across the bar portions 321 and the middle opening 322 from two sides of the washer 32 and then are tied up with at least 5 knots 239 to ensure the stability of connection between the suspension ligament 23 and the washer 32.

Figure 11A:
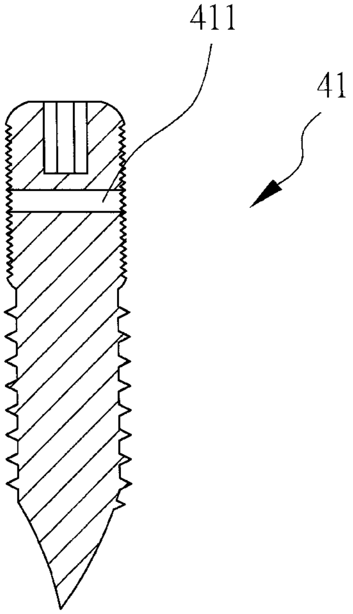
FIG. 11A is a schematic cross-sectional diagram of another embodiment of the pedicle anchor in the T-PAS system of the present invention.

Please refer to FIG. 11A, which is a schematic cross-sectional diagram of another embodiment of the pedicle anchor in the T-PAS system of the present invention. The structure of the pedicle anchor 41 shown in this embodiment is substantially the same as that of the pedicle anchor 21 shown in FIG. 4A and FIG. 4B, and the method of use is also similar. The only difference between these two pedicle anchors is that, the through hole 411 of the anchor 41 shown in FIG. 11A is a horizontal through hole 411, the openings at both ends of the through hole 411 are located at the same height. In the other hand, the two openings 2151, 2152 at two ends of the oblique through hole 215 of the pedicle anchor 21 shown in FIG. 4A and FIG. 4B are located at different heights.

Figure 11B:
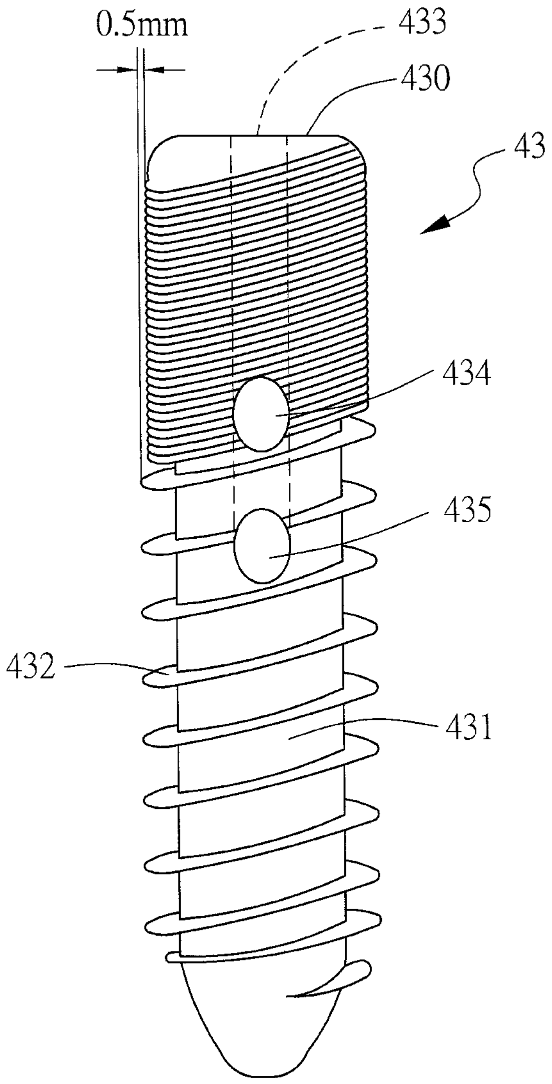
FIG. 11B is a schematic cross-sectional diagram of yet another embodiment of the pedicle anchor of the T-PAS system of the present invention.

Please refer to FIG. 11B, which is a schematic cross-sectional diagram of yet another embodiment of the pedicle anchor of the T-PAS system of the present invention. In this embodiment, the pedicle anchor 43 also has a columnar body 431 and a counterbore 433 extending downward from the top end 430 of the columnar body 431 along the central axis. Two or more transverse through holes 434, 435 are provided on the columnar body 431, which are connected with the counterbore 433. After the suspension ligament is inserted into the counterbore 433 from the top end 430 of the columnar body 431, the suspension ligament located inside the counterbore 433 can be pulled out of the columnar body 431 from one of the through holes 434 and then inserted into the counterbore 433 again via the other through hole 435, such that the suspension ligament can be bound to the pedicle anchor 43 more firmly. In addition, the pitch and height of the external thread 432 provided on the outer surface of the columnar body 431 are consistent throughout the whole columnar body 431, and there is no difference between the so-called smaller-pitched thread portion or the larger-pitched thread portion.

Figure 11C:
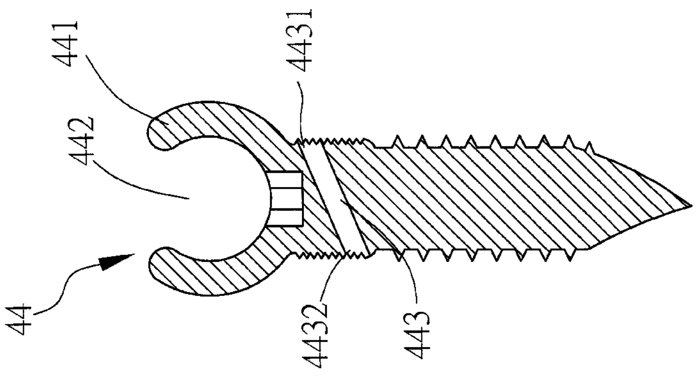
FIG. 11C is a schematic cross-sectional diagram of a further embodiment of the pedicle anchor in the T-PAS system of the present invention.

Please refer to FIG. 11C, which is a schematic cross-sectional diagram of a further embodiment of the pedicle anchor in the T-PAS system of the present invention. The structure of the pedicle anchor 44 shown in this embodiment is substantially the same as that of the pedicle anchor 21 shown in FIG. 4A and FIG. 4B, and the method of use is also similar. In the embodiment shown in FIG. 11C, the pedicle anchor 44 also has an elongated columnar body extending along a central axis, an external thread provided on the outer surface of the columnar body, a fitting structure provided at the top end of the columnar body, and an oblique through hole 443 penetrating columnar body; wherein, the upper opening 4431 and the lower opening 4432 at two ends of the oblique through hole 443 are also located at different height. That means, there is a height difference between the upper opening 4431 and the lower opening 4432 at two ends of the oblique through hole 443. The only difference between the two embodiments shown in FIG. 11C and FIG. 4A is that, a U-shaped rod-holding rack 441 is additionally provided at the top end of the columnar body of the pedicle anchor 44 shown in FIG. 11C. The rod-holding rack 441 has a rod-holding seat 442 for accommodating a connecting rod (not shown in the figure), so that the T-PAS system of the present invention can be used with a conventional spinal fixator.

Figure 11D:
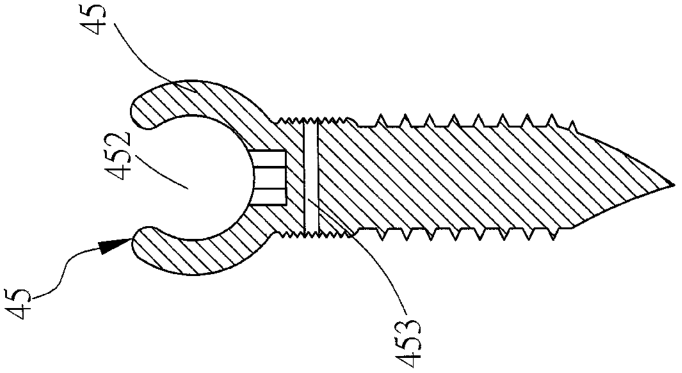
FIG. 11D is a schematic cross-sectional diagram of yet an even further embodiment of the pedicle anchor in the T-PAS system of the present invention.

Please refer to FIG. 11D, which is a schematic cross-sectional diagram of yet an even further embodiment of the pedicle anchor in the T-PAS system of the present invention. The structure of the pedicle anchor 45 shown in this embodiment is substantially the same as that of the pedicle anchor 44 shown in FIG. 11C, and the method of use is also similar. The pedicle anchor 45 also has a U-shaped rod-holding rack 451 and a rod-holding seat 452 at the top end of the columnar body of the pedicle anchor 45. The only difference between the two pedicle anchors 44, 45 is that, the through hole 453 of the pedicle anchor 45 shown in FIG. 11D is a horizontal through hole 453, and the two openings of the two ends of the through hole 453 are located at the same height. In the other hand, the two openings 2151, 2152, 4431, 4432 at two ends of the oblique through hole 215, 443 of the pedicle anchor 21, 44 shown in FIG. 4A, FIG. 4B or FIG. 11D are located at different heights. The pedicle anchors 44 and 45 shown in FIG. 11C and FIG. 11D are two examples of Headed Suspension Pedicle Anchor (HSPA), in which, the U-shaped rod-holding rack 451 (or 441) of the pedicle anchor 45 (or 44) can be a fixed head or a polyaxial head.

When manufacturing or selling the T-PAS system of the present invention, the tools and components required in the T-PAS system can be pre-sterilized, pre-semi-assembled and pre-packaged into a component set, in order to facilitate surgeons in performing surgery that installs the T-PAS system into the patient's vertebrae. In an embodiment, the component set of the T-PAS system of the present invention may include: several pedicle anchors, several washers, several suspension ligaments (artificial ligaments), a screwdriver, and a tension gauge. The pedicle anchor is used to be fixed to the pedicle of the lower vertebral segment. The washer is located at the end of the tunnel formed in the lamina of the upper vertebral segment. The suspension ligament is used to connect the pedicle anchor and the washer; in addition, the suspension ligament is fixed to both the pedicle of the lower vertebral segment and the lamina of the upper vertebral segment by means of the pedicle anchor and the washer. Moreover, in this component set, the suspension ligament is pre-assembled on the pedicle anchor. The screwdriver can be connected to the pedicle anchor, such that the pedicle anchor can be screwed into the pedicle of the lower vertebral segment by operating the screwdriver. The tension gauge is used to measure the tension of the suspension ligament. With this component set, the process for surgeons to perform surgery for installing the T-PAS system can be facilitated and sped up, thereby reducing the risk of surgery.

Figure 12A:
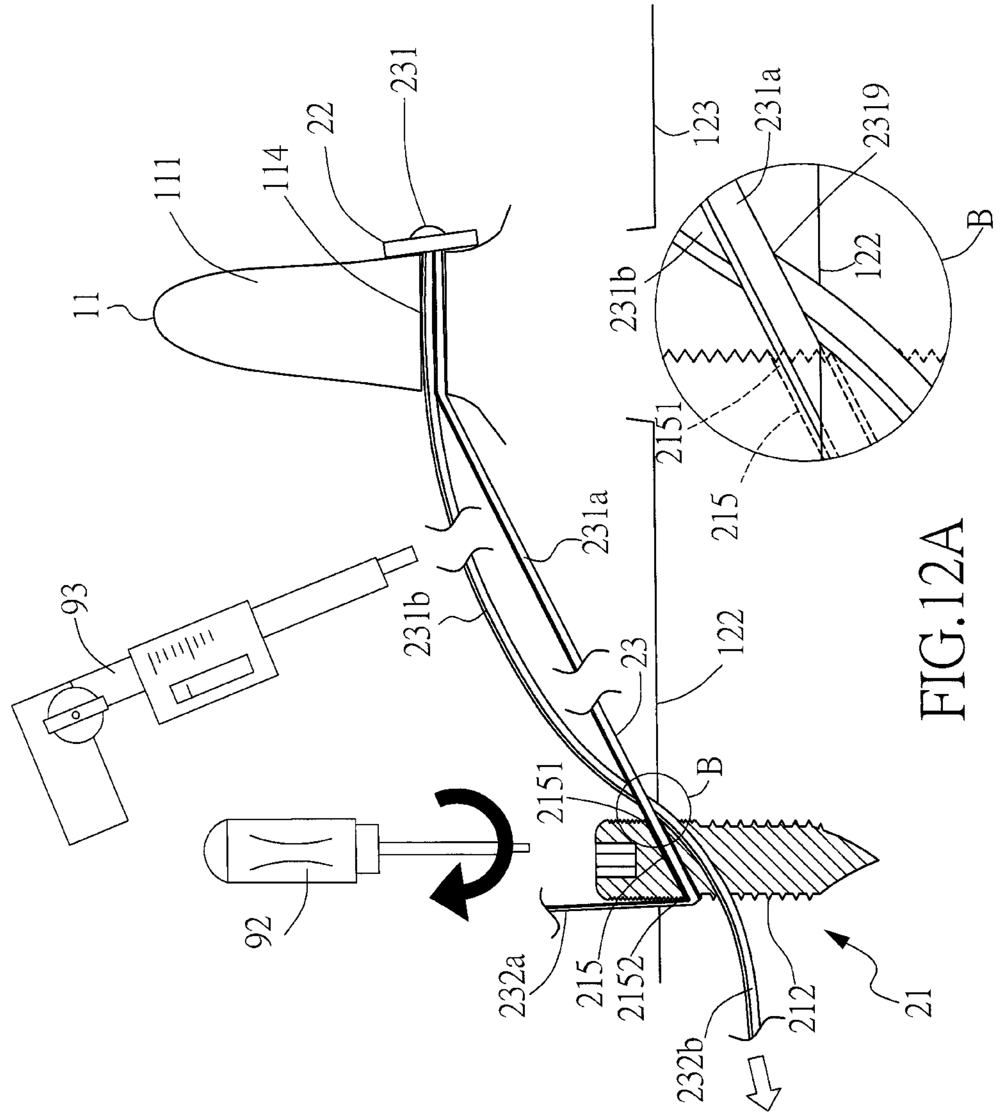
FIG. 12A and FIG. 12B respectively are schematic diagrams showing another embodiment of the steps for fixing the pedicle anchor to the pedicle of the lower vertebral segment in the T-PAS system of the present invention.
Figure 12B:
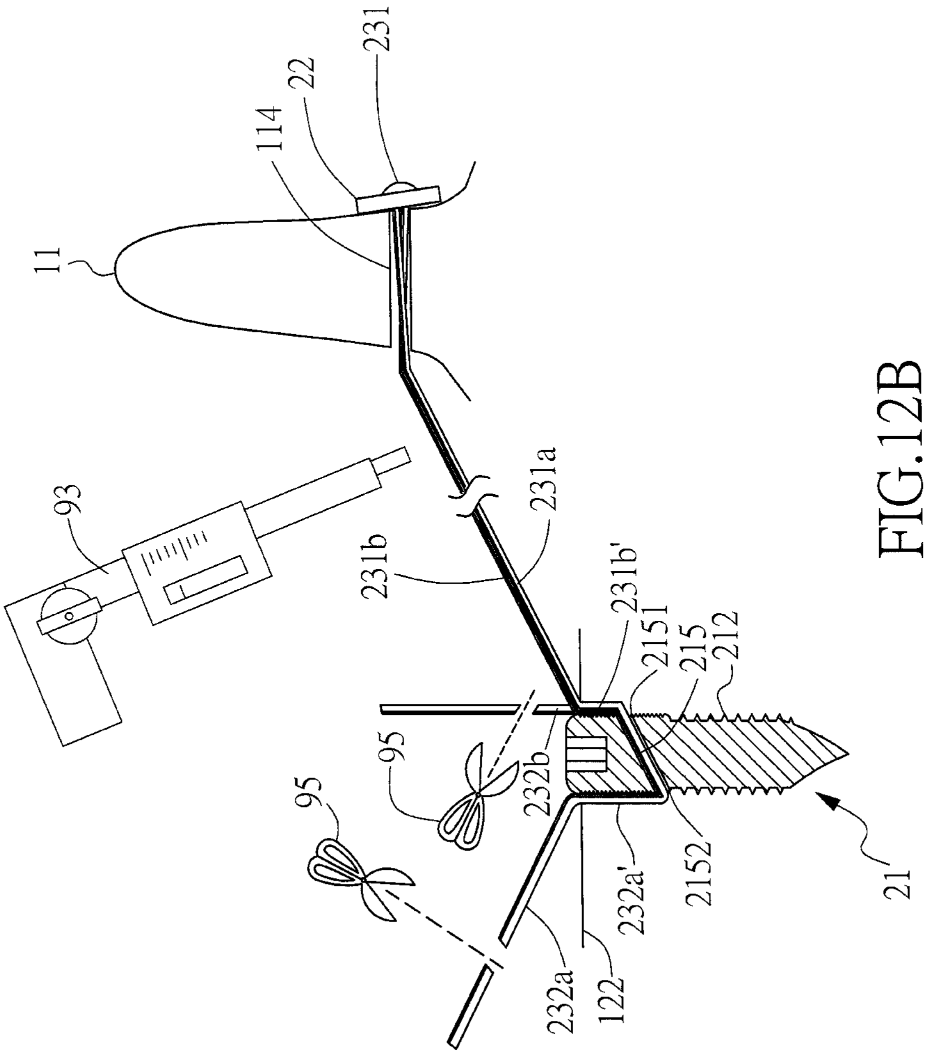

Please refer to FIG. 12A and FIG. 12B, which are respectively a schematic diagram showing another embodiment of the steps for fixing the pedicle anchor to the pedicle of the lower vertebral segment in the T-PAS system of the present invention. In the T-PAS system of the present invention, in addition to the method and steps illustrated in FIG. 7A and FIG. 7B and their related descriptions, the method and steps shown in FIG. 12A and FIG. 12B can also be used to fix the pedicle anchor to the pedicle of the lower vertebral segment. In the embodiment shown in FIG. 12A and FIG. 12B, the way to pass the suspension ligament 23 through the oblique through hole 215 of the pedicle anchor 21 is to pass one end of the suspension ligament 23 through the lower opening 2152 into the oblique through hole 215 and then pull out the suspension ligament 23 out of the oblique through hole 215 via the upper opening 2151, such that the two free ends 232*a*, 232*b* (open ends) of the suspension ligament 23 are respectively exposed out of the lower opening 2152 and the upper opening 2151. Wherein, the middle section and the closed end 231 of the suspension ligament 23 are both located at the portion of the suspension ligament 23 pulled out from the upper opening 2151. As shown in FIG. 12A, the method for fixing the pedicle anchor 21 to the pedicle 122 of the lower vertebral segment is to use a screwdriver 92 to first screw a lower part of the pedicle anchor 21 into the pedicle 122 of the lower vertebral segment, such that the lower opening 2152 together with the free end 232*a* (open end) of the suspension ligament 23 extended out from the lower opening 2152 are screwed into and clamped between the outer surface of the pedicle anchor 21 and the pedicle 122 of the lower vertebral segment; however, in the meantime, the upper opening 2151 and the parts 231*a*, 231*b* of the suspension ligament 23 extending out from the upper opening 2151 are still exposed outside the pedicle 122 of the lower vertebral segment. Next, the other free end 232*b* (open end) of the suspension ligament 23 exposed outside of the pedicle 122 is first pulled to a location near the upper opening 2151, then the other free end 232*b* (open end) is pulled to pass through the part 231*a* of the suspension ligament 23 from below, and then, keep pulling the other free end 232*b* (open end) with a pulling force so that the suspension ligament temporarily has a relatively small first tension. That is, as shown in the partially enlarged view of the upper opening 2151 shown in the lower right area "B" in FIG. 12A, the touched point 2319 of the two parts 231*a*, 231*b* of the suspension ligament 23 is exactly stuck at the intersection of the upper opening 2151 and the outer surface of the pedicle 122, and the part 231*a* is in contact with and pressed against the other part 231*b* of the suspension ligament 23. And then, as shown in FIG. 12B, use a screwdriver 92 to gradually screw the pedicle anchor 21 into the pedicle 122 of the lower vertebral segment, so that the upper opening 2151 of the pedicle anchor 21 is embedded into the pedicle 122 of the lower vertebral segment; in the same time, the part 231*a* of the suspension ligament 23 extending from the upper opening 2151 and the other part 231*b*' connected to the other free end 232*b* (open end) are both wound around the outer surface of the pedicle anchor 21 and thereby sandwiched and clamped between the outer surface of the pedicle anchor 21 and the inside of the pedicle 122 of the lower vertebral segment. The screwdriver 92 keeps gradually screwing the pedicle anchor 21 into the pedicle 122 to tighten the suspension ligament 23 until the tension of the two parts 231*a*, 231*b* of the suspension ligament 23 measured by the tension gauge 93 reaches a relatively large second tension value. In addition to the two free ends 232*a*, 232*b* (open ends) of the suspension ligament 23 can be connected and fixed at the pedicle 122 of the lower vertebral segment, the suspension ligament 23 can be further pulled to reach and maintain at a relatively large second tension. The second tension is much greater than the first tension and is the predetermined tension when the T-PAS system is completely installed. When the tension of the suspension ligament 23 measured by the tension gauge 93 has reached the predetermined tension, scissors 95 or surgical knives can be used to cut off the excess suspension ligament 23 from the free ends 232*a*, 232*b* (open ends) of the suspension ligament 23. In an embodiment, when the other part 231*b* of the suspension ligament 23 is passed under the part 231*a* of the suspension ligament 23 at the upper opening 2151, the other part 231*b* of the suspension ligament 23 can be additionally wound around the outer surface of the pedicle anchor 21 for one circle or two circles, in order to ensure that, when the pedicle anchor 21 is gradually screwed into the pedicle 122 of the lower vertebral segment by using the screwdriver 92, the other part 231*b*' will be wound together on the outer surface of the pedicle anchor 21 and thus clamped between the outer surface of the pedicle anchor 21 and the inside of the pedicle 122 of the lower vertebral segment.

Figure 13B:
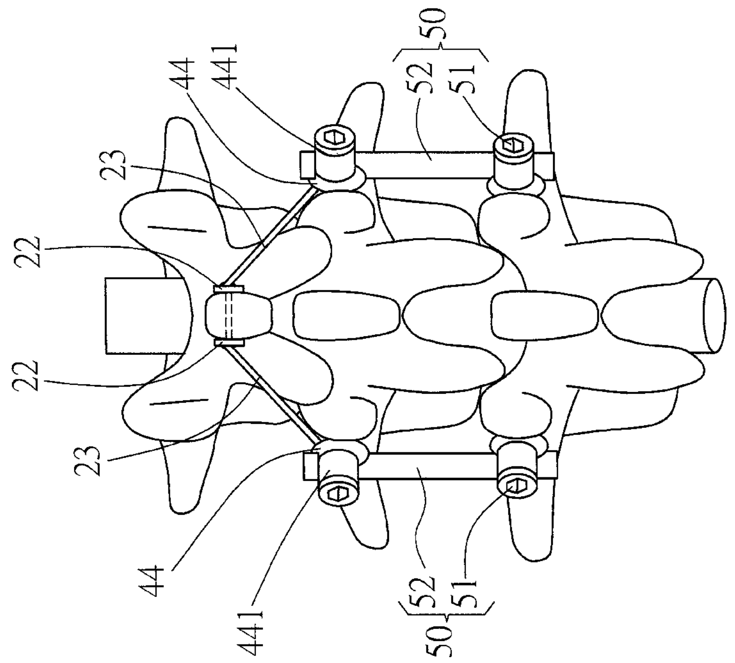
FIG. 13A and FIG. 13B are schematic diagrams of two embodiments of the T-PAS system of the present invention being used with the conventional spinal fixator.
Figure 13A:
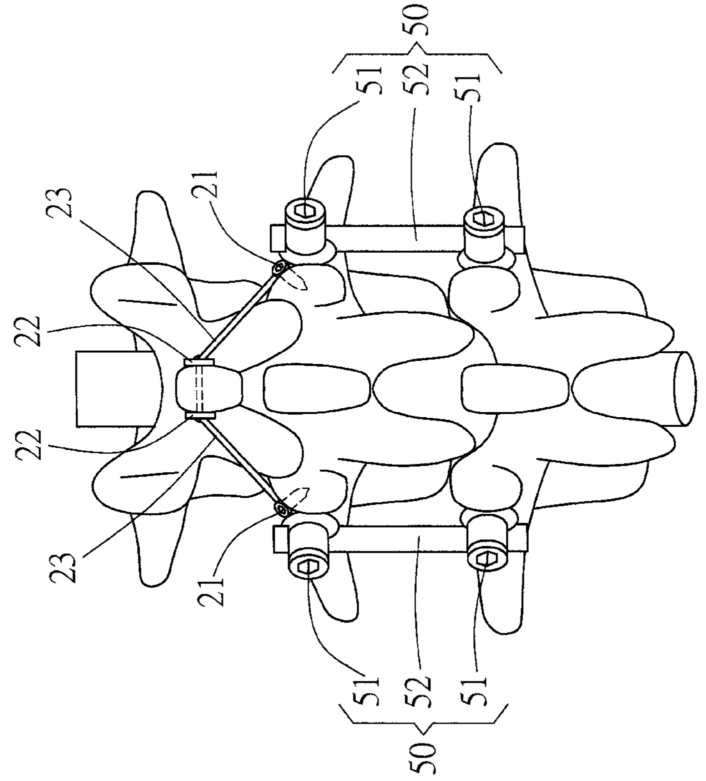

Please refer to FIG. 13A and FIG. 13B, which are schematic diagrams of two embodiments of the T-PAS system of the present invention being used with the conventional spinal fixator. Even if the patient to be operated has already had surgery and installed a conventional spinal fixator before, and now there is a need for spine surgery again, the T-PAS system of the present invention can still be installed in subsequent operations to be used in conjunction with the previously installed conventional spinal fixator. As shown in FIG. 13A, generally speaking, a typical conventional spinal fixator 50 will include at least four pedicle screws 51 and two connecting rods 52 (fusion rods); wherein, each of the pedicles of both sides of both the upper and lower vertebral segments is screwed with a pedicle screw 51; and then, each pair of the two pedicle screws 51 located on the same side of the upper and lower vertebral segments is connected by a connecting rod 52. Sometimes, a fixing plate (not shown in the figure) is added to the two connecting rods 52 or the pedicle screws 51 to strengthen the fixing effect. In the embodiment shown in FIG. 13A, the T-PAS system of the present invention can select two smaller pedicle anchors 21 of the invention to be respectively screwed on the pedicles of the upper vertebral segment at locations adjacent to (but not contact with) the pedicle screws 51 of the conventional spinal fixator 50. In addition, the two ends of the tunnel of the lamina of a further upper vertebral segment are respectively provided with washers 22 of the T-PAS system of the present invention. Moreover, a suspension ligament 23 with a predetermined tension is used to connect the pedicle anchor 21 on one side and the washer 22 on the other side through the tunnel of the lamina. Thereby, under the premise that the function of the existing conventional spinal fixator 50 is not affected, the T-PAS system of the present invention can be installed between the upper vertebral segment and the further upper vertebral segment in order to suspend them. Wherein, the smaller pedicle anchor 21 used in this embodiment is an example of Suspension Abutment Pedicle Anchor (SAPA).

As shown in FIG. 13B, another way to use the T-PAS system of the present invention conjunction with the conventional spinal fixator 50 is to remove both the left and right conventional pedicle screws of the conventional spine fixator 50 located at the upper vertebral segment; and then replace these two conventional pedicle screws with two pedicle anchors 44 (or 45) equipped with U-shaped rod-holding rack 441 (or 451), rod-holding seat 442 (or 452) and through hole 443 (or 453) as shown in FIG. 11C (or FIG. 11D). In addition, the two ends of the tunnel of the lamina of the further upper vertebral segment are respectively provided with washers 22 of the T-PAS system of the present invention. Moreover, a suspension ligament 23 with a predetermined tension is used to connect the pedicle anchor 44 (or 45) on one side and the washer 22 on the other side through the tunnel of the lamina. Because the pedicle anchor 44 (or 45) of the present invention located in the upper vertebrae also has the rod-holding rack 441 (or 451) and rod-holding seat 442 (or 452), therefore the connecting rod 52 of the conventional spinal fixator 50 that is originally installed can be directly assembled and fixed to the pedicle anchor 44 (or 45) of the present invention. Thereby, under the premise that the function of the existing conventional spinal fixator 50 is not affected, the T-PAS system of the present invention can be installed between the upper vertebral segment and the further upper vertebral segment in order to suspend them.

Wherein, the pedicle anchor 44 (or 45) used in this embodiment is an example of Headed Suspension Pedicle Anchor (HSPA).

Figure 14:
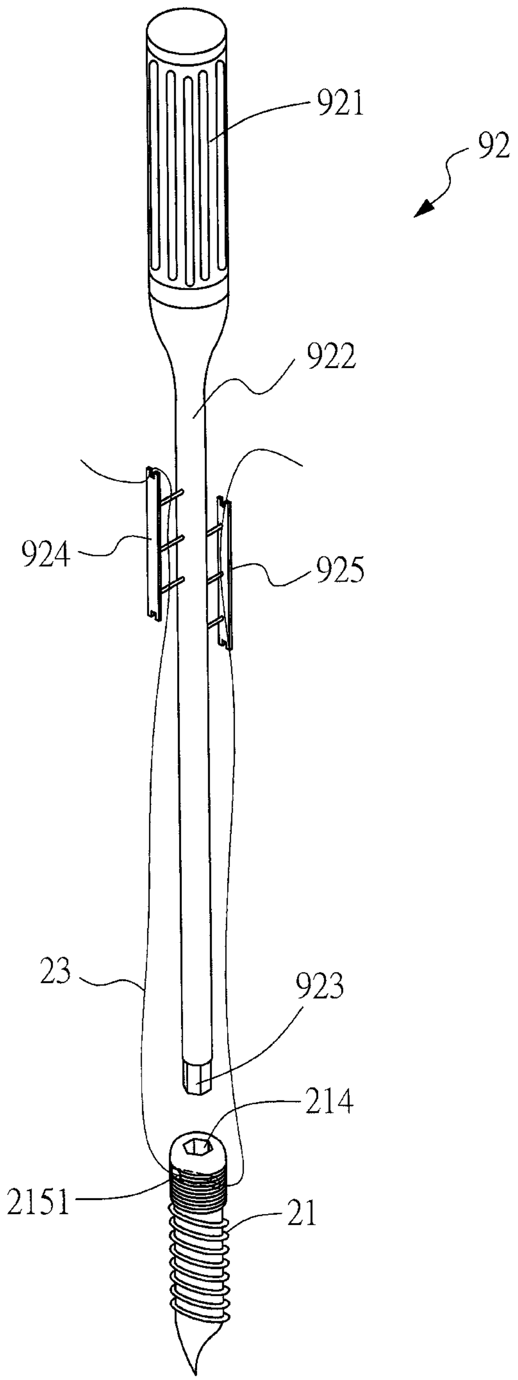
FIG. 14 is a schematic diagram of an embodiment of the screwdriver in the component set of the T-PAS system of the present invention.

Please refer to FIG. 14, which is a schematic diagram of an embodiment of the screwdriver in the component set of the T-PAS system of the present invention. Because the T-PAS system of the present invention uses a slender, long, soft and tough artificial ligament as a suspension wire, in order to prevent the suspension ligament from being entangled by itself or entangled on the screwdriver during the operation, the present invention discloses an innovative screwdriver 92 to overcome the aforementioned problems. As shown in FIG. 14, the screwdriver 92 includes: a handle 921, a long-rod portion 922, a driver head 923, an upper hanger 924 and a lower hanger 925. The long-rod portion 922 extends a predetermined length from one end of the handle 921 along an axis. The driver head 923 is located at an end of the long-rod portion 922 away from the handle 921. The structure of the driver head 923 corresponds to the fitting structure 214 of the pedicle anchor 21 of the present invention and can be connected with the fitting structure 214 of the pedicle anchor 21; such that, when the handle 921 rotates, the driver head 923 will also drive the pedicle anchor 21 to rotate. The upper hanger 924 and the lower hanger 925 are both furnished on the long-rod portion 922. Wherein, the lower hanger 925 is furnished on the long-rod portion 922 at a position corresponding to the upper hanger 924 across the axis; in addition, the distance between the lower end of the upper hanger 924 and the driver head 923 is greater than the distance between the lower end of the lower hanger 925 and the driver head 923. In other words, the upper and lower hangers 924 and 925 are located on opposite sides of the long-rod portion 922 and present a "one higher" and "one lower" configuration. Which mean, the upper hanger 924 is located higher than the lower hanger 925. In addition, when the driver head 923 is coupled to the fitting structure 214 of the pedicle anchor 21, the position of the upper hanger 924 exactly corresponds to the position of the upper opening 2151 of the pedicle anchor 21, in the meantime, the position of the lower hanger 925 exactly corresponds to the position of the lower opening 2152 of the pedicle anchor 21. Therefore, when performing an operation, the surgeon only needs to observe the position or rotation angle of the upper and lower hangers 924 and 925, he/she will know the current position or rotation angle of the upper and lower openings 2151 and 2152 of the pedicle anchor 21 being driven by the screwdriver 92. Moreover, the upper hanger 924 and the lower hanger 925 each has an elongated sheet which is connected to the long-rod portion by several convex posts, and the upper and lower ends of the elongated sheet are slightly protruding from the convex post in the axial direction. Furthermore, the upper end of the elongated sheet is provided with a recess. The structural design of the upper and lower hangers allows the two ends of the suspension ligament 23 extending from the upper and lower openings of the oblique through hole of the pedicle anchor to be respectively wound and hung on the convex posts of the upper and lower hangers 924 and 925, and also allows the two ends of the suspension ligament 23 to be inserted in the recesses of the upper and lower hangers 924 and 925, so as to avoid the situation that the suspension ligament 23 is entangled by itself or entangled on the screwdriver 92 when the screwdriver 92 is operated to rotate the pedicle anchor 21.

Figure 15:
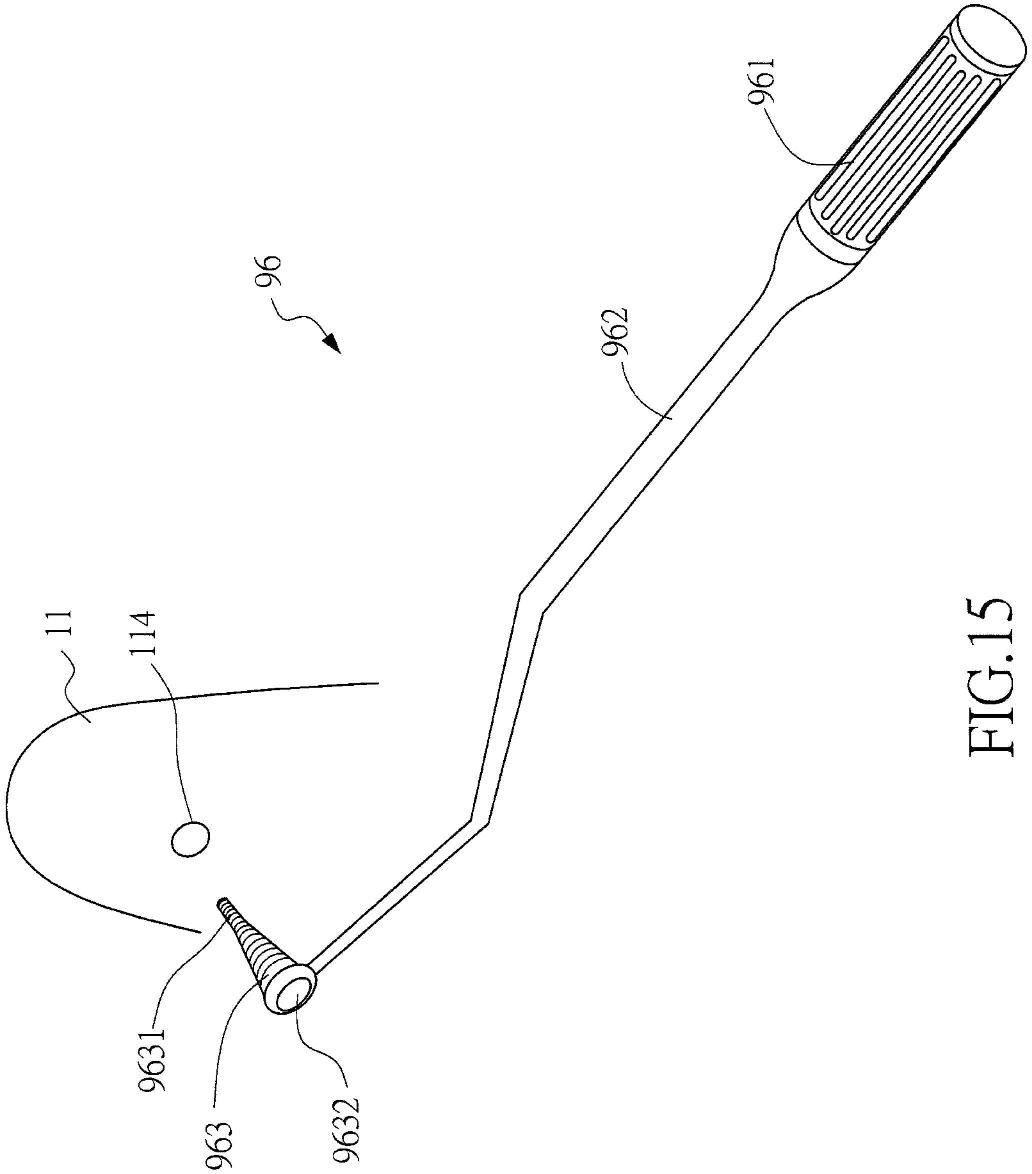
FIG. 15 is a schematic diagram of an embodiment of the hand-held file in the component set of the T-PAS system of the present invention.

Please refer to FIG. 15, which is a schematic diagram of an embodiment of the hand-held file in the component set of the T-PAS system of the present invention. In the present invention, a manual drill (i.e., Laminar Drill Guide) will be used to drill a tunnel on the lamina of the upper vertebral segment. Because the tunnel just drilled out often has sharp edges or cracks, it is easy to scratch the suspension ligament or break due to the tension of the suspension ligament. Therefore, the present invention discloses an innovative hand-held file 96 for smoothing the inner surface and the edge of the tunnel. The hand-held file 96 includes: a handle 961, a long-pole portion 962, and a conical file head 963. The long-pole portion 962 extends a predetermined length from one end of the handle 961 along an axis. The conical file head 963 is located at an end of the long-pole portion 962 away from the handle 961. The conical file head 963 is a cone-shaped structure and its protruding direction is approximately perpendicular to the axial direction. The surface of the conical file head 963 is a rough surface to provide the function of a file. The conical file head 963 has a sharp tip 9631 and a pressure end 9632. The size of the sharp tip 9631 is smaller than the diameter of the aperture of the tunnel. The pressure end 9632 is located at the tail end of the conical file head 963, which is the location where it connects with the long-pole portion 962. The pressure end 9632 is designed as a shallow concave on the surface of the tail end away from the sharp tip 9631. The shallow concave of the pressure end 9632 is convenient for the operator's finger (e.g., thumb) to press on the tail end surface of the pressure end 9632 to apply pressure to the conical file head 963; and then, the operator can simultaneously swing the handle 961 in order to drive the handle 961 to swing about the conical file head 963 as a pivot. So that, the rough surface of the conical file head 963 can rub the edge and inner surface of the tunnel, so as to achieve the effect of smoothing the inner surface and the edge of the tunnel.

Figure 16:
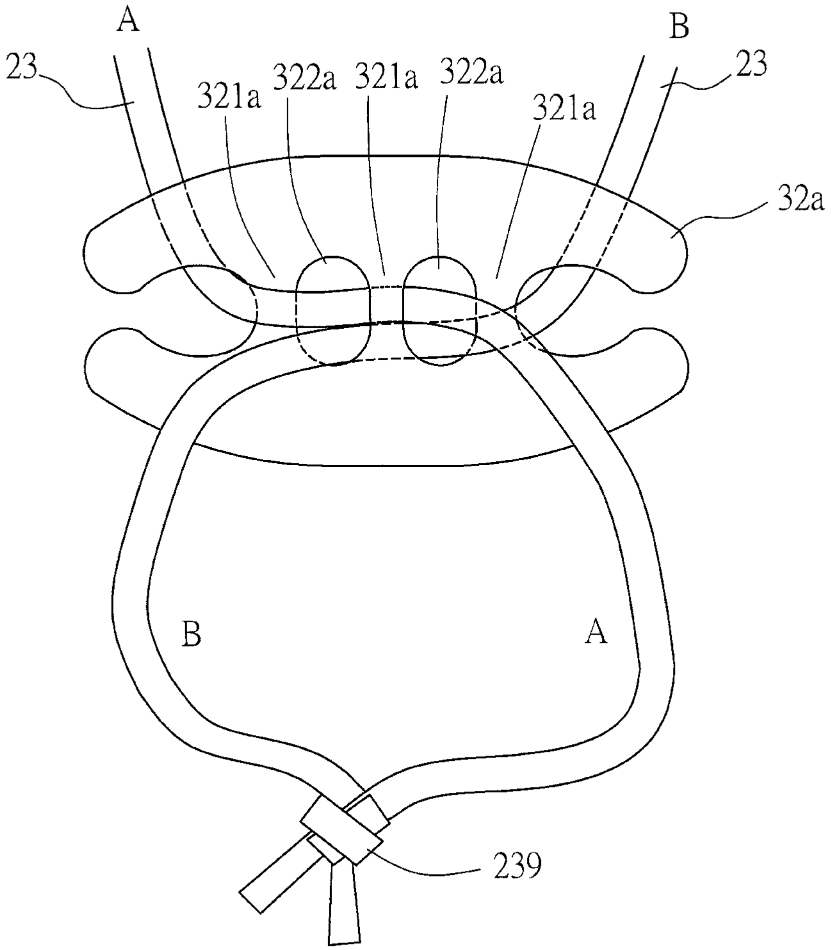
FIG. 16 is a schematic diagram showing an embodiment of a method to tie the suspension ligament on another kind of washer of the T-PAS system of the present invention.

Please refer to FIG. 16, which is a schematic diagram showing an embodiment of a method to tie the suspension ligament on another kind of washer of the T-PAS system of the present invention. The structure of the washer 32*a* shown in this embodiment is almost the same as the washer 32 shown in FIG. 10A and FIG. 10B, and the way to use is also similar. The only difference between these two washers is that, the washer 32*a* shown in FIG. 16 is provided with three bar portions 321*a* and two openings 322*a* formed between the three bar portions 321*a*. In this embodiment, the suspension ligament 23 first passes through the through hole of the pedicle screw (not shown in this figure) such that the pedicle screw is substantially hung on a middle portion of the suspension ligament 23. Then, the free ends of the two strips "A" and "B" of the suspension ligament 23 pass through the tunnel of the lamina (not shown in this figure). After that, the free ends of the two strips "A" and "B" of the suspension ligament 23 pass across the bar portions 321*a* and the two openings 322*a* from two sides of the washer 32*a* and then are tied up with at least 5 knots 239 to ensure the stability of connection between the suspension ligament 23 and the washer 32*a*.

Figure 17:
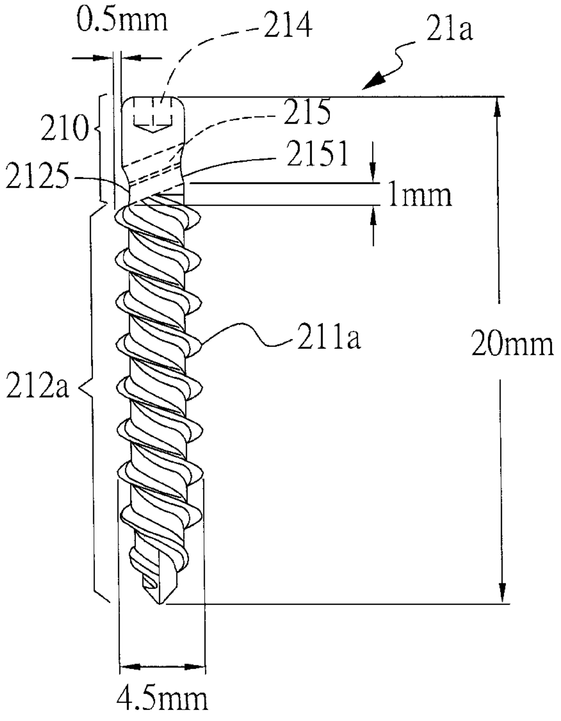
FIG. 17 is a schematic diagram of an embodiment of the pedicle anchor having smooth head portion in the T-PAS system of the present invention.

FIG. 17 is a schematic diagram of an embodiment of the pedicle anchor having smooth head portion in the T-PAS system of the present invention. As shown in FIG. 17, the external thread 212*a* of the columnar body 211*a* of the pedicle anchor 21*a* has only a single thread height and a single thread pitch. The top end of the external thread 212*a* extends to the lower opening 2152 of the through hole 215. The peripheral surface of the columnar body 211*a* between the lower opening 2152 and the top end of the pedicle anchor 21*a* is a smooth head portion 210 without external thread. The outer diameter of the smooth head portion 210 of the columnar body 211*a* is about 1 mm smaller than the outer diameter of the external thread 212*a*, so that a distance (a gap) of about 0.5 mm can be formed at the outermost periphery of the smooth head portion 210 and the outer thread 212*a* of the columnar body 211*a*. In this embodiment, the outer diameter of the external thread 212*a* is about 4.5 mm, the total length of the pedicle anchor 21*a* is about 20 mm, and the distance between the lower edges of the upper and lower openings 2151 and 2152 is about 1 mm.

Figure 18A:
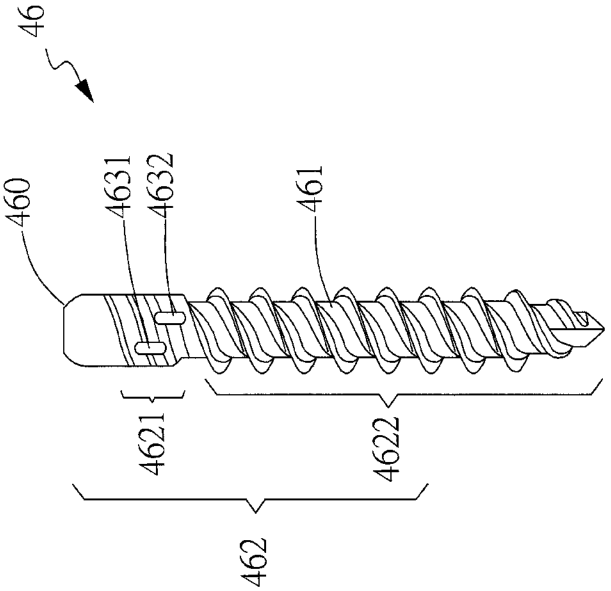
FIG. 18A and FIG. 18B are respectively schematic diagrams of the dual-tunnel suspension pedicle anchor itself and the dual-tunnel suspension pedicle anchor assembled with the suspension ligament of the present invention.
Figure 18B:
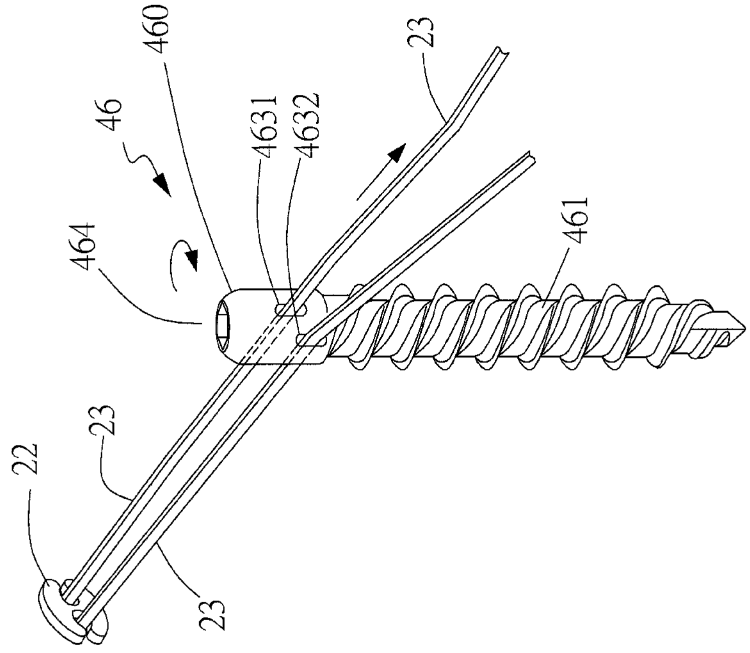

FIG. 18A and FIG. 18B are respectively schematic diagrams of the dual-tunnel suspension pedicle anchor itself and the dual-tunnel suspension pedicle anchor assembled with the suspension ligament of the present invention. The biggest difference between the embodiment shown in FIGS. 18A and 18B and the previous embodiment is that, the pedicle anchor 46 of this embodiment has two horizontal through holes 4631, 4632; and, these two through holes 4631, 4632 are arranged at the upper end of the external thread 462 of the columnar body 461 in a high and low manner, and thus is called as dual-tunnel suspension pedicle anchor 46. As shown in FIG. 18A, the dual-tunnel suspension pedicle anchor 46 has: a long and thin columnar body 461 extending along a central axis, an external thread 462 arranged on the outer surface of the columnar body 461, a fitting structure 464 furnished at a top end 460 of the columnar body 461 (see FIG. 18B), and two horizontal through holes 4631, 4632 horizontally penetrating the columnar body 461. Wherein, the extending direction of the two horizontal through holes 4631, 4632 is perpendicular to the central axis, and are arranged at different height positions of the upper portion of the columnar body 461 in a "one higher" and "the other one lower" manner. In addition, the two horizontal through holes 4631, 4632 are separated by a width in the lateral direction. Moreover, the external thread 462 includes a large thread portion 4622 located at the lower part of the columnar body 461 and a shallow thread portion 4621 closer to the top end 460. In this embodiment, the shallow thread portion 4621 actually only has shallow thread-like grooves without protruding threads. Except for the thread-like grooves, the outer peripheral surface of the shallow thread portion 4621 can be smooth or rough surface. Therefore, when the suspension ligament 23 passes through the horizontal through holes 4631, 4632 and is wrapped around the outer surface of the shallow thread portion 4621 after the through holes 4631, 4632 are buried in the pedicle, the suspension ligament 23 will not be scratched by sharp tip of thread. As shown in FIG. 18B, the two horizontal through holes 4631 and 4632 can respectively allow the two free ends of the suspension ligament 23 to pass through, so that the dual-tunnel suspension pedicle anchor 46 is hung on the suspension ligament 23 for use in the T-PAS operation.

Surgical Technique of Dual-Tunnel Suspension Pedicle Anchor (e.g., L4/5 spinal stenosis)

After decompressive laminotomy of bilateral L4/5, the superior facets of L5 were exposed respectively on both sides in the usual manner as for pedicle screw placement.

A dual-tunnel suspension pedicle anchor 46 was inserted through an entry point made with an awl, and was driven further down into the pedicle and stopped at the level just below the lower horizontal through hole 4632.

Then, the Suspension Ligament was then taken down from the ligament hangers on the sides of the screw driver, and the side with a loop (i.e., closed end) was pulled to the contralateral side of lamina through a bone tunnel created through the "K point" at the arch of lamina.

A pig-nose washer 22 was then cinched and pulled by the suspension ligament 23 from the contralateral side where adequate tension was applied and maintained as the pedicle anchor 46 was driven further down until the upper horizontal through hole 4632 was also buried in the pedicle. Additional tension can be applied to the suspension ligament 23 by driving the pedicle anchor 46 further down if necessary The procedure was repeated on the contralateral side of the lamina, and something worthy of note is the tension is applied only when bilateral pig-nose washers 22 were applied and cinched properly before adequate tension of suspension ligament 23 is to be applied on each side.

Figure 11E:
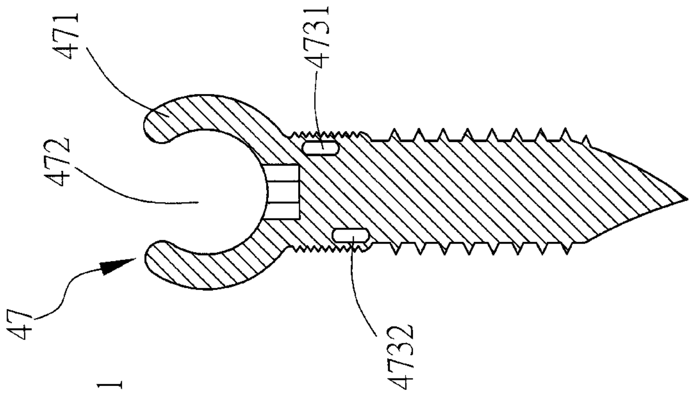
FIG. 11E is a schematic cross-sectional diagram of another embodiment of the dual-tunnel suspension pedicle anchor in the T-PAS system of the present invention.

Please refer to FIG. 11E, which is a schematic cross-sectional diagram of another embodiment of the dual-tunnel suspension pedicle anchor in the T-PAS system of the present invention. The structure of the dual-tunnel suspension pedicle anchor 47 shown in this embodiment is substantially the same as that of the dual-tunnel suspension pedicle anchor 46 shown in FIGS. 18A and 18B, and the method of use is also similar. In the embodiment shown in FIG. 11E, the dual-tunnel suspension pedicle anchor 47 also has: a long and thin columnar body extending along a central axis, an external thread arranged on the outer surface of the columnar body, a fitting structure furnished at a top end of the columnar body, and two horizontal through holes 4731, 4732 horizontally penetrating the columnar body. Wherein, the extending direction of the two horizontal through holes 4731, 4732 is perpendicular to the central axis, and are arranged at different height positions of the upper portion of the columnar body in a "one higher" and "the other one lower" manner. The only difference between the pedicle anchor 47 shown in FIG. 11E and the pedicle anchor 46 shown in FIGS. 18A and 18B is that, a U-shaped rod-holding rack 471 is additionally provided at the top end of the columnar body of the pedicle anchor 47 shown in FIG. 11E. The rod-holding rack 471 has a rod-holding seat 472 for accommodating a connecting rod (not shown in the figure), so that the T-PAS system of the present invention can be used with a conventional spinal fixator. Wherein, the U-shaped rod-holding rack 471 of the pedicle anchor 47 can be a fixed head rod-holding rack or a polyaxial head rod-holding rack.

Figure 19B:
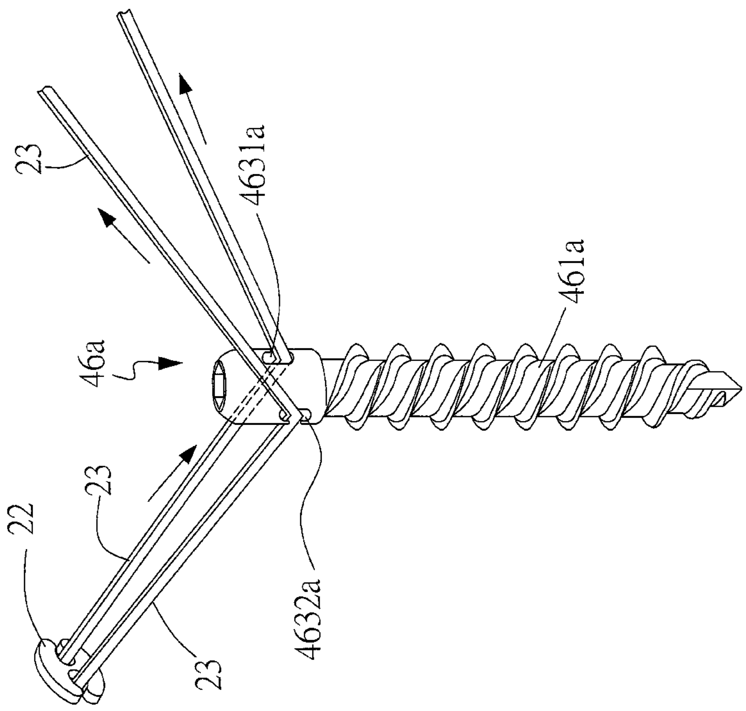
FIG. 19A and FIG. 19B are respectively schematic diagrams of the dual-half-tunnel suspension pedicle anchor itself and the dual-half-tunnel suspension pedicle anchor assembled with the suspension ligament of the present invention.
Figure 19A:
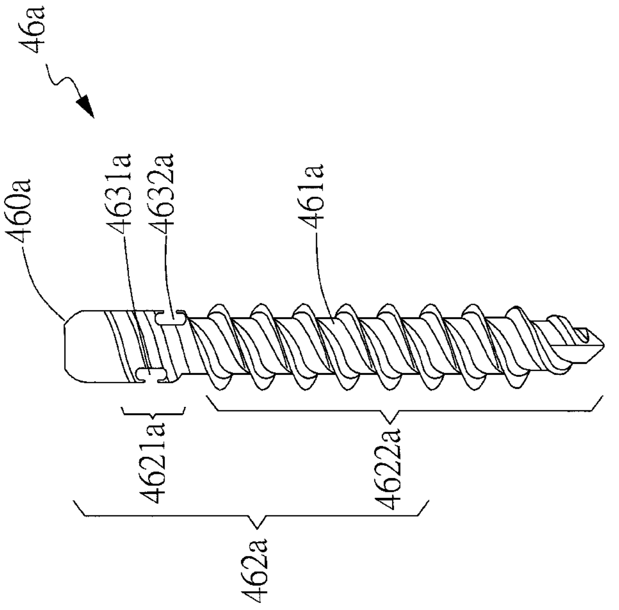

FIG. 19A and FIG. 19B are respectively schematic diagrams of the dual-half-tunnel suspension pedicle anchor itself and the dual-half-tunnel suspension pedicle anchor assembled with the suspension ligament of the present invention. The biggest difference between the embodiment shown in FIGS. 19A and 19B and the previous embodiment shown in FIGS. 18A and 18B is that, the pedicle anchor 46*a* of this embodiment has two groove-shaped horizontal through half-holes 4631*a*, 4632*a*; and, these two through half-holes 4631*a*, 4632*a* are arranged at the upper end of the external thread 462*a* of the columnar body 461*a* in a high and low manner, and thus is called as dual half-tunnel suspension pedicle anchor 46*a*. As shown in FIG. 19A, the dual half-tunnel suspension pedicle anchor 46*a* has: a long and thin columnar body 461*a* extending along a central axis, an external thread 462*a* arranged on the outer surface of the columnar body 461*a*, a fitting structure 464*a* furnished at a top end 460*a* of the columnar body 461*a* (see FIG. 19B), and two groove-shaped horizontal through half-holes 4631*a*, 4632*a* horizontally penetrating the columnar body 461*a*. Wherein, the extending direction of the two horizontal through half-holes 4631*a*, 4632*a* is perpendicular to the central axis, and are arranged at different height positions of the upper portion of the columnar body 461*a* in a "one higher" and "the other one lower" manner. In addition, the two horizontal through half-holes 4631*a*, 4632*a* are separated by a width in the lateral direction. Moreover, the external thread 462*a* includes a large thread portion 4622*a* located at the lower part of the columnar body 461*a* and a shallow thread portion 4621*a* closer to the top end 460*a*. In this embodiment, the shallow thread portion 4621*a* actually only has shallow thread-like grooves without protruding threads. Except for the thread-like grooves, the outer peripheral surface of the shallow thread portion 4621*a* can be smooth or rough surface. Therefore, when the suspension ligament 23 passes through the groove-shaped horizontal through half-holes 4631*a*, 4632*a* and is wrapped around the outer surface of the shallow thread portion 4621*a* after the through holes 4631*a*, 4632*a* are buried in the pedicle, the suspension ligament 23 will not be scratched by sharp tip of thread. As shown in FIG. 19B, the two groove-shaped horizontal through half-holes 4631*a* and 4632*a* can respectively allow the two free ends of the suspension ligament 23 to pass through, so that the dual half-tunnel suspension pedicle anchor 46*a* is hung on the suspension ligament 23 for use in the T-PAS operation.

Surgical Technique of Dual Half-Tunnel Suspension Pedicle Anchor (e.g., L4/5 spinal stenosis)

After decompressive laminotomy of bilateral L4/5, the superior facets of L5 were exposed respectively on both sides in the usual manner as for pedicle screw placement.

A dual half-tunnel suspension pedicle anchor 46*a* was inserted through an entry point made with an awl, and was driven further down into the pedicle and stopped at the level just below the lower edge of the lower half-hole 4632*a*.

The loop-end (closed end) of the suspension ligament was pulled to the contralateral side of lamina through a bone tunnel created through the "K point" at the arch of lamina.

A pig-nose washer 22 was then cinched and pulled by the suspension ligament 23 from the contralateral side where adequate tension was applied to stabilize the washer 22 on the contralateral cortical wall of lamina.

The free ends of suspension ligament 23 on the ipsilateral side were fit into the half-tunnels (half-holes 4631*a*, 4632*a*) through the open side of the half-tunnel with adequate tension maintained as the pedicle anchor 46*a* was driven further down until the upper half-tunnel (half-hole 4632*a*) was also buried in the pedicle. Additional tension can be applied to the suspension ligament 23 by driving the pedicle anchor 46*a* further down if necessary.

The procedure was repeated on the contralateral side of the lamina, and something worthy of note is the tension is applied only when bilateral pig-nose washers 22 were applied, cinched and stabilized properly before adequate tension of suspension ligament 23 is to be applied on each side.

Advantage of Dual Half-Tunnel Suspension Pedicle Anchor 46*a:*

Figure 11F:
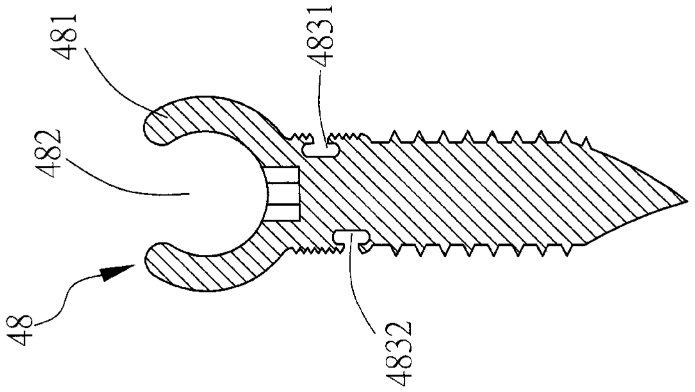
FIG. 11F is a schematic cross-sectional diagram of another embodiment of the dual-half-tunnel suspension pedicle anchor in the T-PAS system of the present invention.

1. Ease of use: the loop-end (closed-end) of suspension ligament can be passed through the lamina tunnel, and the pig-nose washer can be stabilized easier on the contralateral side of lamina when the suspension ligament is not tethered to the pedicle anchor 46; i.e., the washer, suspension ligament and pedicle anchor are packed separately and can be assembled easier.
2. Use regular screw driver: no need to use a screw driver with ligament hangers Please refer to FIG. 11F, which is a schematic cross-sectional diagram of another embodiment of the dual-half-tunnel pedicle anchor in the T-PAS system of the present invention. The structure of the dual half-tunnel suspension pedicle anchor 48 shown in this embodiment is substantially the same as that of the dual half-tunnel suspension pedicle anchor 46*a* shown in FIGS. 19A and 19B, and the method of use is also similar. In the embodiment shown in FIG. 11F, the dual half-tunnel suspension pedicle anchor 48 also has: a long and thin columnar body extending along a central axis, an external thread arranged on the outer surface of the columnar body, a fitting structure furnished at a top end of the columnar body, and two groove-shaped horizontal through half-holes 4831, 4832 horizontally penetrating the columnar body. Wherein, the extending direction of the two horizontal through half-holes 4831, 4832 is perpendicular to the central axis, and are arranged at different height positions of the upper portion of the columnar body in a "one higher" and "the other one lower" manner. The only difference between the pedicle anchor 48 shown in FIG. 11F and the pedicle anchor 46*a* shown in FIGS. 19A and 19B is that, a U-shaped rod-holding rack 481 is additionally provided at the top end of the columnar body of the pedicle anchor 48 shown in FIG. 11F. The rod-holding rack 481 has a rod-holding seat 482 for accommodating a connecting rod (not shown in the figure), so that the T-PAS system of the present invention can be used with a conventional spinal fixator. Wherein, the U-shaped rod-holding rack 481 of the pedicle anchor 48 can be a fixed head rod-holding rack or a polyaxial head rod-holding rack.

The following embodiments of the invention refer to a two-piece suspension pedicle anchor and its system and component-set. The two-piece suspension pedicle anchor comprises a proximal piece and a distal piece that can rotate relatively. An external thread is arranged on the outer surface of the proximal piece, and a transverse through hole for the artificial ligament to pass through is arranged at the distal piece. As the two-piece suspension pedicle anchor is rotated and gradually locked into the bone, only the proximal piece is rotated, and the distal piece with the artificial ligament is pushed down but not rotated; in addition, the artificial ligament will be brought into the bone along with the distal piece and sandwiched between the outer surface of the proximal piece and the bone, that is, the artificial ligament will be sandwiched and fixed between the anchor-bone interface. In this way, the artificial ligament will achieve an ideal tension to dynamically stabilize the facet joint, and the artificial ligament will not wind around the outer surface of the pedicle anchor.

In the translaminar pedicle anchor suspension system (T-PAS system) of the present invention, one end of the artificial ligament is fixed at the pedicle of the lower vertebral segment by a two-piece suspension pedicle anchor, and the other end of the artificial ligament is fixed at the opposite side of the lamina of the upper vertebral segment by a washer, so that the upper vertebral segment and the lower vertebral segment can be suspended through the artificial ligament. By gradually rotating and screwing the two-piece suspension pedicle anchor into the pedicle, the artificial ligament can be pulled, and thus the tension of the artificial ligament can be adjusted. After the operation, the top of the two-piece suspension pedicle anchor will only slightly protrude, or be flush with the surface of the pedicle, or even slightly lower than the surface of the pedicle, which can minimize the patient's foreign body sensation and discomfort. The T-PAS system of the present invention not only can stabilize the structural strength of the spine, but also can avoid the large and protruding pedicle screw used in traditional bone fusion surgery, shorten the operation time, reduce the risk of nerve injury, reduce bleeding, maintain postoperative vertebral mobility, avoid accelerated degeneration of adjacent segments caused by internal fixation and fusion, reduce postoperative foreign body, discomfort, ache and stiffness sensations in patients, and accelerate the patient's recovery time after the vertebral surgery. The component set of T-PAS system the present invention includes the tools and pre-assembled parts that the surgeons need to use when performing the operation, which can facilitate and speed up the process of the surgeons performing the operation.

The following descriptions provide some fundamental illustrations for the Key words, Instruments, Indications, Benefits, and Surgical Techniques regarding to the two-piece suspension pedicle anchor of the T-PAS system of the present invention.

Two-Piece Suspension Pedicle Anchor for Dynamic Stabilization of Facet Joints with T-PAS Technique

Key words

1. Suspension Pedicle Anchor (SPA): The SPA (the anchor with ligament), of which the ligament will be attached to the detachable ligament hangers on the top of the disposable/recyclable inserter.
2. Two-piece Suspension Pedicle Anchor: Length: 2-3.5 cm Diameter: 5-5.5 mm.

3. Proximal piece and distal piece:
   Proximal piece:
   Proximal piece contains screw head and a cannulated tunnel which run from proximally to distally.
   (a) It has a hexagonal recess in the screw head.
   (b) It is about ¾ of total length of anchor.
   (c) The proximal piece has a cannulated tunnel which has diameter 0.1-0.2 mm larger than that of central rod of the inserter which has the diameter of 1.8-2.0 mm. The central rod of the inserter fits into the round recess of the distal piece. The central rod and the stem are freely movable in the cannulated proximal piece and recess of the distal piece.
   Distal piece:
   (a) Its length is about ¼ of total length of anchor.
   (b) Bottom tip of the distal piece should have diameter of 1-1.5 mm less than top of the proximal piece.
   (c) Eyelet size: 1-1.5 mm in diameter.
   (d) Artificial ligament: 2 mm.

Two Major Designs of Distal Piece (Design A & B)

Design A

A distal piece contains a round recess of 1.9-2.1×3 mm on the top. The round recess is used to accommodate the tip of the long central rod which is connected to and controlled by the auto-lock pusher-retractor lever. Thus, the distal pieces along with the long central rod can be pushed down to the bottom of tapped hole by the lever, and the depth is determined by the length of the anchor which will be used. The long central rod can be retracted when the distal piece reaches the bottom of tapped hole.

The proximal piece can be then driven down by the hexagonal driver with its tip placed in the hexagonal recess in the screw head of the proximal piece.

Design B

A "stemmed" distal piece. The distal piece has a long stem which extends from the top of distal piece towards top of the proximal piece just below the hexagonal recess. The distal piece can be pushed down to the bottom of tapped hole and the hexagonal driver is then used to drive the proximal piece down to contact the distal piece. Further tightening of the ligament on the loop-end side can be achieved if the proximal piece is driven to push the distal piece further downward.

Eyelet in the Distal Piece

The eyelet in the distal piece is 1.5-2 mm in diameter which allows free movement of the ligament during the initial insertion of the distal piece into the tapped hole.

Inserter Handle

1. Hexagonal driver: the driver has a hollow central tunnel which allows free movement of the central rod.
2. Auto-lock pusher and retractor lever (which allows controlled length of movement with each push.)
3. Detachable ligament hangers.
4. Central rod.

Diameter: 1.8-2 mm

Cannulated tunnel (1.9-2.1 mm): (hollow tunnel in screwdriver and proximal piece of the anchor). Used to push the distal piece down to the bottom of tapped hole. The central rod which is proximally connected to and controlled by the auto-lock pusher-retractor lever. Distally, it can reach the round recess of distal piece in design A or it can be used to push the stem of the distal piece in design B.

Surgical Procedure

Posterior Approach

1. Prepare a patient in the prone position and posterior approach to expose the levels to be treated. The midline structure including the spinous processes, supra- and interspinous ligament are well preserved. Planned partial laminectomy.
2. The level of laminae to be decompressed (the upper segment of the motion unit) are exposed and the facet joints (superior facet of the lower motion segment) on both sides at the level to be treated are also exposed. Partial laminectomy can done in a conventional manner using Kerrison Rongeur or the Misonix Bone Scalpel to remove lower lamina, medial facet, lateral recess and part of the upper lamina of the lower segment. The procedure of partial laminectomy must be carefully planned and should be precise to preserve enough bone stock of lamina and spinous process for the TPAS procedure.

Laminar Tunnel

3. A transverse laminar tunnel is created (using 2 mm power burr or the hook of Misonix) through the rigid portion of the roof of lamina which is defined as a point located at the junction where base spinous process meets the roof of lamina. The point can be defined as an intersection of two imaginary lines by palpating the lamina from lateral lamina upward to medial cortical wall, and from lower rostral lamina upward to medial cortical wall of lamina which is usually located between the upper ¼ to ⅓ of the junction of lamina and spinous process. The point is considered rigid, and is an ideal location to anchor the pig-nose washer to withstand the tension of the artificial ligament from the contralateral Suspension Pedicle Anchor (SPA).

Tapped Hole

4. The hole for the anchor is pre-drilled with a tap in the appropriate location of the pedicle of the lower segment to the appropriate depth which is usually 5 mm deeper than the depth of the anchor that will be inserted. After a tapped hole is made in the pedicle, the surgeon holds handle of the inserter with the anchor attached to the hexagonal driver. A 2 mm-sized artificial ligament is ideal for stability because it will be two-folded (4 mm) eventually on the loop-end side when the procedure is done; It will have 4 mm width ligament in the anchor-bone interface.
5. The surgeon first detaches the loop end of the Suspension Pedicle Anchor from the ligament hangers on the sides of the handle.
6. Next, the loop end is passed through the lamina tunnel. The loop of the ligament is then passed into the pig-nose washer. The ligament is then pulled gently to tension the pig-nose washer against the contralateral lamia wall.

7. The pig-nose washer acts as an anchor point of the suspension ligament on the contralateral lamina wall, preventing the ligament from pulling back through the tunnel.
8. Once the loop end of the ligament is stabilized with the pig-nose washer on the contralateral side of lamina, the distal piece of suspension anchor can be inserted into the pedicle by pushing the auto-lock pusher-retractor lever.
9. The depth of insertion and the length of extra-length of suspension ligament to be preserved on the loop-end side are determined by the length of anchor which we select.
10. The extra-length of the ligament to be kept on the loop-end side is usually about 50-60% of the total length of the anchor (also depends on the size of distal piece and the initial depth of insertion of the anchor at the entry of tapped hole and the tapering design of the anchor), and which is measured when the tip of distal piece is placed at the entry of tapped hole, and a marking pen is used to mark the ideal length on the free-end side to be preserved on the loop-end side.
11. The ligament will be pulled from the free-end side toward the loop-end side until the marker aligned with the eyelet. A ligament puller which is either a hemostat or any bone hook to maintain the tension of extra length on the loop end side while an assistant maintains the ligament tension on the free end side by holding the end of the free-end side as the tip of distal anchor is placed at the entry of tapped hole.
12. The tip of the distal piece is then placed into the entry of tapped hole down to the bottom of tapped hole when the auto-lock pusher-retractor lever pushes the central rod downward with a controlled depth to be reached. The ligament is temporarily held in position in the tapped hole, and the ligament on the free-end side can be released and cut with 1 cm left after the auto-lock pusher-retractor mechanism retracts, and proximal piece is driven down with the hexagonal driver to meet the distal piece.
13. A certain tightness on the loop-end side of ligament is now achieved when the proximal piece is driven to meet the distal piece. Tension of the ligament on the loop-end side can be increased if the anchor is driven further down with hexagonal driver.
14. The ideal tension of ligament on the loop-end side is 10 N/M which can allow 1-2 mm motion of the facet joints, and the tightness of ligament on the loop-end side can be evaluated by pressing with the index finger to see if it doesn't move more than 2 mm which suggests enough tightness.
15. The stability of facet joints can be tested by observing the motion of facet joints when the spinous process of the upper segment is gently pulled up with towel clips In other embodiments of the two-piece suspension pedicle anchor of the present invention described below, since the structure and function of most of the elements are the same as those of the previous embodiments, the same or similar elements will be directly given the same names and numbering, and the details of its structure and function will not be repeated.

Figure 20A:
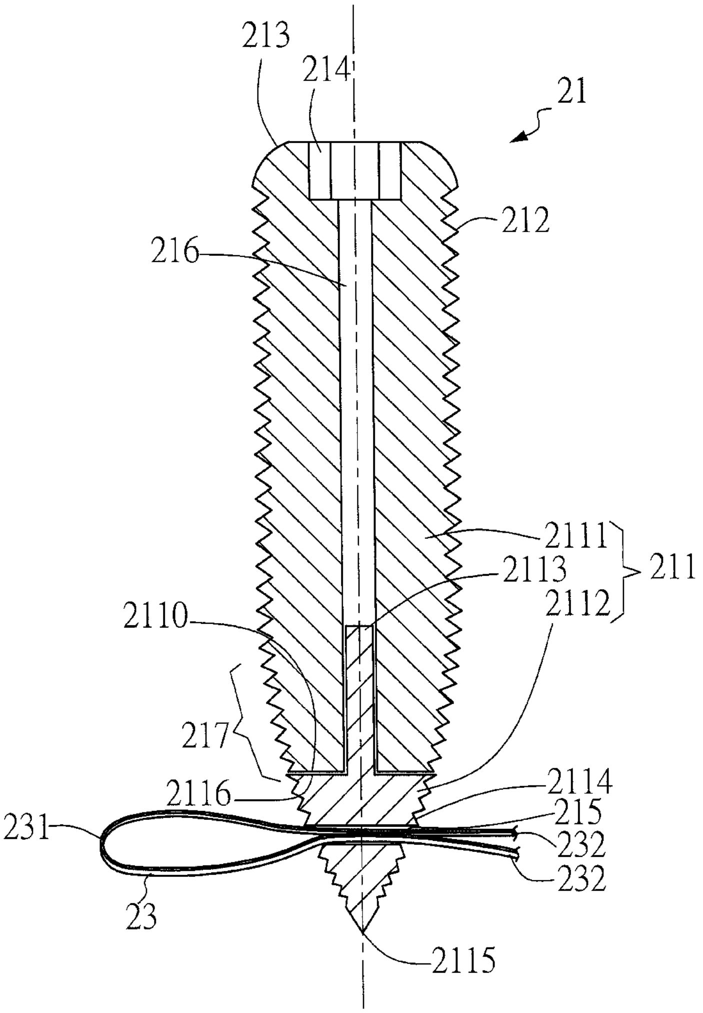
FIG. 20A and FIG. 20B are respectively a cross-sectional schematic diagram and a three-dimensional schematic diagram of the first embodiment of the two-piece suspension pedicle anchor according to the present invention.
Figure 20B:
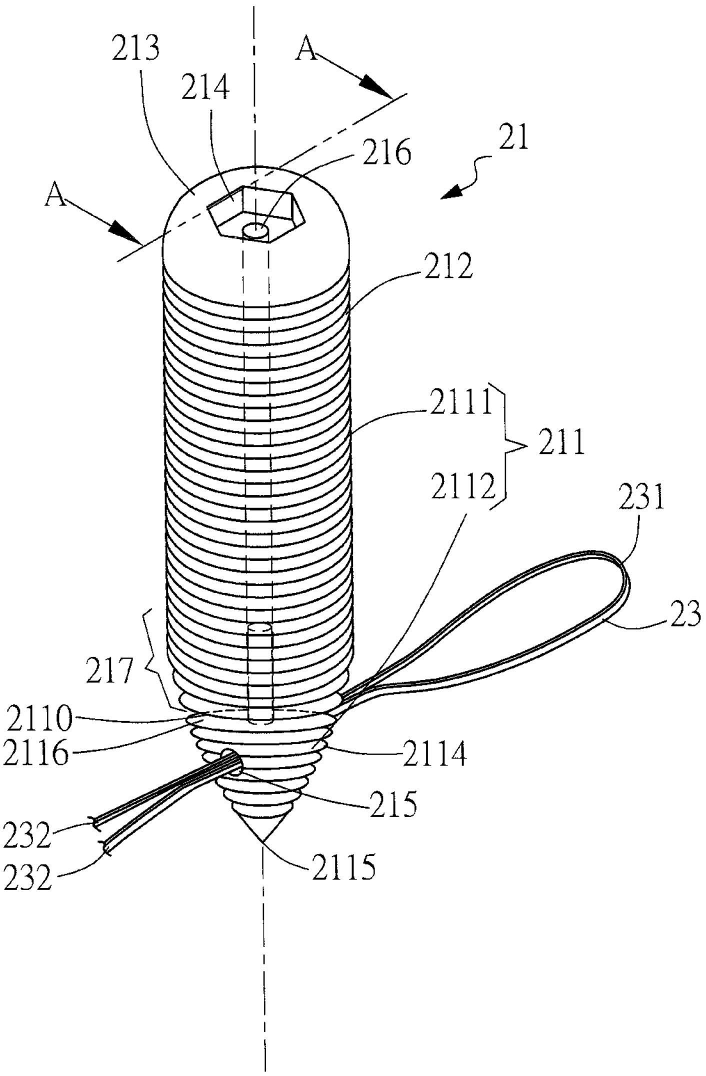

Please refer to FIG. 20A and FIG. 20B, which are a cross-sectional schematic diagram and a three-dimensional schematic diagram of the first embodiment of the two-piece suspension pedicle anchor according to the present invention, respectively. In the first embodiment, the two-piece suspension pedicle anchor 21 of the present invention comprises: a columnar body 211, an external thread 212, a fitting structure 214 and a through hole 215. The columnar body 211 is an elongated cylinder extending along a central axis. The external thread 212 is disposed on an outer surface of the columnar body 211. The fitting structure 214 is arranged at a top end 213 of the columnar body 211. The through hole 215 laterally penetrates through the columnar body 211. The feature of the two-piece suspension pedicle anchor 21 of the present invention is that the columnar body 211 includes a proximal piece 2111 and a distal piece 2112 to present a two-piece columnar structure. The distal piece 2112 is assembled at a bottom end 2110 of the proximal piece 2111, and the proximal piece 2112 is rotatable relative to the distal piece 2111 according to the central axis. The fitting structure 214 is disposed on the top end 213 of the proximal piece 2111 at a position away from of the distal piece 2112. The external thread 212 of the columnar body 211 is disposed at least on the outer surface of the proximal piece 2111. The through hole 215 is disposed on the distal piece 2112, and the extending direction of the through hole 215 is not parallel to the central axis. The bottom end 2110 of the proximal piece 2111 is provided with a central rod hole 216 extending along the central axis toward the top end 213. A top end 2116 of the distal piece 2112 is provided with a central rod 2113 protruding along the direction of the central axis. The size and position of the central rod 2113 correspond to the central rod hole 216, and the central rod 2113 is inserted into the central rod hole 216. Therefore, the distal piece 2112 and the proximal piece 2111 can be assembled into the columnar body 211 by inserting the central rod 2113 into the central rod hole 216; in addition, the proximal piece 2111 can rotate relative to the distal piece 2112 according to the central axis. The bottom end 2115 of the distal piece 2112 is the bottom end of the entire columnar body 211 and presents a sharp cone or conical head structure. The through hole 215 located at the distal piece 2112 can allow an artificial ligament 23 to pass through, so that the two-piece suspension pedicle anchor 21 can be hung on the artificial ligament 23. The fitting structure 214 at the top end 213 of the proximal piece 2111 can be assembled with the front end of the screwdriver 92.

Figure 23:
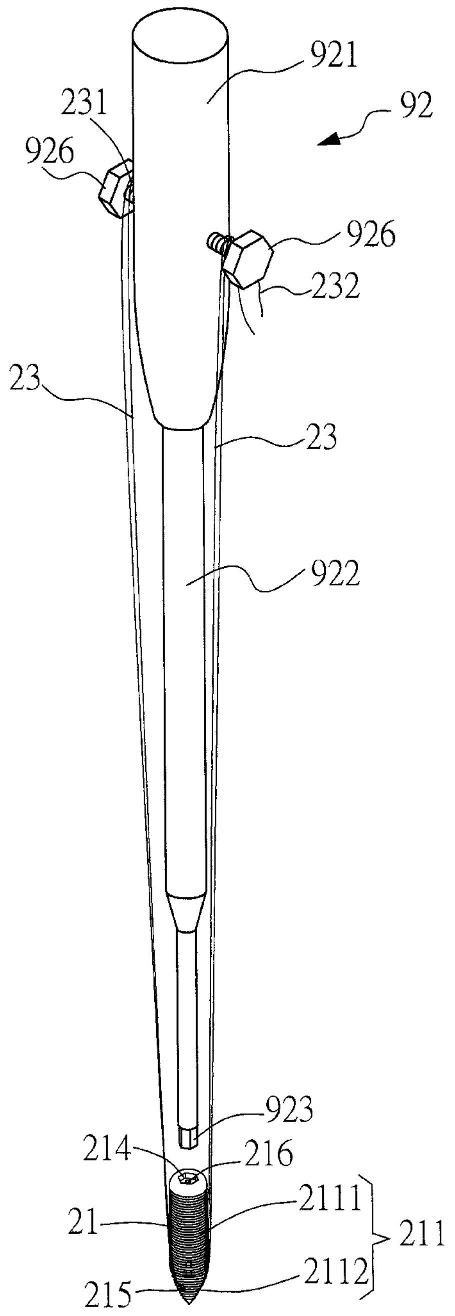
FIG. 23 is a schematic diagram of an embodiment of a screwdriver in the component set of the T-PAS system of the present invention.

In this embodiment, the fitting structure 214 is a hexagonal socket, the outline and size of which are corresponding to the hexagonal protruding driver head 923 of the screwdriver 92 (as shown in FIG. 23). When the screwdriver 92 is operated to drive the two-piece suspension pedicle anchor 21 to rotate around the central axis, the two-piece suspension pedicle anchor 21 can be screwed and locked into a pre-drilled bone hole in the bone; thereby, a part of the artificial ligament 23 is clamped and fixed between the outer surface of the proximal piece 2111 and the surface of the bone hole in the bone. Since the proximal piece 2111 can rotate relative to the distal piece 2112 according to the central axis, therefore, when the screwdriver 92 is operated, the two-piece suspension pedicle anchor 21 is driven to rotate about the central axis and is gradually locked into the bone hole of the bone; in the meantime, only the proximal piece 2111 will be rotated by the screwdriver 92, and the distal piece 2112 will not be rotated by the screwdriver 92. Therefore, the artificial ligament 23 passing through the through hole 215 of the distal piece 2112 does not rotate nor wrap around the outer surface of the proximal piece 2111. The artificial ligament 23 only extends straight and is clamped and fixed between the outer surface of the proximal piece 2111 and the inner surface of the bone hole of the bone.

In the present invention, the method of inserting the artificial ligament 23 into the through hole 215 of the distal piece 2112 is that, firstly, a middle section of the suspension ligament 23 is folded into a double-line side-by-side structure and has a closed end 231 at the folded section and an open end 232 away from the folded section. Then, insert the closed end 231 of the suspension ligament 23 from one side of the through hole 215 of the distal piece 2112 and pull out from the other side; such that the two ends (also called the tail open end 232 or the free end) of the artificial ligament 23 that are away from the closed end 231 are located on the same side of the through hole 215, while the closed end 231 is located on the other side of the through hole 215.

In one embodiment, the extending direction of the through hole 215 of the distal piece 2112 is perpendicular to the central axis. A tapered portion with a tapered outer diameter is provided at the portion of the proximal piece 2111 that is closer to the distal piece 2112. The length of the tapered portion in the direction of the central axis is preferably less than ¼ of the total length of the columnar body 211. In addition, the shape of the distal piece 2112 presents a conical structure similar to a bullet head. The maximum outer diameter of the top end 2116 of the distal piece 2112 is approximately equal to or slightly smaller than the minimum outer diameter of the bottom end 2110 of the proximal piece 2111; such structure can facilitate surgeons to perform the operations of inserting the two-piece suspension pedicle anchor 21 into the pre-drilled bone hole and locking the two-piece suspension pedicle anchor 21 into the bone hole. In this embodiment, the outer surface of the distal piece 2112 is provided with an external thread 212 in the same direction as the outer surface of the proximal piece 2111; however, in other embodiments, the outer surface of the distal piece 2112 can also be provided with a rough surface or a smooth surface without any external screw thread.

In one embodiment, the artificial ligament 23 is pre-assembled in the through hole 215 of the distal piece 2112 of the two-piece suspension pedicle anchor 21 at the factory end for packaging and sales. Therefore, the doctor does not need to perform the threading and assembly work of the artificial ligament 23 and the two-piece suspension pedicle anchor 21 when using it. The outer diameter of the proximal piece 2111 in the area closer to the fitting structure 214 is greater than the maximum outer diameter of the proximal piece 2111. The proximal piece 2111 has a tapered section 217 near the distal piece 2112, such that the outer diameters of the adjacent parts of the proximal piece 2111 and the distal piece 2112 are approximately the same; and moreover, the appearance of the entire columnar body 211 roughly presents the appearance of a bullet. In this embodiment, the outer surface 2114 of the distal piece 2112 is provided with external threads. However, in another embodiment not shown in the figure, the outer surface 2114 of the distal piece 2112 may also be a rough surface or a smooth surface, and no external screw thread is provided.

Figure 21:
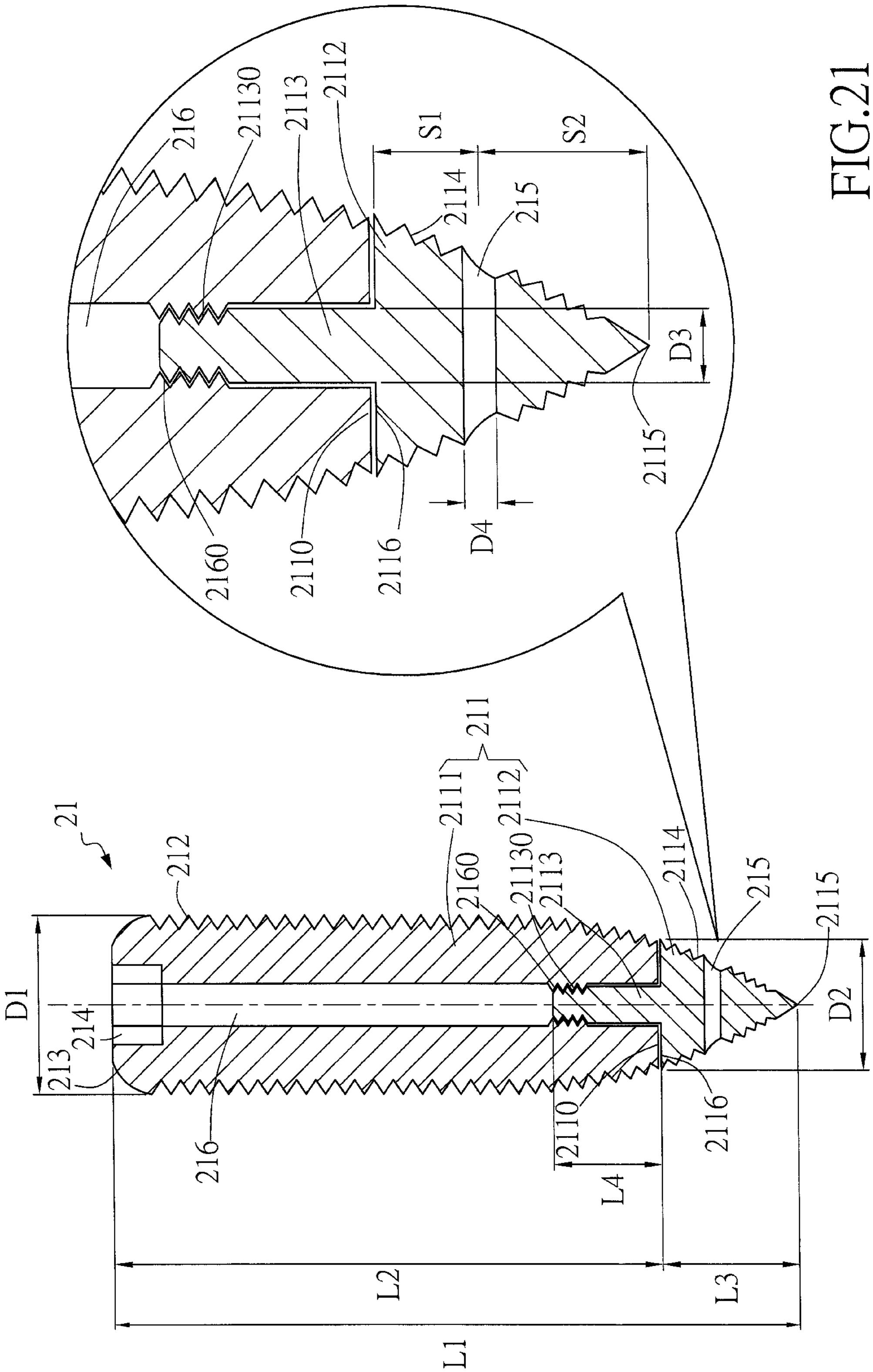
FIG. 21 is a schematic cross-sectional view and a partial enlarged view of the second embodiment of the two-piece suspension pedicle anchor of the present invention.

Please refer to FIG. 21, which is a schematic cross-sectional view and a partial enlarged view of the second embodiment of the two-piece suspension pedicle anchor of the present invention. In this embodiment, the two-piece suspension pedicle anchor 21 also comprises: a columnar body 211, an external thread 212, a fitting structure 214 and a through hole 215; in addition, the columnar body 211 is also composed of a proximal piece 2111 and a distal piece 2112. The differences between this second embodiment the previously illustrated first embodiment include the followings. In the second embodiment of the two-piece suspension pedicle anchor 21 shown in FIG. 21, a rod top external thread 21130 is provided on a top of the central rod 2113 of the distal piece 2112. In the central rod hole 216 of the proximal piece 2111, a rod hole internal thread 2160 that can engage with the rod top external thread 21130 is provided at a position relative to the rod top external thread 21130. Wherein, the thread direction of the rod top external thread 21130 and the thread direction of the external thread 212 of the columnar body 21 are opposite; that is, the rod top external thread 21130 is the "reverse thread" of the external thread 212. In this embodiment, the number of thread turns of the rod top external thread 21130 is only a few turns, such as but not limited to: 3 turns; however, the number of thread turns of the rod hole internal thread 2160 can be the same or more than the number of thread turns of the rod top external thread 21130. Therefore, when the screwdriver 92 is used to "forwardly rotate" (e.g., rotate clockwise) the two-piece suspension pedicle anchor 21 of the present invention and screw it down into the bone hole of the bone, the rod top external thread 21130 has a tendency to "loosen and unscrew" from the rod hole internal thread 2160; it is due to that, the thread direction of the rod top external thread 21130 is opposite to the thread direction of the external threads 212 on the surface of the proximal piece 2111. Thus, the distal piece 2112 will only be pushed down into the bone hole by the proximal piece 2111, but "will not" be driven to rotate by the screwdriver 92 along with the proximal piece 2111. Thereby, the artificial ligament 23 passing through the through hole 215 of the distal piece 2112 will be pulled into the bone together by the two-piece suspension pedicle anchor 21 that is gradually screwed into the bone, and then clamped between the outer surface of the proximal piece 2111 and the inner surface of the bone hole of the bone, but the artificial ligament 23 does not rotate along with it and does not wrap around the outer surface of the proximal piece 2111. On the contrary, when the screwdriver 92 is used to "reversely rotate" (e.g., rotate counterclockwise) the two-piece suspension pedicle anchor 21 of the present invention and screw it upwards out of the bone, the rod top external thread 21130 has a tendency to "lock-in and screw-in" the rod hole internal thread 2160; thus, the distal piece 2112 "will" be driven in rotation by the screwdriver 92 and taken out of the bone together with the proximal piece 2111. It does not happen that only the proximal piece 2111 is taken out of the bone, but the distal piece 2112 remains in the bone hole of the bone. Therefore, in some cases, when the proximal and distal pieces of the anchor must be removed (for example, but not limited to: the artificial ligament is not in ideal tension and must be reset, or the entire anchor must be removed from the vertebra when re-operation is required), the "reverse thread" design facilitates the removal of the distal piece of the anchor.

In the present invention, several two-piece suspension pedicle anchors 21 of different sizes and specifications can be produced in advance in order to adapt to different vertebrae sizes or structures of different patients or different surgical needs. Generally speaking, for the two-piece suspension pedicle anchors 21 used in the T-PAS system 20 of the present invention, as shown in FIG. 21, the largest outer diameter D1 of the columnar body 211 is applicable between 3.5 mm-7.5 mm but is preferably between 5.5 mm~7.5 mm; the largest outer diameter D2 of the distal piece 2112 is applicable between 2.5 mm-4.5 mm but is preferably between 2.5 mm~3.5 mm; wherein D2<D1; the total length L1 of the columnar body 211 is applicable between 20 mm-65 mm but is preferably between 25 mm~65 mm; a preferred embodiment of the length L2 of the proximal piece 2111 is that L2 is approximately equal to ¾ times L1; a preferred embodiment of the length L3 of the distal piece 2112 (excluding the central rod 2113) of the columnar body 211 is that L3 is approximately equal to ¼ times L1. An exemplary embodiment of the length L4 of the central rod 2113 of the distal piece 2112 of the columnar body 211 is more than 5 mm, and the length L4 of the central rod 2113 can even extend up to the lower side of the fitting structure 214 of the top end 213 of the proximal piece 2111. In this preferred embodiment, the length L4 of the central rod 2113 is between 5 mm~10 mm. A preferred embodiment of the diameter D3 of the central rod 2113 of the distal piece 2112 is between 1.5 mm~2 mm. The inner diameter of the central rod hole 216 of the proximal piece 2111 of the columnar body 211 is slightly larger than the diameter D3 of the central rod 2113. A preferred embodiment of the diameter D4 of the through hole 215 of the distal piece 2112 of the columnar body 211 is between 1.5 mm~2 mm. A preferred embodiment of the distance S1 between the centerline of the through hole 215 and the top end 2116 of the distal piece 2112 is between 4 mm~5 mm. A preferred embodiment of the distance S2 between the centerline of the through hole 215 and the bottom end 2115 of the distal piece 2112 is between 3 mm~4 mm. In the present invention, the central rod hole 216 of the proximal piece 2111 of the columnar body 211 may be a countersunk hole or a through hole extending upward from the bottom end 2110 of the proximal piece 2111 along the central axis.

Figure 22A:
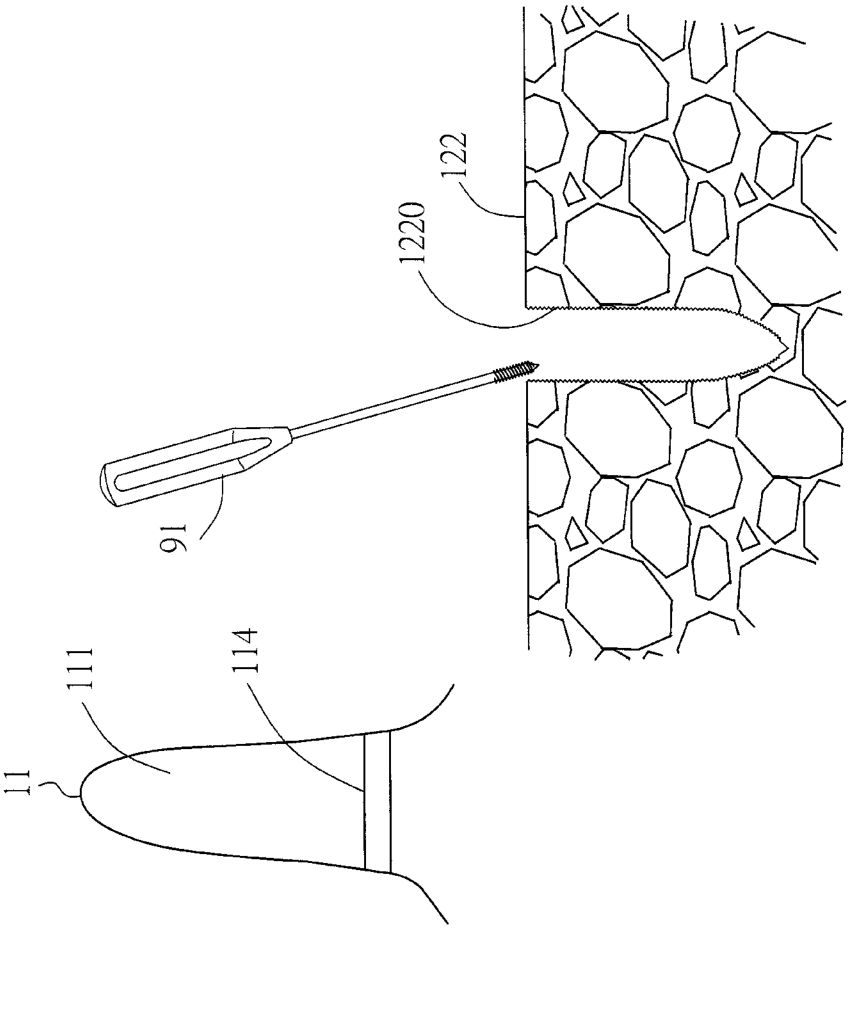
FIG. 22A, FIG. 22B and FIG. 22C are schematic diagrams respectively showing three steps of a method for fixing the two-piece suspension pedicle anchor to the pedicle of the lower vertebral segment in the T-PAS system of the present invention.
Figure 22B:
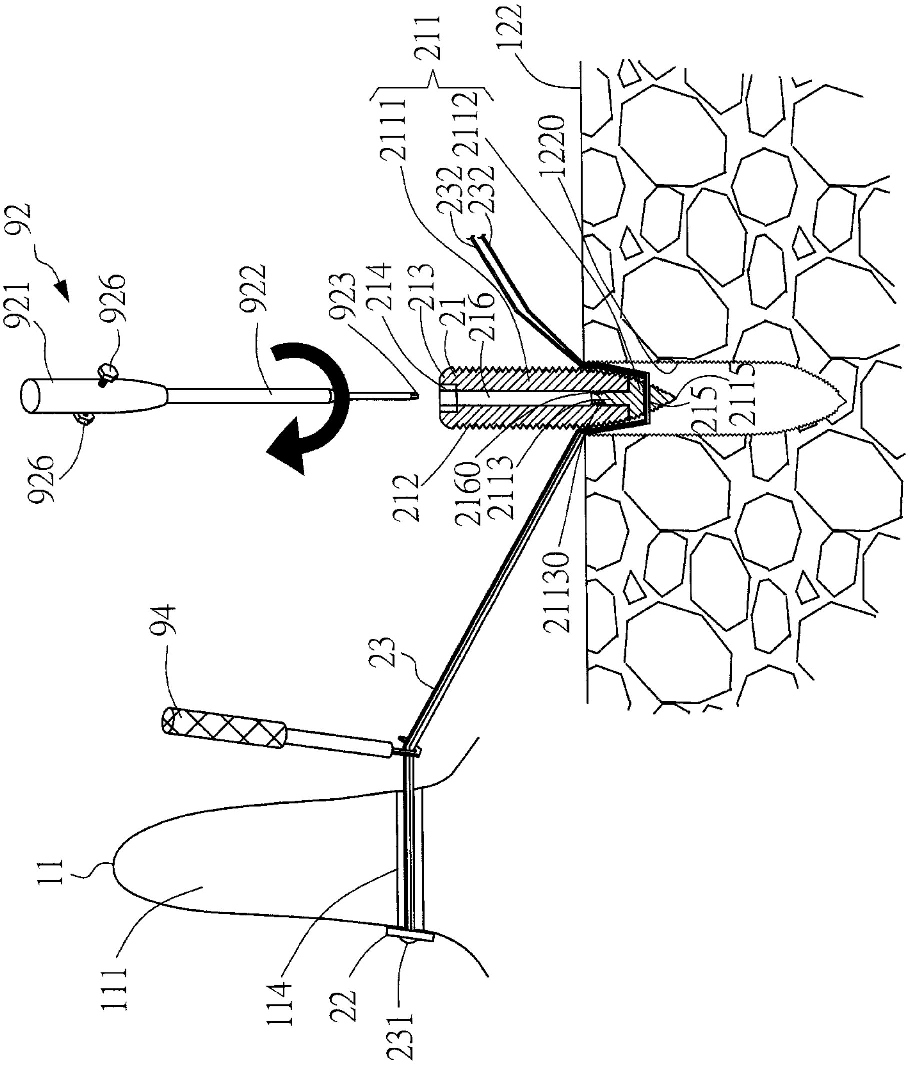
Figure 22C:
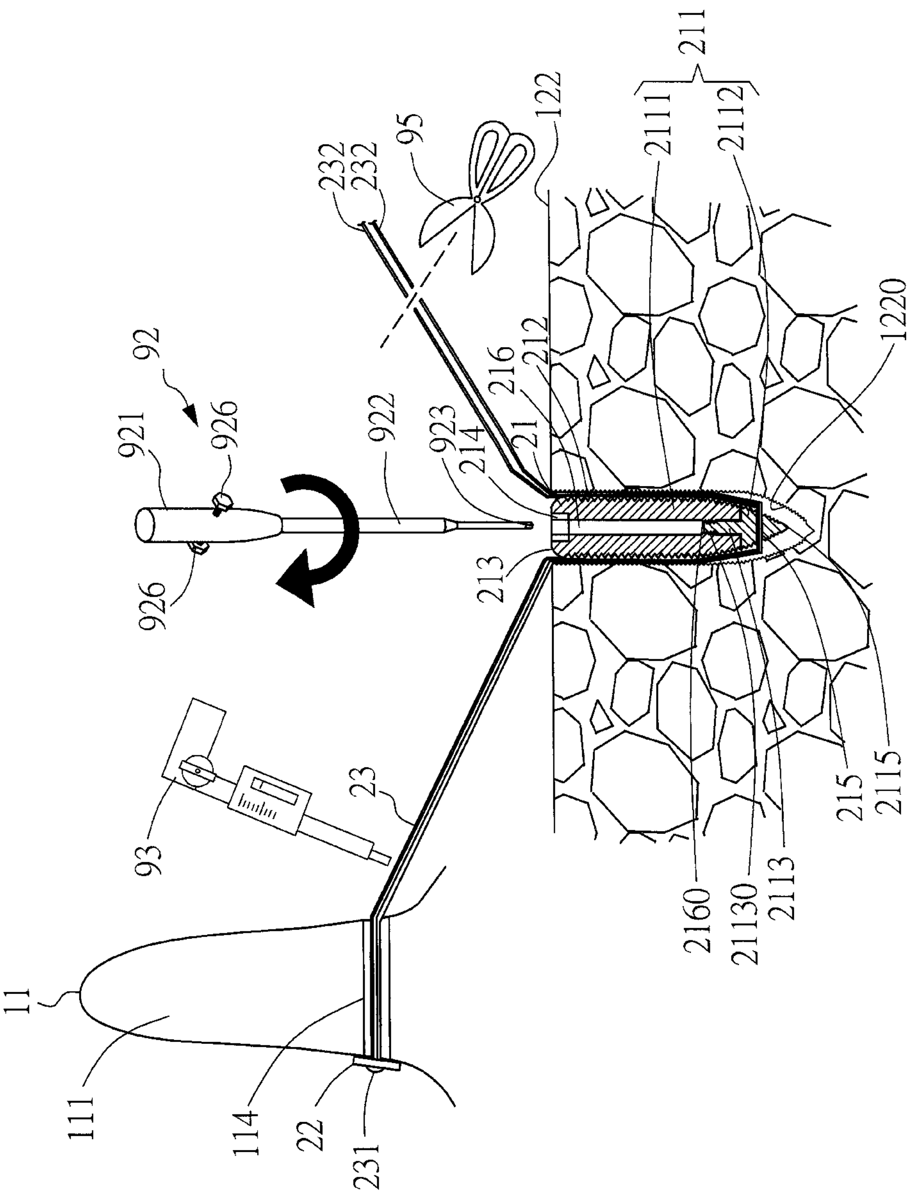

Please refer to FIG. 22A, FIG. 22B and FIG. 22C, which are schematic diagrams respectively showing three steps of a method for fixing the two-piece suspension pedicle anchor to the pedicle of the lower vertebral segment in the T-PAS system of the present invention. First, as shown in FIG. 22A, drilling a bone hole 1220 (also referred as tapped hold) with a predetermined diameter and a predetermined depth in the pedicle 122 of the lower vertebral segment 12 by using a drilling tool 91 such as a chisel or a drill (either manual or electric), and drilling a tunnel 114 with a predetermined diameter in the lamina 111 of the upper vertebral segment 11. Wherein, the inner diameter of the bone hole 1220 should be slightly smaller than the outer diameter of the proximal piece 2111 of the two-piece suspension pedicle anchor 21 by about 0.25 mm~0.5 mm; in addition, the depth of the bone hole 1220 is more than 5 mm more than the total length of the columnar body 211 of the two-piece suspension pedicle anchor 21. Next, as shown in FIG. 22B, the lower half of the two-piece suspension pedicle anchor 21 with the smaller outer diameter distal piece 2112 (together with the artificial ligament 23 passing through the through hole 215) and a part (approximately 30%~40% of the length) of the proximal piece 2111 is tapped into the bone hole 1220. At this stage, there is still a relatively large part (about 60%~70% of the length) of the proximal piece 2111 that is exposed outside the bone hole 1220 of the pedicle 122 of the lower vertebral segment. Then, the closed end 231 of the artificial ligament 23 is passed through the tunnel 114 of the lamina 111 of the upper vertebral segment 11 in the same manner shown in FIG. 6A and FIG. 6B and connected to the washer 22. And then, the artificial ligament 23 is lightly pulled from the tail open end 232 of the artificial ligament 23, and at the same time, a portion of the artificial ligament 23 between the washer 22 and the two-piece suspension pedicle anchor 21 is also lightly pulled by using the hook 94 to provide an appropriate length of remaining line, until the pulled portion of the artificial ligament 23 between the washer 22 and the two-piece suspension pedicle anchor 21 also has a relatively small first tension (not in a loosened state), while the washer 22 is pulled against the opening of the tunnel 114 of the lamina 111 due to the first tension of the artificial ligament 23. In this step, the length of the so-called remaining line of the artificial ligament 23 is determined and adjusted according to: (1) different lengths of the two-piece suspension pedicle anchors 21, (2) the depths to which the two-piece suspension pedicle anchors 21 are initially tapped into the bone hole 1220, and (3) the tightness of the artificial ligament 23, so that after the procedure of locking the two-piece suspension pedicle anchor 21 into the bone hole 1220 is completed, the tension value of the artificial ligament 23 can fall within the range of the predetermined tension. The predetermined tension is greater than the aforementioned first tension. Specifically, if the two-piece suspension pedicle anchor 21 is initially tapped and inserted into the bone hole 1220 to a deeper depth, the first tension can be tightened a little; however, if the two-piece suspension pedicle anchor 21 is tapped into the bone hole 1220 to a shallow depth at first, then the artificial ligament 23 needs to be lightly hooked with the hook 94 to leave some remaining line depending on the user's experience, in order to avoid the tension of the artificial ligament 23 being too tight when the two-piece suspension pedicle anchor 21 is further locked down into the bone hole 1220 later.

Then, as shown in FIG. 22B, the proximal piece 2111 of the two-piece suspension pedicle anchor 21, which is still exposed outside the bone hole 1220, is gradually rotated downward and locked into the bone hole 1220 by using the screwdriver 92. At this moment, the artificial ligament 23 is passed through the through hole 215 of the distal piece 2112, and is abutted on the outer surface of the proximal piece 2111 of the two-piece suspension pedicle anchor 21, and thus will be gradually pushed into the bone hole 1220 together with the proximal piece 2111. As the depth of the proximal piece 2111 and the artificial ligament 23 locked into the bone hole 1220 gradually increases, the artificial ligament 23 between the washer 22 and the two-piece suspension pedicle anchor 21 will also gradually shorten and tighten, and thereby the tension of the artificial ligament 23 between the washer 22 and the two-piece suspension pedicle anchor 21 will be gradually increased. Until about 50%~60% of the length of the proximal piece 2111 is locked (embedded) into the bone hole 1220, as shown in FIG. 22C, the tension gauge 93 can be used to measure (or the doctor can use the finger to detect by experience) whether the tension of the artificial ligament 23 between the washer 22 and the two-piece suspension pedicle anchor 21 has reached the range of predetermined tension. If the tension is still insufficient, use the screwdriver 92 to continue to lock the proximal piece 2111 downward into the bone hole 1220 until the tension of the artificial ligament 23 reaches the range of predetermined tension. Generally speaking, when the step shown in FIG. 22C is completed, most of the columnar body 211 of the two-piece suspension pedicle anchor 21 will be locked (embedded) into the bone hole 1220 of the pedicle 122 of the lower vertebral segment; and, the top end 213 of the proximal piece 2111 of the two-piece suspension pedicle anchor 21 only slightly protrudes or is flush with the surface of the pedicle 122. Specifically, after the procedure of fixing the two-piece suspension pedicle anchor 21 to the pedicle 122 of the lower vertebral segment is completed, the height of the top end 213 of the proximal piece 2111 protruding from the surface of the pedicle 122 should be less than 5 mm or even flush with the surface of the pedicle 122. Finally, the excess artificial ligament 23 (tail open end 232) still exposed outside the pedicle 122 is severed by using scissors 95 or a scalpel.

Similarly, the two-piece suspension pedicle anchor 21 on the other side is also locked into the pedicle 123 and provides a predetermined tension to the artificial ligament 23 (suspension wire) in the same manner and steps. When the operation of locking the two-piece suspension pedicle anchor 21 into the pedicle 123 is completed, the top end 213 of the two-piece suspension pedicle anchor 21 will only slightly protrude, even flush with the surface of the pedicle 123. After the T-PAS system 20 of the present invention is installed, only two two-piece suspension pedicle anchors 21 need to be screwed into the pedicles 122, 123 of the lower vertebral segment 12, and the top end 213 of each two-piece suspension pedicle anchor 21 is either flush with the surface of the pedicle 122 or only slightly protruding beyond the surface of the pedicle 122; generally speaking, the height of the top end 213 of the two-piece suspension pedicle anchor 21 protruding beyond the surface of the pedicle 122 will not be higher than 5 mm. In addition, the washer 22 is also a thin-plate structure and is attaching on the side-surface of the lamina, such that the patient won't feel uncomfortable or foreign body sensation. Moreover, the suspension wire composed of artificial ligament 23 will not cause discomfort or pain to the patient, which does improve all the shortcomings of conventional technologies.

Please refer to FIG. 23, which is a schematic diagram of an embodiment of a screwdriver in the component set of the T-PAS system of the present invention. Because the T-PAS system of the present invention uses a slender, soft and tough artificial ligament 23 as a suspension wire, in order to prevent the artificial ligament 23 (suspension wire) from accidentally intertwining with each other or on the screwdriver 92 when locking the two-piece suspension pedicle anchor 21 during the operation, the present invention creates an innovative screwdriver 92 to overcome the aforementioned problems. As shown in FIG. 23, the screwdriver 92 includes: a handle 921, a long-rod portion 922, a driver head 923, and two hangers 926 separately located on the left and right sides of the handle 921. The long-rod portion 922 extends a predetermined length from one end of the handle 921 along an axis. The driver head 923 is located at an end of the long-rod portion 922 away from the handle 921. The structure of the driver head 923 corresponds to the fitting structure 214 of the two-piece suspension pedicle anchor 21 of the present invention and can be connected with the fitting structure 214 of the two-piece suspension pedicle anchor 21; such that, when the handle 921 rotates, the driver head 923 will also drive the proximal piece 2111 of the two-piece suspension pedicle anchor 21 to rotate. The two hangers 926 are respectively assembled on the left and right sides of the handle 921 or the long-rod portion 922 in a detachable manner. The two hangers 926 can be respectively wound around the closed end 231 and the open end 232 of the artificial ligament 23 extending from the through hole 215 of the two-piece suspension pedicle anchor 21. By detaching the two hangers 926 from the handle 921, the head closed end 231 and the tail open end 232 of the artificial ligament 23 can be removed directly and quickly from the screwdriver 92. In one embodiment, the two hangers 926 can be in a structure similar to a screw, which can be rotated forwardly and screwed into the screw holes provided on the handle 921 to be assembled on the handle portion 921; in addition, the two hangers 926 can also be easily removed from the handle 921 by rotating the screws (hangers 926) reversely.

Figure 24:
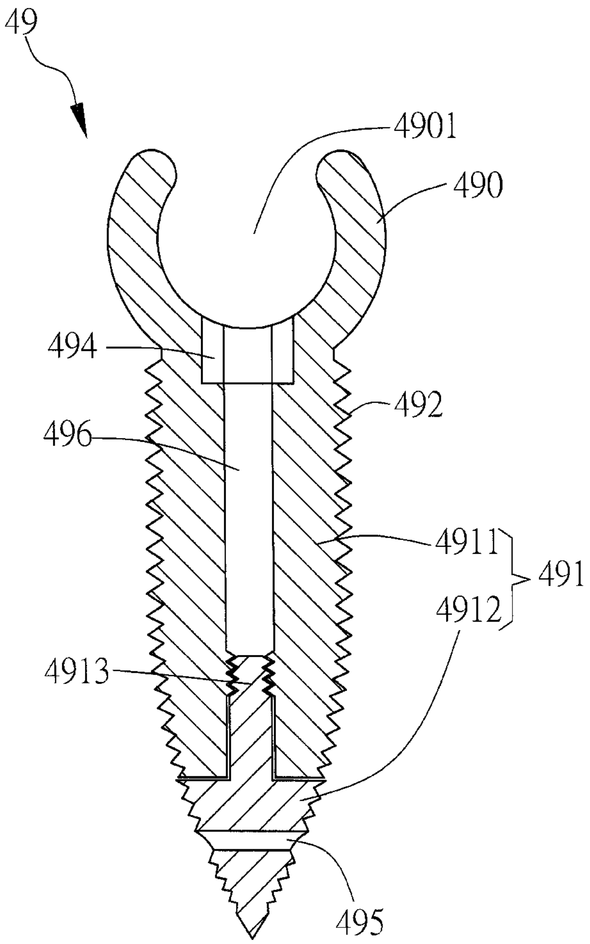
FIG. 24 is a schematic cross-sectional view of the third embodiment of the two-piece suspension pedicle anchor of the present invention.

Please refer to FIG. 24, which is a schematic cross-sectional view of the third embodiment of the two-piece suspension pedicle anchor of the present invention. The structure of the two-piece suspension pedicle anchor 49 shown in this embodiment is almost the same as that of the two-piece suspension pedicle anchor 21 shown in FIG. 21, and the method of use is also similar. In the embodiment shown in FIG. 24, the two-piece suspension pedicle anchor 49 also has a two-piece elongated columnar body 491 extending along a central axis (the columnar body 491 includes a proximal piece 4911 and a distal piece 4912), an external thread 492 disposed on the outer surface of the columnar body 491, a fitting structure 494 disposed at the top end of the proximal piece 4911 of the columnar body 491, and a transverse through hole 495 penetrating through the distal piece 4912 of the columnar body 491. The distal piece 4912 also has a central rod 4913 which is accommodated in a central rod hole 496 provided in the proximal piece 4911, and the central rod 4913 and the central rod hole 496 are provided with reverse threads that can be engaged with each other correspondingly (the so-called reverse thread means that the thread direction is opposite to the external thread on the outer surface of the proximal piece). The only difference between the pedicle anchor 21 shown in FIG. 21 and the two-piece suspension pedicle anchor 49 shown in FIG. 24 is that, a U-shaped rod-holding rack 490 is additionally provided at the top end of the columnar body of the pedicle anchor 49 shown in FIG. 24. The rod-holding rack 490 has a rod-holding seat 4901 for accommodating a connecting rod (not shown in the figure), so that the T-PAS system of the present invention can be used with a conventional spinal fixator. Wherein, the U-shaped rod-holding rack 4901 of the pedicle anchor 49 can be a fixed head rod-holding rack or a polyaxial head rod-holding rack.

Figure 25:
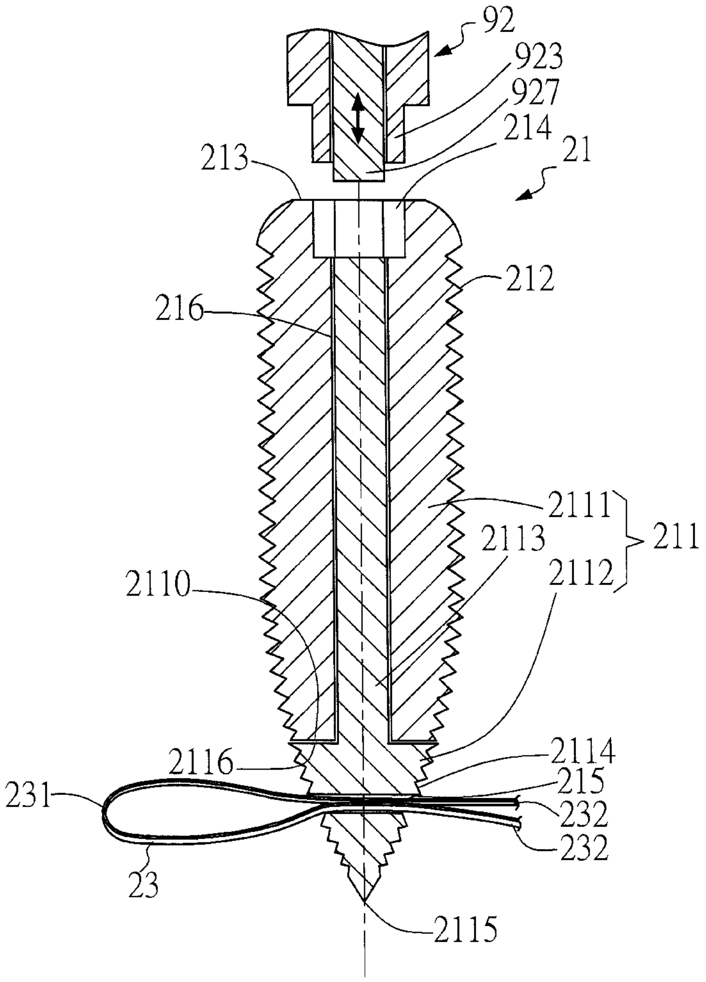
FIG. 25 is a schematic cross-sectional view of the fourth embodiment of the two-piece suspension pedicle anchor of the present invention.

Please refer to FIG. 25, which is a schematic cross-sectional view of the fourth embodiment of the two-piece suspension pedicle anchor of the present invention. The structure of the two-piece suspension pedicle anchor 21 shown in this fourth embodiment of FIG. 25 is almost the same as that of the one shown in FIG. 21, and the method of use is also similar, and thus the same components will be given the same names and numbers, and their details will not be repeated. In the fourth embodiment shown in FIG. 25, the two-piece suspension pedicle anchor 21 also includes: a columnar body 211, an external thread 212, a fitting structure 214, and a through hole 215. The columnar body 211 is also composed of a proximal piece 2111 and a distal piece 2112. The distal piece 2112 also has a central rod 2113. The only difference of the two-piece suspension pedicle anchor 21 of the fourth embodiment shown in FIG. 25 is that, the central rod 2113 of the distal piece 2112 in this embodiment extends upward to the bottom of the fitting structure 214; in addition, the central rod 2113 is not provided with a rod top external thread, and the central rod hole 216 of the proximal piece 2111 is also not provided with a rod hole internal thread. The top end of the central rod 2113 of the distal piece 2112 can be pushed against the front end of a retractable thin push rod 927 provided by the screwdriver 92. By extending the thin push rod 927 of the screwdriver 92 forward (outward), the central rod 2113 of the distal piece 2112 (together with the distal piece 2112) can be pushed forward (outward) away from the proximal piece 2111, in order to move the top end 2116 of the distal piece 2112 away from the bottom end 2110 of the proximal piece 2111 (i.e., there will be a gap between the top end 2116 of the distal piece 2112 and the bottom end 2110 of the proximal piece 2111).

Please refer to FIG. 26A, FIG. 26B, FIG. 26C and FIG. 26D, which respectively are the schematic diagrams showing the four steps of a method to fix the two-piece suspension pedicle anchor of the fourth embodiment to the pedicle of the lower vertebral segment by using the screwdriver 92 having the retractable thin push rod 927 of the present invention. The screwdriver 92 shown in FIG. 26A to FIG. 26D is roughly the same in structure as the screwdriver 92 shown in FIG. 23, so the same components will be given the same names and numbers, and the details thereof will not be repeated. The screwdriver 92 of this embodiment also includes a handle 921, a long-rod portion 922, a driver head 923, and two hangers 926 respectively disposed on the left and right sides of the handle 921. The structure of the driver head 923 corresponds to the fitting structure 214 and can be connected with the fitting structure 214 of the two-piece suspension pedicle anchor 21; such that, when the handle 921 rotates, the driver head 923 will also drive the proximal piece 2111 of the two-piece suspension pedicle anchor 21 to rotate. The two hangers 926 are respectively assembled on the left and right sides of the handle 921 or the long-rod portion 922 in a detachable manner. The two hangers 926 can be respectively wound around the closed end 231 and the open end 232 of the artificial ligament 23 extending from the through hole 215 of the two-piece suspension pedicle anchor 21. The difference of the screwdriver 92 shown in FIG. 26A to FIG. 26D is that, there is a hollow tube formed in the center of the handle 921 and the long-rod portion 922, and a thin push rod 927 is arranged in the hollow tube in a retractable manner. The rear end of the thin push rod 927 is combined with an adjustment module 928. The structure and mechanism of the adjustment module 928 are similar to the blade retractable adjuster of common utility knives in the market, which includes a pusher 9281 and a locking teeth groove 9282. The pusher 9281 is engaged with the teeth of the locking teeth groove 9282 by an elastic member. Pushing the pusher 9281 by external force can make the pusher 9281 to move forward and backward along the locking teeth groove 9282. When the external force disappears, the teeth of the locking teeth groove 9282 can provide a positioning effect to the pusher 9281. The rear end of the thin push rod 927 is combined with the pusher 9281. When the pusher 9281 is pushed to move forward (downward) along the locking teeth groove 9282, the thin push rod 927 will also be driven by the pusher 9281 to extend forward (outward) and protrude out of the driver head 923 of the screwdriver 92. Vice versa, when the pusher 9281 is pushed to move backward (upward) along the locking teeth groove 9282, the thin push rod 927 will be driven by the pusher 9281 to retract backward (inward). A ruler scale is set on the side of the locking teeth groove 9282 for the operator to know how far (long) the thin push rod 927 is pushed out.

Figure 26A:
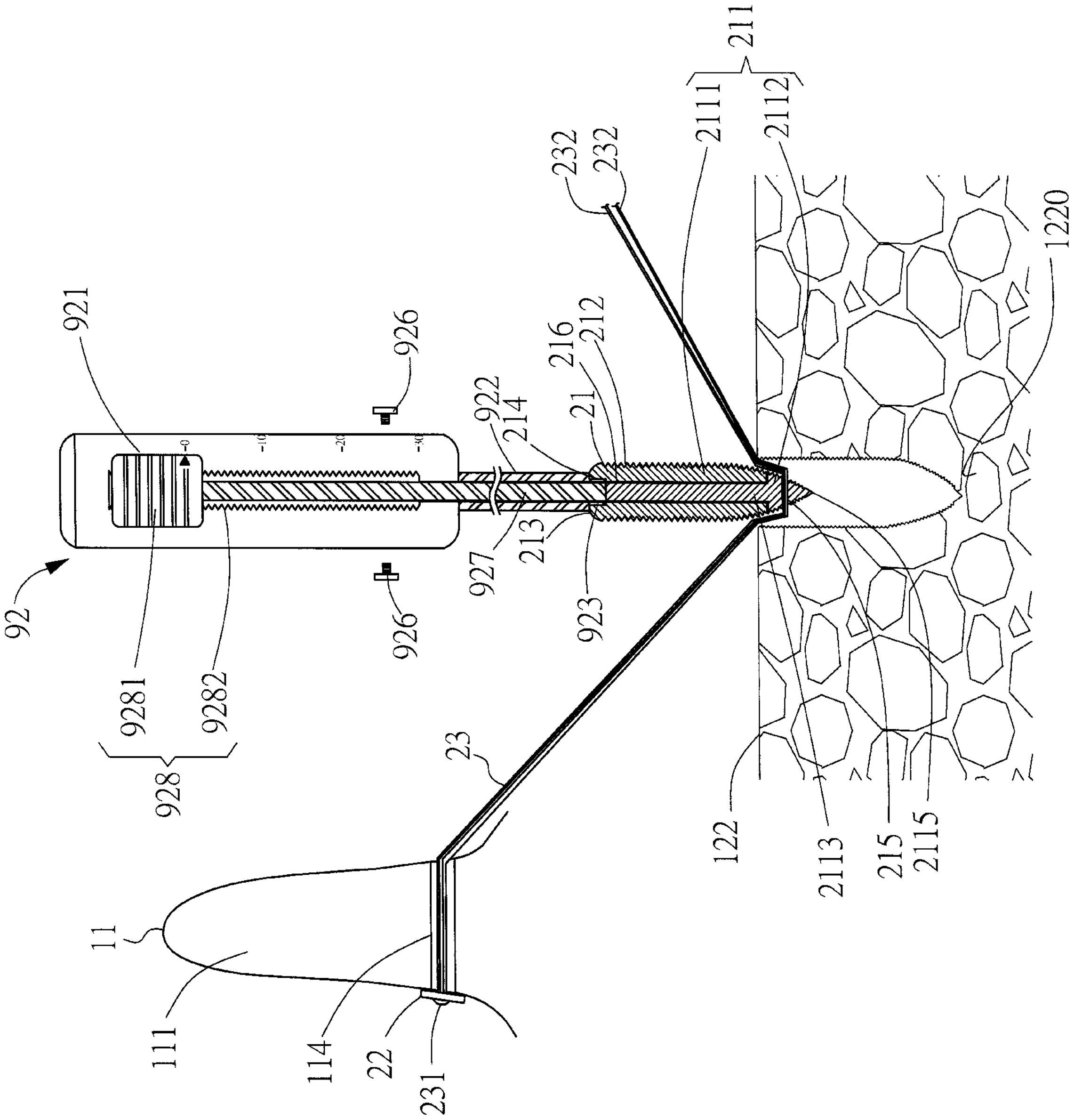
FIG. 26A, FIG. 26B, FIG. 26C and FIG. 26D are respectively the schematic diagrams showing the four steps of a method to fix the two-piece suspension pedicle anchor of the fourth embodiment to the pedicle of the lower vertebral segment by using the screwdriver having the retractable thin push rod of the present invention.
Figure 26B:
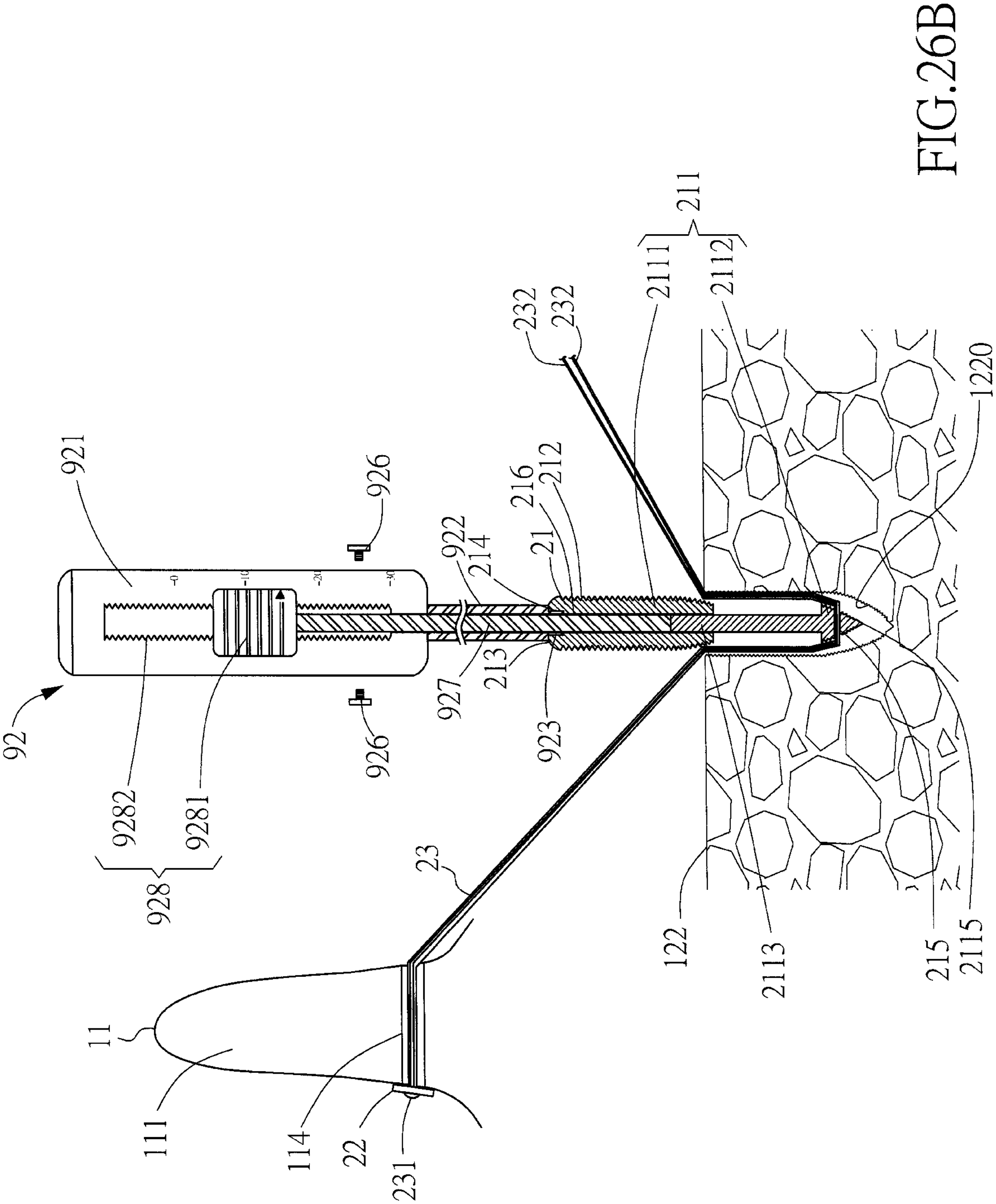
Figure 26C:
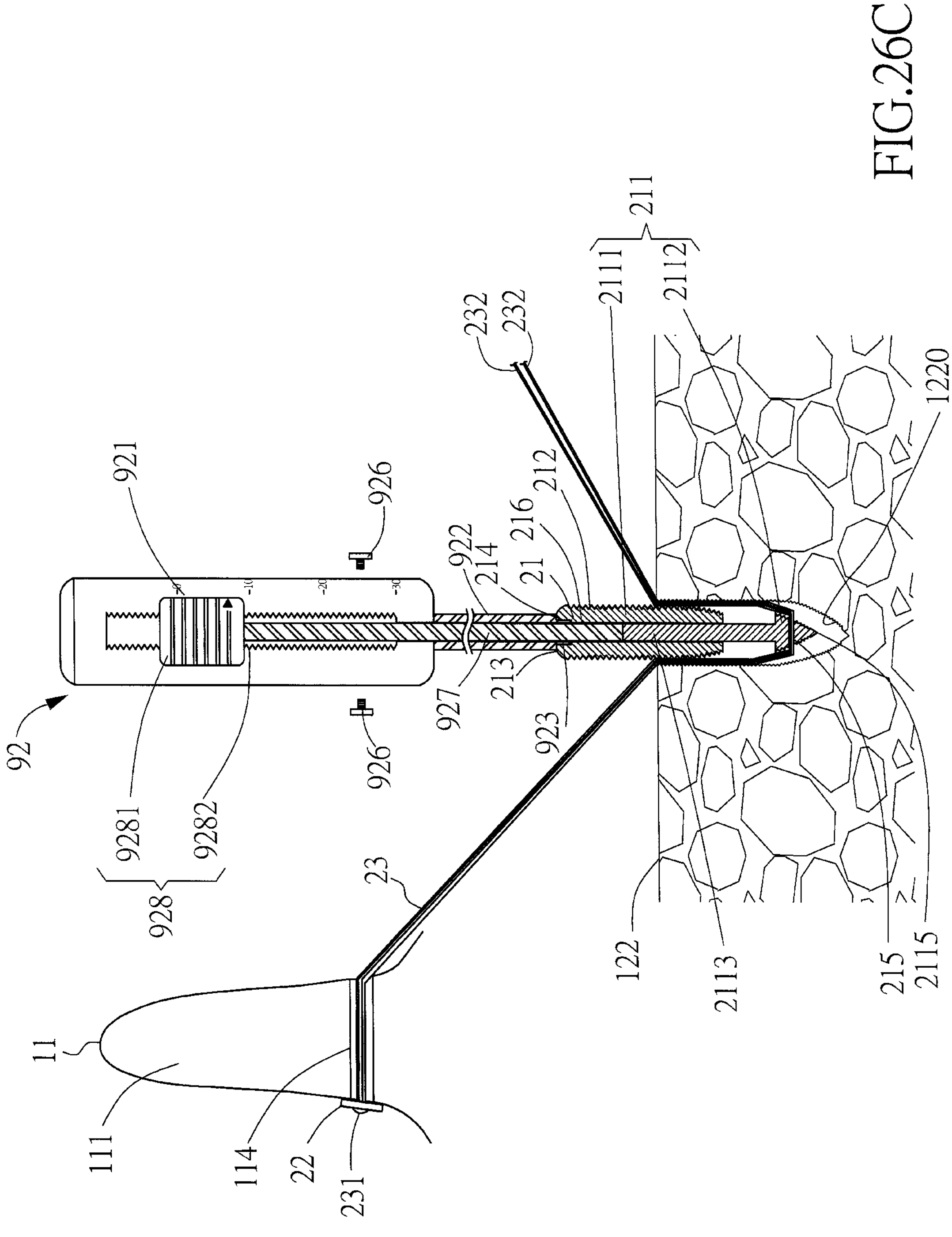
Figure 26D:
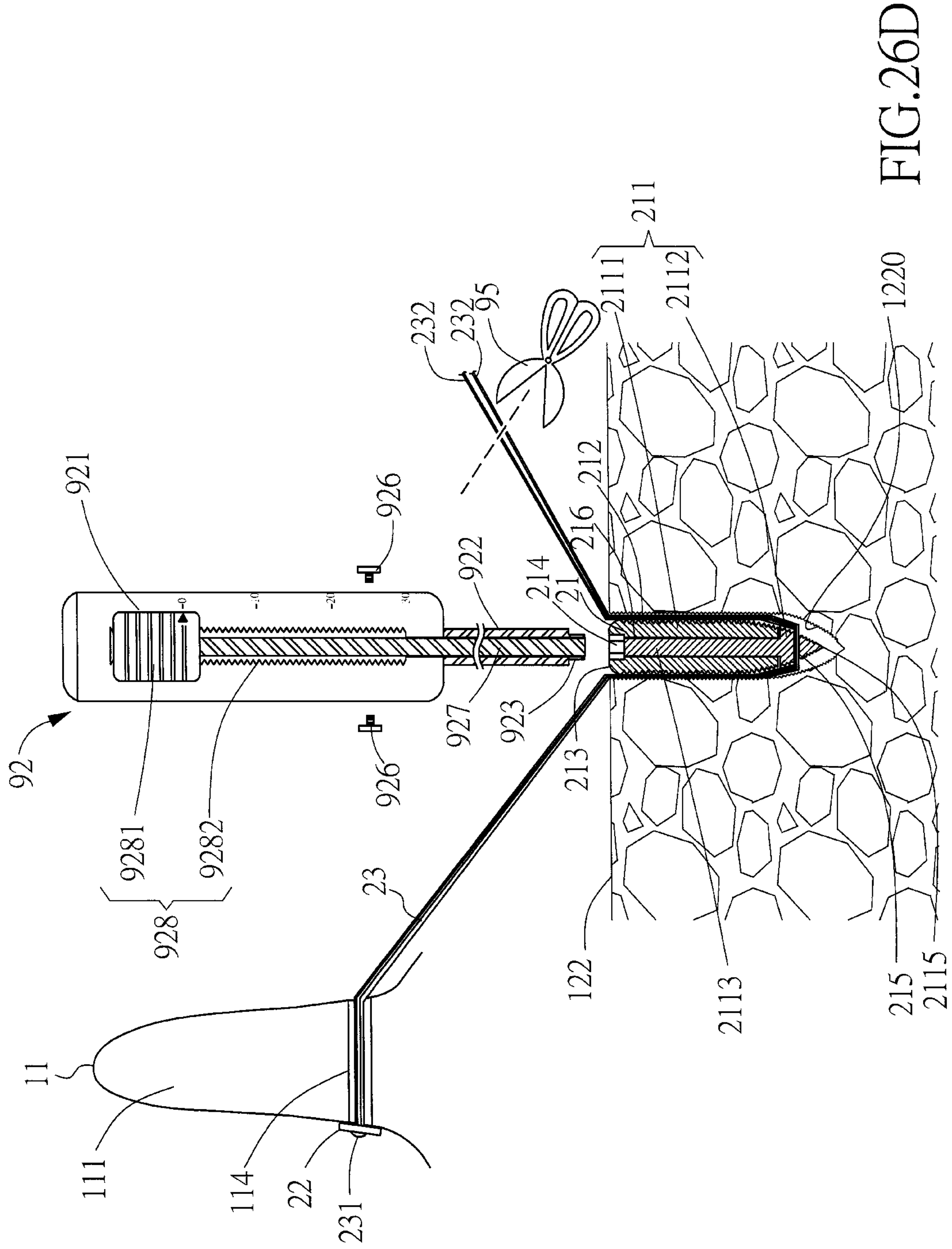

As shown in FIG. 26A, when the two-piece suspension pedicle anchor 21 is placed at the opening of the pre-drilled bone hole 1220 in the pedicle 122 of the lower vertebral segment, but the proximal piece 2111 has not been completely locked into the bone hole 1220, the driver head 923 of the screwdriver 92 is plugged into the fitting structure 214 of the two-piece suspension pedicle anchor 21. At this moment, the adjustment module 928 of the screwdriver 92 can be operated by pushing the pusher 9281 forward (downward) along the locking teeth groove 9282; so that the thin push rod 927 protrudes outward from the front end of the long-rod portion 922 and exposed out of the driver head a bit, which in turn abuts the top end of the central rod 2113 of the distal piece 2112. And then, as shown in FIG. 26B, the proximal piece 2111 is still not fully locked into the bone hole 1220. At this time, continue to push the pusher 9281 forward (downward) by operating the adjustment module 928 of the screwdriver 92 in order to extend the thin push rod 927 outward (downward), thereby pushing the distal piece 2112 forward (outward, downward) away from the proximal piece 2111, and making a gap between the top end 2116 of the distal piece 2112 and the bottom end 2110 of the proximal piece 2111. In the meantime, the artificial ligament 23 passing through the through hole 215 of the distal piece 2112 will also be pulled downward by the distal piece 2112, thereby increasing the tension of the artificial ligament 23. In other words, the user can adjust the distance between the distal piece 2112 and the proximal piece 2111 by operating the adjustment module 928, thereby adjusting the tension value of the artificial ligament 23 to reach the aforementioned first tension. The ruler scale on the side of the locking teeth groove 9282 allows the user to know how far (long) the thin push rod 927 has been pushed out. As shown in FIG. 26C, when the tension of the artificial ligament 23 reaches the first tension value, the handle 921 of the screwdriver 92 can be rotated, so that the driver head 923 of the screwdriver drives the proximal piece 2111 of the two-piece suspension pedicle anchor 21 to rotate (forward rotation) and gradually locks the proximal piece 2111 down inside the bone hole 1220. At this moment, before the proximal piece 2111 reaches the depth of the distal piece 2112, the distal piece 2112 remains at its original position, so the tension of the artificial ligament 23 remains at the first tension. In addition, when the proximal piece 2111 is rotated and locked into the bone hole 1220 by the driver head 923 of the screwdriver 92, the distal piece 2112 will not be driven to rotate together; such that, the artificial ligament 23 which is brought into the bone hole 1220 by the distal piece 2112 will remain approximately at the same location on the outer surface of the proximal piece 2111, and the artificial ligament 23 will not wrap around the outer surface of the proximal piece 2111 due to the rotation of the proximal piece 2111. As shown in FIG. 26D, continue to rotate the handle 921 of the screwdriver 92, so that the driver head 923 of the screwdriver drives the proximal piece 2111 of the two-piece suspension pedicle anchor 21 to continue to rotate and lock down into the bone hole 1220 deeper, until the proximal piece 2111 contacts and abuts against the distal piece 2112. At this moment, check whether the tension value of the artificial ligament 23 has reached the range of the predetermined tension. If the tension value of the artificial ligament 23 has not reached the predetermined tension, operate the handle 921 of the screwdriver 92, so that the driver head 923 of the screwdriver drives the proximal piece 2111 of the two-piece suspension pedicle anchor 21 to rotate (forward rotation) and continue to lock the proximal piece 2111 down deeper into the bone hole 1220. At this moment, since the proximal piece 2111 has contacted and abutted against the distal piece 2112, the proximal piece 2111 will start pushing the distal piece 2112 to move down further into the bone hole 1220, and the tension of the artificial ligament 23 will be increased until the tension value of the artificial ligament 23 reaches the predetermined tension. Generally speaking, at this time (that is, when the tension value of the artificial ligament 23 reaches the predetermined tension), the position of the top end 213 of the two-piece suspension pedicle anchor 21 of the present invention is about the same as or slightly lower than the top opening of the bone hole 1220. Once the tension value of the artificial ligament 23 has reached the predetermined tension, the pusher 9281 of the screwdriver 92 can be operated to retract the thin push rod 927 upwards, let the thin push rod 927 no longer abuts the top of the central rod 2113 of the distal piece 2112. Then, take the screwdriver 92 away from the fitting structure 214 of the proximal piece 2111 of the two-piece suspension pedicle anchor 21, and complete the operation process of fixing one end of the artificial ligament 23 to the pedicle 122 of the lower vertebral segment by using the two-piece suspension pedicle anchor 21 of the present invention and making the tension of the artificial ligament 23 to reach the predetermined tension.

Figure 27:
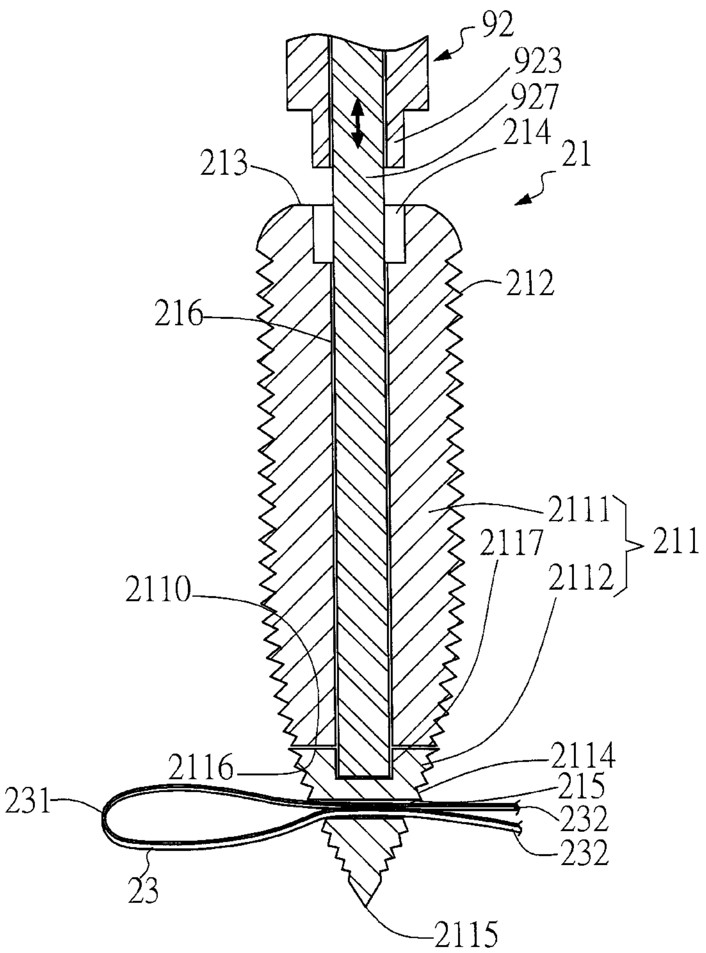
FIG. 27 is a schematic cross-sectional view of the fifth embodiment of the two-piece suspension pedicle anchor of the present invention with a screwdriver.

Please refer to FIG. 27, which is a schematic cross-sectional view of the fifth embodiment of the two-piece suspension pedicle anchor of the present invention with a screwdriver. Because the structure and function of the two-piece suspension pedicle anchor 21 shown in this fifth embodiment of FIG. 27 is almost the same as that of the one shown in FIG. 25 and FIG. 26A to FIG. 26D, thus the same components will be given the same names and numbers, and their details will not be repeated. As shown in FIG. 27, the two-piece suspension pedicle anchor 21 of the fifth embodiment also comprises: a columnar body 211, an external thread 212, a fitting structure 214 and a through hole 215. The columnar body 211 is also composed of a proximal piece 2111 and a distal piece 2112. The only difference of the two-piece suspension pedicle anchor 21 of the fifth embodiment shown in FIG. 27 is that, although the proximal piece 2111 of the two-piece suspension pedicle anchor 21 of the fifth embodiment is provided with a central rod hole 216, but the distal piece 2112 is not provided with any central rod. Correspondingly, a recess 2117 corresponding to the central rod hole 216 is provided at the top end 2116 of the distal piece 2112. When the driver head 923 of the screwdriver 92 is assembled to the fitting structure 214 at the top end of the proximal piece 2111, and the pusher of the adjustment module is operated to move forward, the thin push rod 927 will protrude downward and pass through the central rod hole 216 of the proximal piece 2111 and then plug into the recess 2117 of the distal piece 2112; and then, the operation of pushing the distal piece 2112 downward and away from the proximal piece 2111 can be achieved by operating the pusher of the adjustment module to make the thin push rod 927 to extend further downward.

Figure 28:
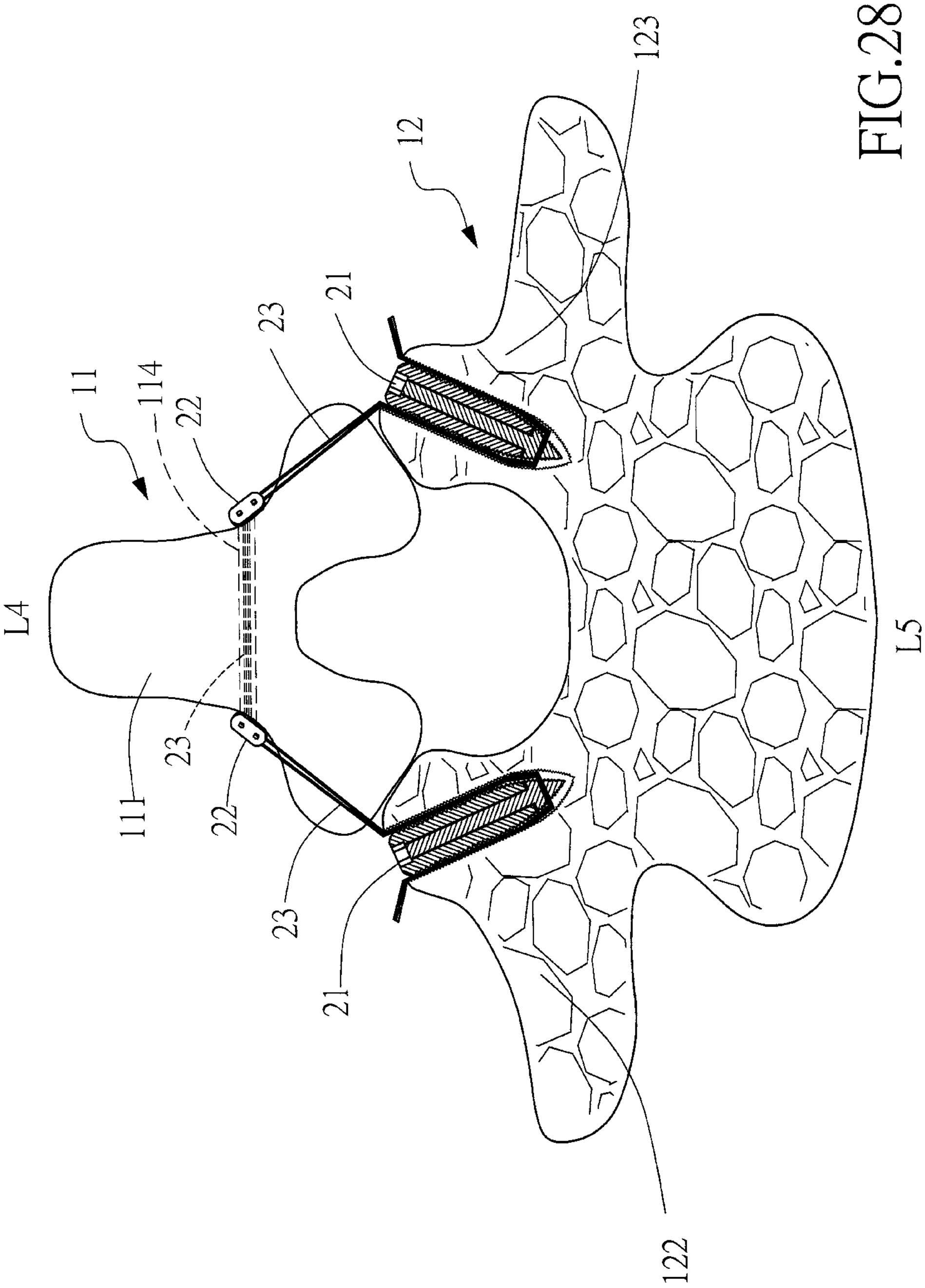
FIG. 28 is a schematic cross-sectional view of an embodiment of the two-piece suspension pedicle anchor which is used in the T-PAS system of the present invention and installed on two adjacent vertebral segments of the human spine.

Please refer to FIG. 28, which is a schematic cross-sectional view of an embodiment of the two-piece suspension pedicle anchor which is used in the T-PAS system of the present invention and installed on two adjacent vertebral segments of the human spine. After the operation of T-PAS system, the positions of the of the two-piece suspension pedicle anchors 21 are about the same as or slightly lower than the surfaces of the pedicles 122, 123 at two sides of the lower vertebral segment 12. Since the distal piece will not rotate together with the proximal piece when the proximal piece of the two-piece suspension pedicle anchor 21 is driven and locked into the bone holes of the pedicles 122 and 123, so the artificial ligaments 23 brought by the distal piece deep into the bone hole will remain roughly on the outer surfaces of both sides of the proximal piece. Thus, the artificial ligament 23 only extends straight upwards and is sandwiched and fixed between the outer surface of the proximal piece and the inner surface of the bone hole of the pedicle 122, 123; the artificial ligament 23 does not rotate nor wrap around the outer surface of the proximal piece. This novel design not only makes it easier to control and adjust the tension value of the artificial ligament 23, but also avoids the artificial ligament 23 from loosening from the opening of the bone hole or being scratched by the bone and reducing the service life.

Figure 29:
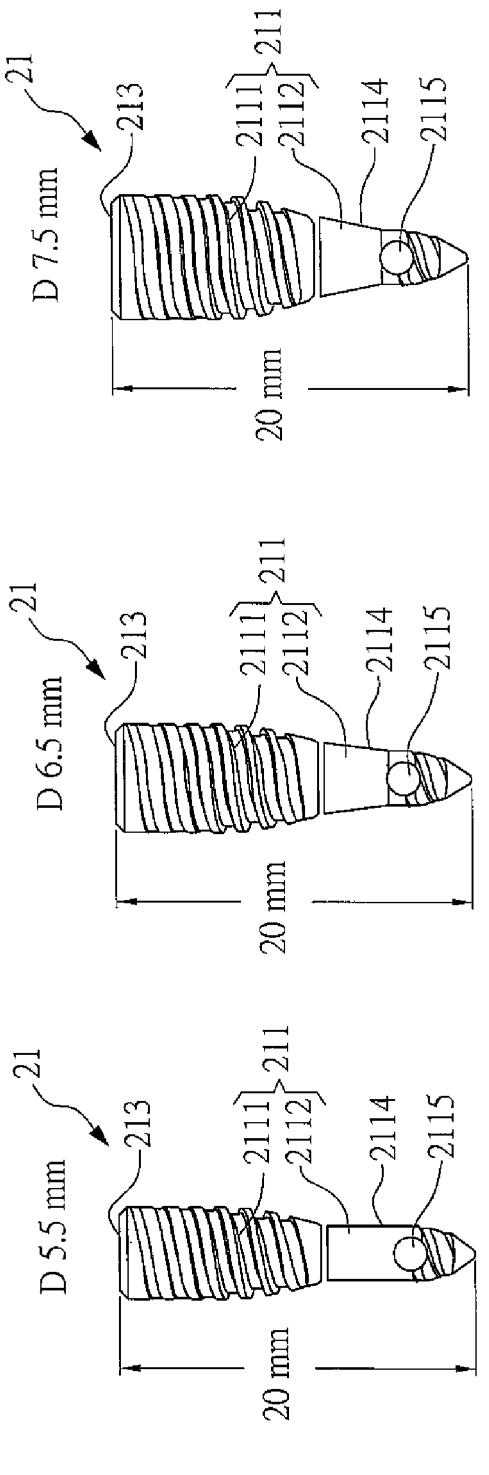
FIG. 29 is a schematic diagram of the appearances of three short-version two-piece suspension pedicle anchors of the present invention with different sizes.

Please refer to FIG. 29, which is a schematic diagram of the appearances of three short-version two-piece suspension pedicle anchors of the present invention with different sizes. Several two-piece suspension pedicle anchors 21 of different sizes and specifications can be produced in advance in order to adapt to different vertebrae sizes or structures of different patients or different surgical needs. In the embodiments of the short-version two-piece suspension pedicle anchors 21 shown in FIG. 29, the tips of the external threads of the proximal piece 2111 are de-sharpened to avoid scratching the artificial ligament during locking into the bone hole; in addition, only the lower part of the outer surface 2114 of the distal piece 2112 is provided with external threads, while the upper part of the outer surface 2114 of the distal piece 2112 is a smooth surface without threads.

Figure 30C:
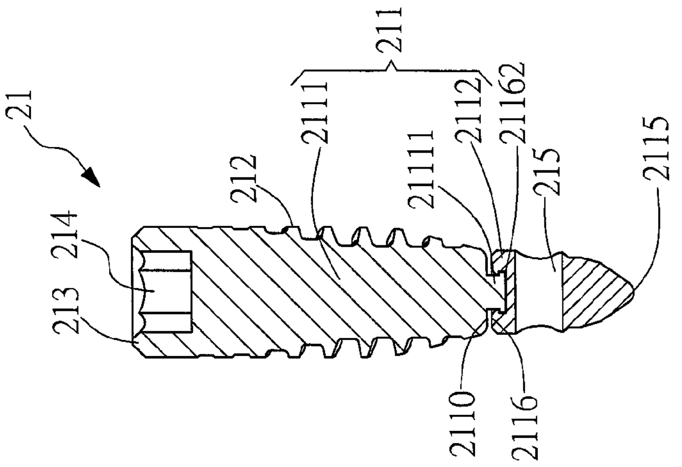
FIG. 30A to FIG. 30C are schematic diagrams of the sectional views of the sixth, seventh and eighth embodiments of the two-piece suspension pedicle anchor of the present invention with different designs.
Figure 30B:
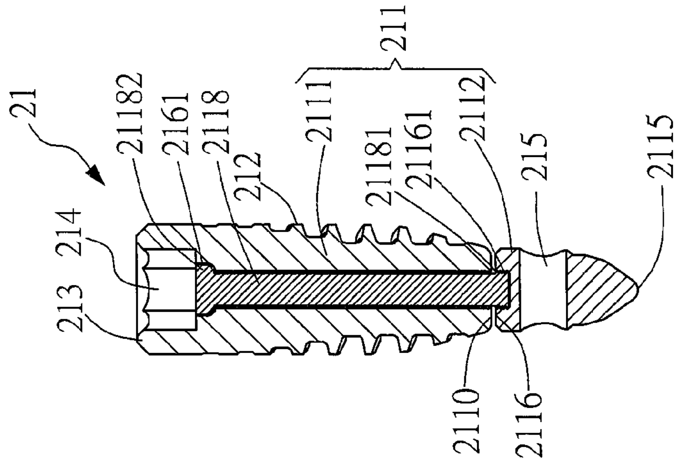
Figure 30A:
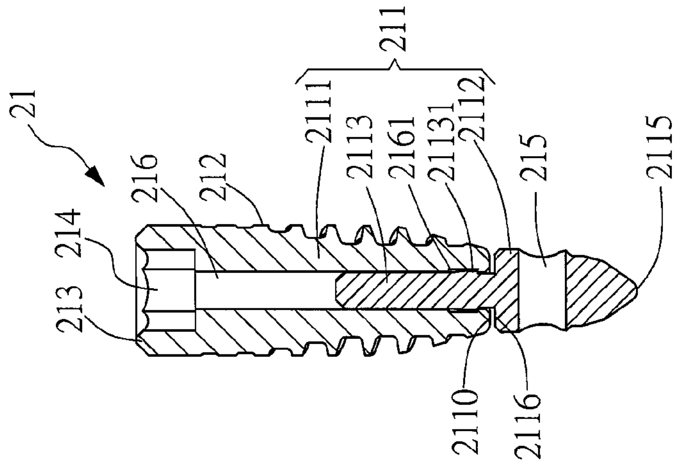

Please refer to FIG. 30A to FIG. 30C, which are schematic diagrams of the sectional views of the sixth, seventh and eighth embodiments of the two-piece suspension pedicle anchor of the present invention with different designs. The structures of the two-piece suspension pedicle anchors 21 shown in the sixth, seventh and eighth embodiments of FIG. 30A to FIG. 30C are almost the same as that of the one shown in FIG. 20A or FIG. 27, and the method of use is also similar, and thus the same components will be given the same names and numbers, and their details will not be repeated. Generally speaking, in the sixth, seventh and eighth embodiments shown in FIG. 30A to FIG. 30C, the distal piece 2112 of the two-piece suspension pedicle anchor 21 can only rotate relative to the proximal piece 2111 according to the central axis, but the distal piece 2112 cannot move linearly relative to the proximal piece 2111 along the central axis. That means, the distal piece 2112 can rotate relative to but cannot detach from the proximal piece 2111.

As shown in FIG. 30A, the two-piece suspension pedicle anchor 21 also comprises: a columnar body 211, an external thread 212, a fitting structure 214 and a through hole 215; in addition, the columnar body 211 is also composed of a proximal piece 2111 and a distal piece 2112. The differences between this sixth embodiment and the previously illustrated first embodiment of FIG. 20A include the followings. In the sixth embodiment of the two-piece suspension pedicle anchor 21 shown in FIG. 30A, a bulged-part 21131 is provided on a peripheral surface of the central rod 2113 of the distal piece 2112. In the central rod hole 216 of the proximal piece 2111, a dented-part 2161 that can accommodate the bulged-part 21131 is provided in the central rod hole 216 at a position relative to the bulged-part 21131. The diameter (or width) of the bulged-part 21131 is slightly larger (around 0.02 mm~0.2 mm larger) than the diameter of the central rod hole 216 at the bottom end 2110 of the proximal piece 2111. In addition, the diameter of the dented-part 2161 of the central rod hole 216 is slightly larger (around 0.02 mm~0.2 mm larger) than the diameter (or width) of the bulged-part 21131. By plugging the central rod 2113 into the central rod hole 216, the bulged-part 21131 will be received and kept in the dented-part 2161, such that the distal piece 2112 can rotate relative to the proximal piece 2111 according to the central axis, but the distal piece 2112 cannot be detached from the proximal piece 2111.

As shown in FIG. 30B, the two-piece suspension pedicle anchor 21 also comprises: a columnar body 211, an external thread 212, a fitting structure 214 and a through hole 215; in addition, the columnar body 211 is also composed of a proximal piece 2111 and a distal piece 2112. The differences between this seventh embodiment and the previously illustrated fifth embodiment of FIG. 27 include the followings. In the seventh embodiment of the two-piece suspension pedicle anchor 21 shown in FIG. 30B, an elongated spindle 2118 is exposed in the central rod hole 216 of the proximal piece 2111. The length of the spindle 2118 is larger than the length of the central rod hole 216. The top end of the spindle 2118 has a rim-part 21182 having a diameter larger than the diameter of the central rod hole 216. The top end of the central rod hole 216 has a concave-part 2161 having a diameter slightly larger than the diameter of the rim-part 21182 of the spindle 2118. The bottom end of the spindle 2118 has a bulged-part 21181 which is exposed outside the bottom opening of the central rod hole 216. The top end 2116 of the distal piece 2112 is formed with a dented-part 21161 that can accommodate the bulged-part 21181 of the spindle 2118. By plugging the spindle 2118 downward into the central rod hole 216 via the concave-part 2161, and making the bulged-part 21181 of the spindle 2118 to extend out of the central rod hole 216 and then plug into the dented-part 21161 of the distal piece 2112, the bulged-part 21181 will be received and kept in the dented-part 21161, such that the distal piece 2112 can rotate relative to the proximal piece 2111 according to the central axis, but the distal piece 2112 cannot be detached from the proximal piece 2111. In one embodiment, the structure of the bulged-part 21181 and the dented-part 21161 of this seventh embodiment are similar to the ones previously illustrated in the sixth embodiment. In another embodiment, there are screw-threads between the bulged-part 21181 and the dented-part 21161 that can be screwed together, such that the bulged-part 21181 of the spindle 2118 can be locked on the dented-part 21161 of the distal piece 2112 by means of screw-threads.

As shown in FIG. 30C, the two-piece suspension pedicle anchor 21 also comprises: a columnar body 211, an external thread 212, a fitting structure 214 and a through hole 215; in addition, the columnar body 211 is also composed of a proximal piece 2111 and a distal piece 2112. The differences between this eighth embodiment and the previously illustrated seventh embodiment of FIG. 27 include the followings. In the eighth embodiment of the two-piece suspension pedicle anchor 21 shown in FIG. 30C, a bulged-part 21111 is provided on the bottom end 2110 of the proximal piece 2111. In addition, a dented-part 21162 that can accommodate the bulged-part 21111 in a rotatable manner is provided on the top end 2116 of the distal piece 2112. The bottom rim-part of the bulged-part 21111 has a diameter slightly larger than the diameter of the top-opening of the bulged-part 21111. By plugging the bulged-part 21111 into the dented-part 21162, the bulged-part 21111 will be received and kept in the dented-part 21162 in a rotatable manner, such that the distal piece 2112 can rotate relative to the proximal piece 2111 according to the central axis, but the distal piece 2112 cannot be detached from the proximal piece 2111.

To summary, the embodiments illustrated in FIGS. 20A to 30C refer to the two-piece suspension pedicle anchor with "free-rotating distal piece".

Design Concept

1. The two pieces won't simultaneously rotate in the same direction as the proximal piece is driven into the tapped hole.
2. Increased tension of the ligament with the proximal piece driving further downward.
3. Secure bone-anchor interface fixation occurs on both sides (i.e., the outer peripheral surface) of proximal piece which had a larger diameter than the distal piece.

Technique

After preparing of laminar tunnel, the loop-end side of the ligament was pulled to the contralateral lamina through a passer (or round needle) and a pig-nose washer is used to secure the ligament and as a stopper on the contralateral lamina. The ligament on the free-end side was gently tensioned as the tip (distal piece) of the anchor is placed into the entry of the tapped bone-hole. The tapered anchor that is placed inside of the tapped bone-hole is about 25-30% of total length of anchor (ps. % may vary with different tapered design), and the ideal tension of the ligament on the loop-end side can be achieved as the proximal piece is gradually driven down with a hexagonal driver.

While the present invention has been particularly shown and described with reference to a preferred embodiment, it will be understood by those skilled in the art that various changes in form and detail may be without departing from the spirit and scope of the present invention.

What is claimed is:

1. A two-piece suspension pedicle anchor, comprising:

an elongated columnar body extending along a central axis;

an external thread arranged on an outer surface of the columnar body;

a fitting structure arranged at a top end of the columnar body; and a through hole laterally penetrating through the columnar body;

wherein:

the columnar body includes a proximal piece and a distal piece to present a two-piece columnar structure; the distal piece is assembled at a bottom end of the proximal piece, and the proximal piece is rotatable relative to the distal piece according to the central axis; the fitting structure is disposed on a top end of the proximal piece at a position away from of the distal piece; the external thread of the columnar body is disposed at least on an outer surface of the proximal piece; the through hole is disposed on the distal piece, and an extending direction of the through hole is not parallel to the central axis;

the extending direction of the through hole of the distal piece is perpendicular to the central axis; in addition, a U-shaped rod-holding rack is provided at the top end of the proximal piece of the columnar body.

2. The two-piece suspension pedicle anchor of claim 1, wherein, the bottom end of the proximal piece is provided with a central rod hole extending along the central axis toward the top end of the proximal piece; a top end of the distal piece is provided with a central rod protruding along the direction of the central axis; the size and position of the central rod correspond to the central rod hole, and the central rod is inserted into the central rod hole; the distal piece and the proximal piece can be assembled into the columnar body by inserting the central rod into the central rod hole; in addition, the proximal piece can rotate relative to the distal piece according to the central axis.

3. The two-piece suspension pedicle anchor of claim 2, wherein, a rod top external thread is provided on a top of the central rod of the distal piece; in the central rod hole of the proximal piece, a rod hole internal thread that can engage with the rod top external thread is provided at a position relative to the rod top external thread; wherein, the thread direction of the rod top external thread and the thread direction of the external thread of the columnar body are opposite.

4. The two-piece suspension pedicle anchor of claim 2, wherein, a top end of the central rod of the distal piece can be pushed by a front end of a retractable thin push rod provided by a screwdriver; by extending the thin push rod of the screwdriver forward, the central rod and the distal piece can be pushed forward away from the proximal piece.

5. The two-piece suspension pedicle anchor of claim 1, wherein, the through hole allows an artificial ligament to pass through, so that the two-piece suspension pedicle anchor can be hung on the artificial ligament; the fitting structure can be connected with a screwdriver, such that, by operating the screwdriver, the two-piece suspension pedicle anchor is driven to rotate about the central axis, and the two-piece suspension pedicle anchor is adapted to be screwed and fixed to a bone, such that a portion of the artificial ligament is clamped and fixed between the outer surface of the proximal piece and the bone; in addition, when the screwdriver is operated to drive the two-piece suspension pedicle anchor to rotate about the central axis and gradually lock into the bone, only the proximal piece is driven and rotated by the screwdriver, and the distal piece is not be rotated by the screwdriver; therefore, the artificial ligament passing through the through hole of the distal piece does not rotate nor wrap around the outer surface of the proximal piece.

6. The two-piece suspension pedicle anchor of claim 5, wherein, the two-piece suspension pedicle anchor is for use in a translaminar pedicle anchor suspension system (T-PAS system); the T-PAS system is capable of being adapted to be installed in a spine having at least an upper vertebral segment and a lower vertebral segment; the T-PAS system comprising:

at least one said two-piece suspension pedicle anchor, capable of being adapted to be fixed to one of two pedicles of the lower vertebral segment; and at least one said artificial ligament, one end of the artificial ligament being fixed to the two-piece suspension pedicle anchor and thus adapted to be fixed to the pedicle of the lower vertebral segment, the other end of the artificial ligament being adapted to be connected to a contralateral side-surface of a lamina of the upper vertebral segment by a connecting structure; the artificial ligament configured to be tightened to a predetermined tension, such that the upper vertebral segment is able to be suspended by combination of the two-piece suspension pedicle anchor and the artificial ligament from the lower vertebral segment below.

7. The two-piece suspension pedicle anchor of claim 6, wherein:

each of the upper vertebral segment and the lower vertebral segment respectively includes: said lamina and two said pedicles respectively located on left and right sides of the lamina; the lamina of the upper vertebral segment is adapted to be provided with a tunnel penetrating left and right side-surfaces of the lamina;

wherein the T-PAS system further comprises at least one washer which is adapted to be located near the tunnel of the lamina of the upper vertebral segment; a length of the washer is greater than a diameter of the tunnel;

said connecting structure is configured to pass said the other end of the artificial ligament through the tunnel of the lamina of the upper vertebral segment and connect to the washer; said the other end of the artificial ligament is connected to the washer and thus configured to be fixed at a location near the tunnel of the lamina of the upper vertebral segment when the predetermined tension is applied to the artificial ligament.

8. The two-piece suspension pedicle anchor of claim 7, wherein:

the T-PAS system comprises two said two-piece suspension pedicle anchors configured to be received in the left and right pedicles of the lower vertebral segment;

the T-PAS system comprises two said washers adapted to be respectively located at left and right ends of the tunnel of the lamina of the upper vertebral segment;

the T-PAS system comprises first and second said artificial ligaments; wherein one end of the first said artificial ligament is fixed to the two-piece suspension pedicle anchor configured to be located in the left pedicle, the other end of the first said artificial ligament is adapted to be passed through the tunnel from the left side-surface to the right side-surface of the lamina of the upper vertebral segment and connected to the washer configured to be located at the right side-surface of the laminar; and wherein one end of the second said artificial ligament is fixed to the two-piece suspension pedicle anchor configured to be located in the right pedicle, the other end of the second said artificial ligament is adapted to be passed through the tunnel from the right side-surface to the left side-surface of the lamina of the upper vertebral segment and connected to the washer configured to be located at the left side-surface of the laminar.

9. The two-piece suspension pedicle anchor of claim 7, wherein, the artificial ligament has two open ends and a middle section located between said two open ends; said middle section of the artificial ligament is configured to pass through the tunnel of the lamina of the upper vertebral segment to form a closed end at the middle section of the artificial ligament; the closed end of the artificial ligament is placed on a bar portion of the washer; wherein, when a pulling force is applied from the open ends of the artificial ligament, the washer is adapted to press against the side-surface near the tunnel of the lamina of the upper vertebral segment, such that the closed end of the artificial ligament is fixed to the side-surface of the lamina of the upper vertebral segment by means of the washer.

10. A pedicle anchor for use in a translaminar pedicle anchor suspension system (T-PAS system); said T-PAS system capable of being adapted to be installed in a spine having at least an upper vertebral segment and a lower vertebral segment; said pedicle anchor being capable of being adapted to be fixed to a pedicle of the lower vertebral segment; said pedicle anchor comprising:

an elongated columnar body extending along a central axis;

an external thread arranged on an outer surface of the columnar body;

a fitting structure arranged at a top end of the columnar body; and at least one through hole laterally penetrating through a head portion of the columnar body;

wherein the through hole allows an artificial ligament to pass through, so that the pedicle anchor can be hung on the artificial ligament;

wherein the fitting structure can be connected with a screwdriver, such that, by operating the screwdriver, the pedicle anchor can be driven to rotate about the central axis, and the pedicle anchor together with the artificial ligament are adapted to be screwed and fixed to the pedicle;

wherein, an outer diameter of the head portion of the columnar body is not greater than another outer diameter of the external thread of the columnar body; when the pedicle anchor is adapted to be gradually screwed into the pedicle, the through hole of the pedicle anchor is configured to be embedded in the pedicle, such that the artificial ligament is configured to be brought into the pedicle along with the through hole and thus adapted to be clamped and sandwiched between the outer surface of the pedicle anchor and the inside of the pedicle;

wherein:

the pedicle anchor is a two-piece suspension pedicle anchor;

one end of the artificial ligament being fixed to the two-piece suspension pedicle anchor and thus adapted to be fixed to the pedicle of the lower vertebral segment, the other end of the artificial ligament being adapted to be connected to a contralateral side-surface of a lamina of the upper vertebral segment by a connecting structure; the artificial ligament configured to be tightened to a predetermined tension, such that the upper vertebral segment is able to be suspended by combination of the two-piece suspension pedicle anchor and the artificial ligament from the lower vertebral segment below;

the columnar body includes a proximal piece and a distal piece to present a two-piece columnar structure; the distal piece is assembled at a bottom end of the proximal piece, and the proximal piece is rotatable relative to the distal piece according to the central axis; the fitting structure is disposed on a top end of the proximal piece at a position away from of the distal piece; the external thread of the columnar body is disposed at least on an outer surface of the proximal piece; the through hole is disposed on the distal piece, and an extending direction of the through hole is not parallel to the central axis;

when the two-piece suspension pedicle anchor is adapted to be screwed and fixed to the pedicle, a portion of the artificial ligament is clamped and fixed between the outer surface of the proximal piece and the pedicle; in addition, when the screwdriver is operated to drive the two-piece suspension pedicle anchor to rotate about the central axis and gradually lock into the pedicle, only the proximal piece is driven and rotated by the screwdriver, and the distal piece is not be rotated by the screwdriver; therefore, the artificial ligament passing through the through hole of the distal piece does not rotate nor wrap around the outer surface of the proximal piece;

the artificial ligament has two open ends and a middle section located between said two open ends; said middle section of the artificial ligament is configured to pass through the tunnel of the lamina of the upper vertebral segment to form a closed end at the middle section of the artificial ligament; the closed end of the artificial ligament is placed on a bar portion of a washer; wherein, when a pulling force is applied from the open ends of the artificial ligament, the washer is adapted to press against the side-surface near the tunnel of the lamina of the upper vertebral segment, such that the closed end of the artificial ligament is fixed to the side-surface of the lamina of the upper vertebral segment by means of the washer.

11. The pedicle anchor of claim 10, wherein, the bottom end of the proximal piece is provided with a central rod hole extending along the central axis toward the top end of the proximal piece; a top end of the distal piece is provided with a central rod protruding along the direction of the central axis; the size and position of the central rod correspond to the central rod hole, and the central rod is inserted into the central rod hole; the distal piece and the proximal piece can be assembled into the columnar body by inserting the central rod into the central rod hole; in addition, the proximal piece can rotate relative to the distal piece according to the central axis.

12. The pedicle anchor of claim 11, wherein, a rod top external thread is provided on a top of the central rod of the distal piece; in the central rod hole of the proximal piece, a rod hole internal thread that can engage with the rod top external thread is provided at a position relative to the rod top external thread; wherein, the thread direction of the rod top external thread and the thread direction of the external thread of the columnar body are opposite.

13. The pedicle anchor of claim 11, wherein, a top end of the central rod of the distal piece can be pushed by a front end of a retractable thin push rod provided by a screwdriver; by extending the thin push rod of the screwdriver forward, the central rod and the distal piece can be pushed forward away from the proximal piece.

14. The pedicle anchor of claim 11, wherein, the extending direction of the through hole of the distal piece is perpendicular to the central axis; in addition, a U-shaped rod-holding rack is provided at the top end of the proximal piece of the columnar body.

15. A component set for use in a translaminar pedicle anchor suspension system (T-PAS system); the T-PAS system capable of being adapted to be installed in a spine having at least an upper vertebral segment and a lower vertebral segment; said component set comprising:

at least one said two-piece suspension pedicle anchor, capable of being adapted to be fixed to one of two pedicles of the lower vertebral segment;

at least one washer, which is adapted to be positioned at a lamina of the upper vertebral segment; and at least one artificial ligament, for connecting the two-piece suspension pedicle anchor and the washer; one end of the artificial ligament being fixed to the two-piece suspension pedicle anchor and thus adapted to be fixed to the pedicle of the lower vertebral segment, the other end of the artificial ligament being adapted to be connected to a contralateral side-surface of a lamina of the upper vertebral segment by means of the washer; wherein the artificial ligament is pre-assembled on the two-piece suspension pedicle anchor;

wherein the two-piece suspension pedicle anchor comprises:

an elongated columnar body extending along a central axis;

an external thread arranged on an outer surface of the columnar body;

a fitting structure arranged at a top end of the columnar body; and a through hole laterally penetrating through the columnar body;

wherein:

the columnar body includes a proximal piece and a distal piece to present a two-piece columnar structure; the distal piece is assembled at a bottom end of the proximal piece, and the proximal piece is rotatable relative to the distal piece according to the central axis; the fitting structure is disposed on a top end of the proximal piece at a position away from of the distal piece; the external thread of the columnar body is disposed at least on an outer surface of the proximal piece; the through hole is disposed on the distal piece, and an extending direction of the through hole is not parallel to the central axis;

the through hole allows the artificial ligament to pass through, so that the two-piece suspension pedicle anchor can be hung on the artificial ligament; the fitting structure can be connected with a screwdriver, such that, by operating the screwdriver, the two-piece suspension pedicle anchor is driven to rotate about the central axis, and the two-piece suspension pedicle anchor is adapted to be screwed and fixed to the pedicle, such that a portion of the artificial ligament is adapted to be clamped and fixed between the outer surface of the proximal piece and the pedicle; in addition, when the screwdriver is operated to drive the two-piece suspension pedicle anchor to rotate about the central axis, only the proximal piece is driven and rotated by the screwdriver, and the distal piece is not be rotated by the screwdriver; therefore, the artificial ligament passing through the through hole of the distal piece does not rotate nor wrap around the outer surface of the proximal piece.

16. The component set of claim 15, further comprising a screwdriver;

wherein the screwdriver comprises:

a handle;

a long-rod portion, extending a predetermined length from one end of the handle along an axis;

a driver head, located at an end of the long-rod portion away from the handle; a structure of the driver head being corresponding to and connectable with the fitting structure of the two-piece suspension pedicle anchor, such that, when the handle rotates, the driver head drives the proximal piece of the two-piece suspension pedicle anchor to rotate; and two hangers, assembled on the handle or the long-rod portion in a detachable manner; the two hangers can be respectively wound around a closed end and an open end of the artificial ligament extending from the through hole of the two-piece suspension pedicle anchor; by detaching the two hangers from the handle, the closed end and the open end of the artificial ligament can be removed directly and quickly from the screwdriver.

17. The component set of claim 16, wherein:

a hollow tube is formed in the center of the handle and the long-rod portion, and a thin push rod is arranged in the hollow tube in a retractable manner; a rear end of the thin push rod is combined with an adjustment module; the adjustment module includes a pusher and a locking teeth groove; the pusher is engaged with teeth of the locking teeth groove by an elastic member; pushing the pusher by external force can make the pusher to move forward and backward along the locking teeth groove; when the external force disappears, the teeth of the locking teeth groove can provide a positioning effect to the pusher; the rear end of the thin push rod is combined with the pusher; when the pusher is pushed to move forward along the locking teeth groove, the thin push rod will also be driven by the pusher to extend forward and protrude out of the driver head of the screwdriver; when the pusher is pushed to move backward along the locking teeth groove, the thin push rod will be driven by the pusher to retract backward; a ruler scale is set on a side of the locking teeth groove for a user to know how far the thin push rod is pushed out;

the distal piece can be pushed by a front end of the retractable thin push rod of the screwdriver; by extending the thin push rod of the screwdriver forward, the distal piece can be pushed forward away from the proximal piece.

* * * * *